(12) United States Patent
Cook et al.

(10) Patent No.: US 12,234,284 B2
(45) Date of Patent: *Feb. 25, 2025

(54) TREATMENT OF KIDNEY INJURY

(71) Applicants: National University of Singapore, Singapore (SG); Singapore Health Services PTE LTD., Singapore (SG)

(72) Inventors: Stuart Alexander Cook, Singapore (SG); Sebastian Schaefer, Singapore (SG); Anissa Anindya Widjaja, Singapore (SG)

(73) Assignees: National University of Singapore, Singapore (SG); Singapore Health Services PTE LTD., Singapore (SG)

( * ) Notice: Subject to any disclaimer, the term of this patent is extended or adjusted under 35 U.S.C. 154(b) by 208 days.

This patent is subject to a terminal disclaimer.

(21) Appl. No.: 17/751,117

(22) Filed: May 23, 2022

(65) Prior Publication Data

US 2022/0403017 A1 Dec. 22, 2022

Related U.S. Application Data

(62) Division of application No. 16/798,101, filed on Feb. 21, 2020, now Pat. No. 11,339,216.

(30) Foreign Application Priority Data

Feb. 22, 2019 (GB) ..................... 1902419

(51) Int. Cl.
| | | |
|---|---|---|
| *C07K 16/24* | (2006.01) | |
| *A61P 13/12* | (2006.01) | |
| *C07K 14/715* | (2006.01) | |
| *C12N 15/113* | (2010.01) | |

(52) U.S. Cl.
CPC ............ *C07K 16/244* (2013.01); *A61P 13/12* (2018.01); *C07K 14/7155* (2013.01); *C12N 15/1136* (2013.01)

(58) Field of Classification Search
CPC ..................... A61K 2039/55527; A61P 13/12
See application file for complete search history.

(56) References Cited

U.S. PATENT DOCUMENTS

| | | |
|---|---|---|
| 5,843,509 A | 12/1998 | Calvo Salve et al. |
| 6,649,192 B2 | 11/2003 | Alonso Fernandez et al. |
| 10,035,852 B2 | 7/2018 | Cook et al. |
| 11,339,216 B2 | 5/2022 | Cook et al. |
| 2009/0202533 A1 | 8/2009 | Baca et al. |
| 2013/0302277 A1 | 11/2013 | Jenkins et al. |
| 2014/0219919 A1 | 8/2014 | Edwards et al. |
| 2017/0174759 A1 | 6/2017 | Cook et al. |

FOREIGN PATENT DOCUMENTS

| | | |
|---|---|---|
| CN | 108210894 A | 6/2018 |
| CN | 108210909 A | 6/2018 |
| JP | 2019-502689 A | 1/2019 |
| WO | WO 1991/019813 A1 | 12/1991 |
| WO | WO 1999/032619 A1 | 7/1999 |
| WO | WO 1999/059608 A2 | 11/1999 |
| WO | WO 2001/029058 A1 | 4/2001 |
| WO | WO 2008/003141 A1 | 1/2008 |
| WO | WO 2009/052588 A1 | 4/2009 |
| WO | WO 2014/121325 A1 | 8/2014 |
| WO | WO 2017/103108 A1 | 6/2017 |
| WO | WO 2018/109168 A1 | 6/2018 |
| WO | WO 2018/109170 A2 | 6/2018 |
| WO | WO 2018/109174 A2 | 6/2018 |
| WO | WO 2019/073057 A1 | 4/2019 |
| WO | WO 2019/207122 A1 | 10/2019 |
| WO | WO 2019/238882 A1 | 12/2019 |
| WO | WO 2019/238884 A1 | 12/2019 |

OTHER PUBLICATIONS

Zager et al., Acute unilateral ischemic renal injury induces progressive renal inflammation, lipid accumulation, histone modification, and "end-stage" kidney disease. Am J Physiol Renal Physiol. Dec. 2011;301(6):F1334-45. doi: 10.1152/ajprenal.00431.2011. Epub Sep. 14, 2011.
Li et al., 4-1BB-mediated Signals Confer Protection Against Folic Acid-Induced Nephrotoxicity. Kidney Blood Press Res. 2012;36(1):10-7. doi: 10.1159/000339022. Epub Jun. 19, 2012.
[No Author Listed], Summary of Recommendation Statements. Kidney International Supplements. 2012;2:8-12. doi:10.1038/kisup.2012.7.
Abbas-Terki et al., Lentiviral-mediated RNA interference. Hum Gene Ther. 2002;13(18):2197-2201.
Aceves et al., Airway fibrosis and angiogenesis due to eosinophil trafficking in chronic asthma. Curr Mol Med. 2008;8(5):350-358. doi:10.2174/156652408785161023.
Almagro et al., Humanization of antibodies. Front Biosci. 2008;13:1619-1633. Published Jan. 1, 2008.
Altenhofer et al., Evolution of NADPH Oxidase Inhibitors: Selectivity and Mechanisms for Target Engagement. Antioxid Redox Signal. Aug. 10, 2015;23(5):406-27. doi: 10.1089/ars.2013.5814.
Arunkumar et al., Science Behind Cisplatin-induced Nephrotoxicity in Humans: A Clinical Study. Asian Pacific journal of Tropical Biomedicine. 2012;2(8):640-644. Epub Aug. 28, 2012.
Augsburger et al., Pharmacological Characterization of the Seven Human NOX Isoforms and their Inhibitors. Redox Biology. 2019;26:1-15. Epub Jul. 11, 2019.
Baeuerle et al., Bispecific T-cell engaging antibodies for cancer therapy. Cancer Res. 2009;69(12):4941-4944.
Barbas et al., In vitro evolution of a neutralizing human antibody to human immunodeficiency virus type 1 to enhance affinity and broaden strain cross-reactivity. Proc Natl Acad Sci U S A. 1994;91(9):3809-3813.
Barton et al., Retroviral delivery of small interfering RNA into primary cells. Proc Natl Acad Sci U S A. 2002;99(23):14943-14945.
Beaucage et al., Advances in the synthesis of Oligonucleotides by the Phosphoramidte Approach. Tetrahedron. 1992;48(12):2223-2311.

(Continued)

*Primary Examiner* — Prema M Mertz
(74) *Attorney, Agent, or Firm* — Wolf, Greenfield & Sacks, P.C.

(57) ABSTRACT

Methods of treating and preventing kidney injury through inhibiting interleukin 11 (IL-11)-mediated signalling are disclosed, as well as agents for use in such methods.

5 Claims, 24 Drawing Sheets

Specification includes a Sequence Listing.

(56) References Cited

OTHER PUBLICATIONS

Bernstein et al., Role for a bidentate ribonuclease in the initiation step of RNA interference. Nature. 2001;409(6818):363-366.

Blanc et al., Monoclonal antibodies against the human interleukin-11 receptor alpha-chain (IL-11Ralpha) and their use in studies of human mononuclear cells. J Immunol Methods. Jul. 31, 2000;241(1-2):43-59.

Bockhorn et al., MicroRNA-30c Inhibits Human Breast Tumour Chemotherapy Resistance by Regulating TWF1 and IL-11. Nat Commun. 2013;4:1393. doi: 10.1038/ncomms2393.

Borkhardt A., Blocking oncogenes in malignant cells by RNA interference—New hope for a highly specific cancer treatment. Cancer Cell. Sep. 2002;2(3):167-168.

Brookes et al., The Essence of SNPs. Gene. Jul. 8, 1999;234(2):177-86. doi: 10.1016/s0378-1119(99)00219-x.

Brüggemann et al., Human Antibody Production in Transgenic Animals. Archivum Immunologiae et Therapiae Experimentalis. Apr. 2015;63(2):101-108. Epub Dec. 3, 2014.

Castanotto et al., The promises and pitfalls of RNA-interference-based therapeutics. Nature. 2009;457(7228):426-433.

Chan et al., The role of phage display in therapeutic antibody discovery. Int Immunol. 2014;26(12):649-657. doi:10.1093/intimm/dxu082.

Chang-Panesso et al., Cellular plasticity in kidney injury and repair. National Reviews Nephrology. Jan. 2017;13:39-46. Supporting Information, 2 pages.

Chothia et al., Canonical Structures for the Hypervariable Regions of Immunoglobulins. Journal of Molecular Biology. 1987;196:901-917.

Ciliberto et al. Cytokine Inhibitors: Chapter 8. Marcel Dekker, Inc. 2001.

Coelho et al., Renal regeneration after acute kidney injury. Nephrology. Mar. 2018;23(9):805-814.

Concepcion et al., Label-free detection of biomolecular interactions using BioLayer interferometry for kinetic characterization. Comb Chem High Throughput Screen. Sep. 2009;12(8):791-800. doi: 10.2174/138620709789104915.

Curtis et al., Recombinant Soluble interleukin-11 (IL-11) Receptor Alpha-Chain Can Act as an IL-11 Antagonist. Blood. Dec. 1, 1997;90(11):4403-12.

Czauderna et al., Structural variations and stabilising modifications of synthetic siRNAs in mammalian cells. Nucleic Acids Res. 2003;31(11):2705-2716.

Davies et al., Human IgG4: a structural perspective. Immunological Reviews. 2015;268:139-159.

De-Chao et al., Soluble Vascular Endothelial Growth Factor Decoy Receptor FP3 Exerts Potent Antiangiogenic Effects. Mol Ther. May 2012;20(5):938-47. doi: 10.1038/mt.2011.285.

Devroe et al., Retrovirus-delivered siRNA. BMC Biotechnol. 2002;2:15. Published Aug. 28, 2002. doi:10.1186/1472-6750-2-15.

Du et al., Interleukin-11: review of molecular, cell biology, and clinical use. Blood. Jun. 1, 1997;89(11):3897-908.

Dzau et al., Gene therapy for cardiovascular disease. Trends Biotechnol. 1993;11(5):205-210.

Elbashir et al., Duplexes of 21-nucleotide RNAs mediate RNA interference in cultured mammalian cells. Nature. 2001;411(6836):494-498.

Elbashir et al., RNA interference is mediated by 21- and 22-nucleotide RNAs. Genes Dev. 2001;15(2):188-200.

Fan et al., Highly Parallel SNP Genotyping. Cold Spring Harb Symp Quant Biol. 2003;68:69-78. doi: 10.1101/sqb.2003.68.69.

Fire et al., Potent and specific genetic interference by double-stranded RNA in Caenorhabditis elegans. Nature. 1998;391(6669):806-811.

Fire, RNA-triggered gene silencing. Trends Genet. 1999;15(9):358-363.

French, How to make bispecific antibodies. Methods Mol Med. 2000;40:333-339.

Garbers et al., Interleukin-6 and interleukin-11: same same but different. Biol Chem. Sep. 2013;394(9):1145-61. doi: 10.1515/hsz-2013-0166.

Gilbert et al., A purpose-synthesised anti-fibrotic agent attenuates experimental kidney diseases in the rat. PLoS One. 2012;7(10):e47160. doi:10.1371/journal.pone.0047160.

Gold et al., Aptamer-based Multiplexed Proteomic Technology for Biomarker Discovery. PLoS One. Dec. 7, 2010;5(12):e15004. doi: 10.1371/journal.pone.0015004.

Grande et al., Snail1-induced partial epithelial-to-mesenchymal transition drives renal fibrosis in mice and can be targeted to reverse established disease. Nature Medicine. Sep. 2015;21(9):989-997, Supplemental Information, 15 pages.

Ham et al., Critical role of interleukin-11 in isoflurane-mediated protection against ischemic acute kidney injury in mice. Anesthesiology. Dec. 2013;119(6):1389-401. doi: 10.1097/ALN.0b013e3182a950da.

Hamilton et al., A species of small antisense RNA in post-transcriptional gene silencing in plants. Science. 1999;286(5441):950-952.

Hammond et al., An RNA-directed nuclease mediates post-transcriptional gene silencing in *Drosophila* cells. Nature. 2000;404(6775):293-296.

Hammond et al., Post-transcriptional gene silencing by double-stranded RNA. Nat Rev Genet. 2001;2(2):110-119.

Hannon et al., RNA interference. Nature. 2002;418(6894):244-251.

Hawkins et al., Selection of phage antibodies by binding affinity. Mimicking affinity maturation. J Mol Biol. 1992;226(3):889-896.

Hearty et al., Measuring antibody-antigen binding kinetics using surface plasmon resonance. Methods Mol Biol. 2012;907:411-42. doi: 10.1007/978-1-61779-974-7_24.

Hermann et al., Important immunoregulatory role of interleukin-11 in the inflammatory process in rheumatoid arthritis. Arthritis Rheum. Aug. 1998;41(8):1388-97.

Hilton et al., Cloning of a Murine IL-11 Receptor Alpha-Chain; Requirement for gp130 for High Affinity Binding and Signal Transduction. EMBO J. Oct. 17, 1994;13(20):4765-75.

Holgate, The airway epithelium is central to the pathogenesis of asthma. Allergol Int. 2008;57(1):1-10. doi:10.2332/allergolint.R-07-154.

Hoogenboom, Selecting and screening recombinant antibody libraries. Nat Biotechnol. 2005;23(9):1105-1116. doi:10.1038/nbt1126.

Hornig et al., Chapter 40: Production of bispecific antibodies: diabodies and tandem scFv. Methods Mol Biol. 2012;907:713-727. doi:10.1007/978-1-61779-974-7_40.

Hurrell, Monoclonal Hybridoma Antibodies: Techniques and Applications. CRC Press. 1982.

Jackson et al., In vitro antibody maturation. Improvement of a high affinity, neutralizing antibody against IL-1 beta. J Immunol. 1995;154(7):3310-3319.

Jerabek-Willemsen et al., Molecular interaction studies using microscale thermophoresis. Assay and Drug Development Technologies. Aug. 2011;9(4):342-353.

Jo et al., MEK inhibitor, U0126, attenuates cisplatin-induced renal injury by decreasing inflammation and apoptosis. Kidney International. Feb. 2005;67(2):458-466.

John et al., Human MicroRNA targets [published correction appears in PLoS Biol. Jul. 2005;3(7):e264]. PLoS Biol. 2004;2(11):e363. doi:10.1371/journal.pbio.0020363.

Karpovich et al., Expression and Function of interleukin-11 and Its Receptor Alpha in the Human Endometrium. Mol Hum Reprod. Feb. 2003;9(2):75-80. doi: 10.1093/molehr/gag012.

Katoh et al., MAFFT Multiple Sequence Alignment Software Version 7: Improvements in Performance and Usability. Molecular Biology and Evolution. Apr. 2013;30(4):772-780. Epub Jan. 16, 2013.

Knight et al., STAT3 in tissue fibrosis: is there a role in the lung ?. Pulm Pharmacol Ther. 2011;24(2):193-198. doi:10.1016/j.pupt.2010.10.005.

Knight et al., The role of gp130/IL-6 cytokines in the development of pulmonary fibrosis: critical determinants of disease susceptibility and progression?. Pharmacol Ther. 2003;99(3):327-338. doi:10.1016/s0163-7258(03)00095-0.

(56) References Cited

OTHER PUBLICATIONS

Konner et al., Use of soluble recombinant decoy receptor vascular endothelial growth factor trap (VEGF Trap) to inhibit vascular endothelial growth factor activity. Clin Colorectal Cancer. 2004;4 Suppl 2:S81-S85.

Kontermann, Dual targeting strategies with bispecific antibodies. MAbs. 2012;4(2):182-197.

Lad et al., High-Throughput Kinetic Screening of Hybridomas to Identify High-Affinity Antibodies Using Bio-Layer Interferometry. Journal of Biomolecular Screening. 2015;20(4):498-507.

Lai et al., Interleukin-11 attenuates nephrotoxic nephritis in Wistar Kyoto rats. J Am Soc Nephrol. Nov. 2001;12(11):2310-20.

Lai et al., Interleukin-11 reduces renal injury and glomerular NF-kappa B activity in murine experimental glomerulonephritis. Nephron Exp Nephrol. 2005;101(4):e146-54. Epub Aug. 30, 2005.

Lassman et al., Kalign—an accurate and fast multiple sequence alignment algorithm. BMC Bioinformatics. Dec. 2005;6(298) https://doi.org/10.1186/1471-2105, 9 pages.

Lay et al., Interleukin 11 Regulates Endometrial Cancer Cell Adhesion and Migration via STAT3. Int J Oncol. Aug. 2012;41(2):759-64. doi: 10.3892/ijo.2012.1486.

Lee et al., Endogenous IL-11 signaling is essential in Th2- and IL-13-induced inflammation and mucus production. Am J Respir Cell Mol Biol. Dec. 2008;39(6):739-46. doi: 10.1165/rcmb.2008-0053OC. Epub Jul. 10, 2008.

Lee et al., Interleukin-11 protects against renal ischemia and reperfusion injury. Am J Physiol Renal Physiol. Oct. 15, 2012; 303(8):F1216-F1224. EPub Aug. 1, 2012. doi: 10.1152/ajprenal.00220.2012.

Lee et al., Transgenic modeling of transforming growth factor-beta(1): role of apoptosis in fibrosis and alveolar remodeling. Proc Am Thorac Soc. 2006;3(5):418-423. doi:10.1513/pats.200602-017AW.

Leng et al., Interleukin-11. Int J Biochem Cell Biol. 1997;29(8-9):1059-1062. doi:10.1016/s1357-2725(97)00017-4.

Lewis et al., Efficient delivery of siRNA for inhibition of gene expression in postnatal mice. Nat Genet. 2002;32(1):107-108.

Lo et al., Antibody Engineering. Microbiol Spectr. 2014;2(1):. doi:10.1128/microbiolspec.AID-0007-12.

Lokau et al., Proteolytic Cleavage Governs Interleukin-11 Trans-signaling. Cell Rep. 2016; 14(7): 1761-1773.

Lori et al., Gene therapy approaches to HIV infection. Am J Pharmacogenomics. 2002;2(4):245-252.

Lovisa et al., Epithelial to Mesenchymal Transition induces cell cycle arrest and parenchymal damage in renal fibrosis. Nat Med. Sep. 2015;21(9):998-1009. Author Manuscript, 32 pages.

Marks et al., By-passing immunization: building high affinity human antibodies by chain shuffling. Biotechnology (N Y). 1992;10(7):779-783.

Martineau P., Affinity Measurements by Competition ELISA. Antibody Engineering. 2010;1:657-665.

Matsuzaki et al., Parallel Genotyping of Over 10,000 SNPs Using a One-Primer Assay on a High-Density Oligonucleotide Array. Genome Res. Mar. 2004;14(3):414-25. doi: 10.1101/gr.2014904.

Matta et al., Use of lentiviral vectors for delivery of small interfering RNA. Cancer Biol Ther. 2003;2(2):206-210.

McCoy et al., IL-11 produced by breast cancer cells augments osteoclastogenesis by sustaining the pool of osteoclast progenitor cells. BMC Cancer. Jan. 11, 2013;13:16. doi: 10.1186/1471-2407-13-16. 11 pages.

McManus et al., Gene silencing in mammals by small interfering RNAs. Nat Rev Genet. 2002;3(10):737-747.

Mehta et al., Acute Kidney Injury Network: report of an initiative to improve outcomes in acute kidney injury. Critical Care. Mar. 2007;11(2):R31. doi: 10.1186/cc5713. 8 pages.

Menkhorst et al., IL11 Antagonist Inhibits Uterine Stromal Differentiation, Causing Pregnancy Failure in Mice. Biol Reprod. May 2009;80(5):920-7. doi: 10.1095/biolreprod.108.073601.

Morris et al., Translocating peptides and proteins and their use for gene delivery. Curr Opin Biotechnol. 2000;11(5):461-466.

Morrison et al., Chimeric human antibody molecules: mouse antigen-binding domains with human constant region domains. Proc Natl Acad Sci U S A. 1984;81(21):6851-6855.

Muller et al., Bispecific antibodies for cancer immunotherapy: Current perspectives. BioDrugs. 2010;24(2):89-98.

Myers et al., Recombinant Dicer efficiently converts large dsRNAs into siRNAs suitable for gene silencing. Nat Biotechnol. 2003;21(3):324-328.

Nandurkar et al., The Human IL-11 Receptor Requires gp130 for Signalling: Demonstration by Molecular Cloning of the Receptor. Oncogene. Feb. 1, 1996;12(3):585-93.

Neuberger et al. Antibody Engineering. 8th International Biotechnology Symposium Part 2. 1988:792-799.

Ng et al., Interleukin-11 Is a Therapeutic Target in Idiopathic Pulmonary Fibrosis. Sci Transl Med. Sep. 25, 2019;11(511):eaaw1237. doi: 10.1126/scitranslmed.aaw1237.

Nordan et al., Purification and NH2-terminal sequence of a plasmacytoma growth factor derived from the murine macrophage cell line P388D1. J Immunol. 1987;139(3):813-817.

Notredame et al., T-Coffee: A Novel Method for Fast and Accurate Multiple Sequence Alignment. Journal of Molecular Biology. 2000;302:205-217.

Nowak, Protein kinase C-alpha and ERK1/2 mediate mitochondrial dysfunction, decreases in active Na+ transport, and cisplatin-induced apoptosis in renal cells. J Biol Chem. Nov. 8, 2002;277(45):43377-88. doi: 10.1074/jbc.M206373200. Epub Sep. 5, 2002.

Oh et al., Cisplatin-induced Kidney Dysfunction and Perspectives on Improving Treatment Strategies. Electrolyte Blood Press. Dec. 2014;12(2):55-65. Epub Dec. 31, 2014.

Olman, Epithelial cell modulation of airway fibrosis in asthma. Am J Respir Cell Mol Biol. 2003;28(2):125-128. doi:10.1165/rcmb.F257.

Ozkok et al., Pathophysiology of Cisplatin-Induced Acute Kidney Injury. BioMed Research International. 2014;2014:967826. doi: 10.1155/2014/967826. Epub Aug. 6, 2014. 17 pages.

Park et al., Monoclonal antibody therapy. Advances in Protein Chemistry. 2001;56:369-421. https://doi.org/10.1016/S0065-3233(01)56010-6.

Pasqualini et al., Targeting the interleukin-11 Receptor ? in Metastatic Prostate Cancer: A First-In-Man Study. Cancer. Jul. 15, 2015;121(14):2411-21. doi: 10.1002/cncr.29344.

Paul et al., Effective expression of small interfering RNA in human cells. Nat Biotechnol. 2002;20(5):505-508.

Pflanz et al., A Fusion Protein of interleukin-11 and Soluble interleukin-11 Receptor Acts as a Superagonist on Cells Expressing gp130. FEBS Lett. Apr. 30, 1999;450(1-2):117-22. doi: 10.1016/s0014-5793(99)00477-9.

Prêle et al., STAT3: a central mediator of pulmonary fibrosis? [published correction appears in Proc Am Thorac Soc. Oct. 2012;9(4):210]. Proc Am Thorac Soc. 2012;9(3):177-182. doi:10.1513/pats.201201-007AW.

Putoczki et al., More Than a Sidekick: The IL-6 Family Cytokine IL-11 Links Inflammation to Cancer. J Leukoc Biol. Dec. 2010;88(6):1109-17. doi: 10.1189/jlb.0410226.

Qin et al., Inhibiting HIV-1 infection in human T cells by lentiviral-mediated delivery of small interfering RNA against CCR5. Proc Natl Acad Sci U S A. 2003; 100(1):183-188.

Rahman et al., Acute Kidney Injury: A Guide to Diagnosis and Management. American Family Physician. Oct. 1, 2012;86(7):631-639.

Retter et al., VBASE2, an integrative V gene database. Nucleic Acids Research. 2005;33:D671-D674.

Reverdatto et al., Peptide Aptamers: Development and Applications. Curr Top Med Chem. 2015;15(12):1082-1101. Author Manuscript, 38 pages.

Rich et al., Extracting kinetic rate constants from surface plasmon resonance array systems. Analytical Biochemistry. 2008;373(1):112-120. Epub Aug. 19, 2007.

Safdari et al., Antibody humanization methods—a review and update. Biotechnol Genet Eng Rev. 2013;29:175-186. doi:10.1080/02648725.2013.801235.

(56) References Cited

OTHER PUBLICATIONS

Schaefer et al., IL-11 is a crucial determinant of cardiovascular fibrosis. Nature. 2017; 552(7683): 110-115.
Scherr et al., Gene silencing mediated by small interfering RNAs in mammalian cells. Curr Med Chem. 2003;10(3):245-256.
Scherr et al., Modulation of gene expression by lentiviral-mediated delivery of small interfering RNA. Cell Cycle. 2003;2(3):251-257.
Schier et al.., Identification of functional and structural amino-acid residues by parsimonious mutagenesis. Gene. 1996;169(2):147-155.
Schroeder et al., Structure and Function of Immunoglobulins. J Allergy Clin Immunol. Feb. 2010;125(202):S41-s52. Author Manuscript, 24 pages.
Segal et al., Production of bispecific antibodies. Curr Protoc Immunol. 2001;Chapter 2:. doi:10.1002/0471142735.im0213s14.
Sharp, RNA interference—2001. Genes Dev. 2001;15(5):485-490.
Shen et al., Gene silencing by adenovirus-delivered siRNA. FEBS Lett. 2003;539(1-3):111-114.
Shin et al., Optimization of linear double-stranded RNA for the production of multiple siRNAs targeting hepatitis C virus. RNA. 2009;15(5):898-910.
Shinagawa et al., Generation of Ski-knockdown mice by expressing a long double-strand RNA from an RNA polymerase II promoter. Genes Dev. 2003;17(11):1340-1345.
Shuey et al., RNAi: gene-silencing in therapeutic intervention. Drug Discov Today. 2002;7(20):1040-1046.
Silver et al., The Economic Consequences of Acute Kidney Injury. Nephron. 2017;137:297-301. Epub Jun. 9, 2017.
Simeoni et al., Insight into the mechanism of the peptide-based gene delivery system MPG: implications for delivery of siRNA into mammalian cells. Nucleic Acids Res. 2003;31(11):2717-2724.
Simon-Tillaux et al., Snail and kidney fibrosis. Nephrol Dial Transplant. 2017;32(2):224-233. doi:10.1093/ndt/gfw333.
Sinha et al., Polymer support oligonucleotide synthesis XVIII: use of b-cyanoethyl-N,N-dialkylamino-/Nmorpholino phosphoramidite of deoxynucleosides for the synthesis of DNA fragments simplifying deprotection and isolation of the final product. Nucleic Acids Research. 1984;12(11):4539-4557.
Song et al., RNA interference targeting Fas protects mice from fulminant hepatitis. Nat Med. 2003;9(3):347-351.
Sorensen et al., Gene silencing by systemic delivery of synthetic siRNAs in adult mice. J Mol Biol. 2003;327(4):761-766.
Stangou et al., Effect of IL-11 on glomerular expression of TGF-beta and extracellular matrix in nephrotoxic nephritis in Wistar Kyoto rats. J Nephrol. Jan.-Feb. 2011;24(1):106-11. Author Manuscript.
Starkel et al., Genetic Factors Predicting Response to Interferon Treatment for Viral Hepatitis C. Gut. Apr. 2008;57(4):440-2. doi: 10.1136/gut.2007.137646.
Söding J., Protein homology detection by HMM-HMM comparison. Bioinformatics. 2005;21(7):951-960. Epub Nov. 5, 2004.
Taki et al., Differential Inhibitory Effects of Indomethacin, Dexamethasone, and Interferon-Gamma (IFN-gamma) on IL-11 Production by Rheumatoid Synovial Cells. Clin Exp Immunol. Apr. 1998;112(1):133-8. doi: 10.1046/j.1365-2249.1998.00552.x.
Tao et al., Cancer-associated fibroblasts treated with cisplatin facilitates chemoresistance of lung adenocarcinoma through IL-11/IL-11R/STAT3 signaling pathway. Sci Rep. Dec. 6, 2016;6:38408. doi: 10.1038/srep38408. 24 pages.
Tuerk et al., Systematic Evolution of Ligands by Exponential Enrichment: RNA Ligands to Bacteriophage T4 DNA Polymerase. Science. Aug. 3, 1990;249(4968):505-10. doi: 10.1126/science.2200121.
Tuschl, RNA interference and small interfering RNAs. Chembiochem. 2001;2(4):239-245.
Underhill-Day et al., Functional Characterization of W147A: A High-Affinity interleukin-11 Antagonist. Endocrinology. Aug. 2003;144(8):3406-14. doi: 10.1210/en.2002-0144.
Wang et al., Delivery of siRNA therapeutics: barriers and carriers. AAPS J. 2010;12(4):492-503.
Wang et al., ERK-mediated suppression of cilia in cisplatin-induced tubular cell apoptosis and acute kidney injury. Biochimica et Biophysica Acta. 2013;1832:1582-1590.
Widjaja et al., IL-11 neutralising therapies target hepatic stellate cell-induced liver inflammation and fibrosis in NASH. bioRxiv. Nov. 14, 2018;470062:34 pages; doi.org/10.1101/470062.
Widjaja et al., Inhibiting Interleukin 11 Signaling Reduces Hepatocyte Death and Liver Fibrosis, Inflammation, and Steatosis in Mouse Models of Nonalcoholic Steatohepatitis. Gastroenterology. Sep. 2019;157(3):777-792.e14. doi: 10.1053/j.gastro.2019.05.002.
Widjaja et al., Redefining Interleukin 11 as a regeneration-limiting hepatotoxin. BioRxiv. Nov. 4, 2019. Retrieved from https://www.biorxiv.org/content/10.1101/830018v.1.full.pdf. 40 pages.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297.
Yang et al., Kidney Regeneration in Mammals. Nephron Experimental Nephrology. 2014;126:50-53. Epub May 19, 2014.
Yao et al., Cisplatin Nephrotoxicity: A Review. The American Journal of the Medical Sciences. Aug. 2007;334(2):115-124.
Yelton et al., Affinity maturation of the BR96 anti-carcinoma antibody by codon-based mutagenesis. J Immunol. 1995;155(4):1994-2004.
Zamore et al., RNAi: double-stranded RNA directs the ATP-dependent cleavage of mRNA at 21 to 23 nucleotide intervals. Cell. 2000;101(1):25-33.
Zola, Monoclonal Antibodies: A Manual of Techniques. CRC Press. 1988.
Zuk et al., Overcoming Translational Barriers in Acute Kidney Injury A Report from an NIDDK Workshop. Clinical Journal of the American Society of Nephrology. Jul. 2018;13:1113-1123.
Widjaja et al., Targeting endogenous kidney regeneration using anti-IL11 therapy in acute and chronic models of kidney disease. Nat Commun. Dec. 5, 2022;13(1):7497. doi: 10.1038/s41467-022-35306-1.

Mice receive X203 (10mg/kg), IgG (10mg/kg) or saline IP from W1 until harvest

TREATMENT OF KIDNEY INJURY

CROSS-REFERENCE TO RELATED APPLICATIONS

This application is a divisional of U.S. patent application Ser. No. 16/798,101, filed Feb. 21, 2020, which claims priority to GB 1902419.9, filed Feb. 22, 2019, the contents and elements of which are herein incorporated by reference for all purposes.

Reference To A Sequence Listing Submitted As A Text File Via EFS-Web

This application contains a Sequence Listing which has been submitted in ASCII format via EFS-Web and is hereby incorporated by reference in its entirety. Said ASCII copy, created on May 23, 2022, is named E060170008US01-SEQ-GJM and is 62,642 bytes in size.

FIELD OF THE INVENTION

The present invention relates to the diagnosis, treatment and prophylaxis of diseases and conditions associated with kidney injury, particularly although not exclusively acute kidney injury.

BACKGROUND TO THE INVENTION

Acute kidney injury (AKI) refers to rapid onset damage to the kidney, notably the tubular epithelial cells. It is often chemically-driven, for example renal damage or injury caused by a medicine, chemical, contrast dye or herbal or dietary supplements. It may also be caused by ischaemia, mechanical or immune factors.

AKI is a common condition and affects up to 10% of patients in hospital (Silver, S. A. & Chertow, G. M. The Economic Consequences of Acute Kidney Injury. Nephron 137, 297-301 (2017)). There is major mortality associated with AKI and mortality in patients requiring intensive care post AKI can be up to 50%. For those surviving AKI there are long-term risks of progressing to chronic kidney disease (CKD), end stage renal failure, renal replacement therapy or transplantation (Silver, S. A. & Chertow, G. M. The Economic Consequences of Acute Kidney Injury. Nephron 137; Mehta, R. L et al. Acute Kidney Injury Network: report of an initiative to improve outcomes in acute kidney injury. Crit. Care 11; Zuk, A. et al. Overcoming Translational Barriers in Acute Kidney Injury: A Report from an NIDDK Workshop. Clin. J. Am. Soc. Nephrol. 13, 1113-1123 (2018)).

The chemotherapeutic agent cisplatin (dichlorodiamino platinum; SP-4-2)-diamminedichloroplatinum(II)) is widely used to treat a range of cancers including head and neck, breast, lung, testis, ovarian, brain, and bladder cancers. After a single dose of cisplatin (50-100 mg/m$^2$) most patients develop a degree of AKI and up to 30% of patients will develop nephrotoxicity (Ozkok, A. & Edelstein, C. L. Pathophysiology of cisplatin-induced acute kidney injury. Biomed Res. Int. 2014, 967826 (2014)), as defined by an abrupt reduction in kidney function signified by an increase in serum creatinine (Mehta et al supra). In elderly patients with head and neck cancer up to 20% will progress from AKI to severe kidney dysfunction (Yao, X., Panichpisal, K., Kurtzman, N. & Nugent, K. Cisplatin nephrotoxicity: a review. Am. J. Med. Sci. 334, 115-124 (2007)). Cisplatin-induced AKI is dose limiting and therapy is often split into multiple doses over several weeks but this is still associated with nephrotoxicity. The severity of cisplatin-induced AKI is more severe in the presence of pre-existing conditions that include diabetes, hypertension, nephrotoxic drugs and old age.

The pathophysiology of AKI is largely defined by damage of the renal tubular epithelial cells (TECs) by toxins, chemicals, drugs, immune and mechanical factors or ischaemia. There are also vascular and immune components to AKI. In patients treated with cisplatin, the drug is present in the kidney at levels up to five times those in the plasma. In the kidney, cisplatin accumulates in TECs where it induces reactive oxygen species, depletes glutathione, causes mitochondrial dysfunction and causes cell death through apoptosis or necrosis (Ozkok et al, supra; Wang, S., Wei, Q., Dong, G. & Dong, Z. ERK-mediated suppression of cilia in cisplatin-induced tubular cell apoptosis and acute kidney injury. Biochim. Biophys. Acta 1832, 1582-1590 (2013); Jo, S.-K., Cho, W. Y., Sung, S. A., Kim, H. K. & Won, N. H. MEK inhibitor, U0126, attenuates cisplatin-induced renal injury by decreasing inflammation and apoptosis. Kidney Int. 67; Nowak, G. Protein Kinase C-α and ERK1/2 Mediate Mitochondrial Dysfunction, Decreases in Active Na+Transport, and Cisplatin-induced Apoptosis in Renal Cells. J. Biol. Chem. 277, 43377-43388 (2002)). During ischemia, TECs that have very high oxygen demands become oxygen deprived and undergo cell death due to apoptosis or necrosis.

Following AKI, kidney function can recover. This is widely recognised as driven by proliferation of remaining TECs, which have very large regenerative capacity (Yang. H.-C., Liu, S.-J. & Fogo, A. B. Kidney regeneration in mammals. Nephron Exp. Nephrol. 126, 50 (2014); Coelho, S., Cabral, G., Lopes, J. A. & Jacinto, A. Renal regeneration after acute kidney injury. Nephrology 23, 805-814 (2018); Chang-Panesso, M. & Humphreys, B. D. Cellular plasticity in kidney injury and repair. Nat. Rev. Nephrol. 13, 39-46 (2017)). When TEC proliferation is inadequate nephrotoxicity develops and over time chronic kidney disease can ensue and fibrosis may occur as a secondary phenomenon. In recent studies it has been shown that a critical determinant of TEC dysfunction following AKI is re-expression of the SNAIL gene (also known as SNA; SNAH; SNAIL; SLUGH2: SNAIL1) (Grande, M. T. et al. Snail1-induced partial epithelial-to-mesenchymal transition drives renal fibrosis in mice and can be targeted to reverse established disease. Nat. Med. 21, 989-997 (2015); Simon-Tillaux, N. & Hertig, A. Snail and kidney fibrosis. Nephrol. Dial. Transplant 32, 224-233 (2017); Lovisa, S. et al. Epithelial-to-mesenchymal transition induces cell cycle arrest and parenchymal damage in renal librosis. Nat. Med. 21, 998-1009 (2015)). SNAIL is important for embryogenesis but is rarely expressed in adults other than in cancers where it causes epithelial to mesenchymal transition (EMT). In the kidney, the TGFβ1 gene can induce SNAIL in TECs and this is associated with impaired TEC function and proliferation (Lovisa, S. et al. Epithelial-to-mesenchymal transition induces cell cycle arrest and parenchymal damage in renal fibrosis. Nat. Med. 21, 998-1009 (2015)).

The cytokine interleukin 11 (IL-11) reportedly has a powerful protective effect against AKI following ischemia-reperfusion injury and inhibits apoptosis, necrosis and inflammation in AKI (Lee, H. T. et al. Interleukin-11 protects against renal ischemia and reperfusion injury. Am. J. Physiol. Renal Physiol. 303, F1216-24 (2012)). IL-11 has also been shown to be upregulated in human TECs and mouse kidney by isoflurane and this is associated with a critical protective role for IL-11 against acute ischemic kidney injury (Ham, A. et al. Critical role of interleukin-11 in isoflurane-mediated protection against ischemic acute kidney injury in mice. *Anesthesiology* 119, 1389-1401 (2013)).

IL-11 treatment has also been reported to protect against acute nephrotoxic nephritis in rats and mice by reducing kidney inflammation and preventing kidney damage (Stangou, M. et al. Effect of IL-11 on glomerular expression of TGF-beta and extracellular matrix in nephrotoxic nephritis in Wistar Kyoto rats. *J. Nephrol.* 24, 106-111 (2011): Lai, P. C. et al. Interleukin-11 attenuates nephrotoxic nephritis in Wistar Kyoto rats. *J. Am. Soc. Nephrol.* 12, 2310-2320 (2001); Lai, P. C. et al. Interleukin-11 reduces renal injury and glomerular NF-kappa B activity in murine experimental glomerulonephritis. *Nephron Exp. Nephrol.* 101, e146-54 (2005)).

SUMMARY OF THE INVENTION

In contrast to the reported protective role of IL-11 in kidney injury and damage, the present invention relates to the treatment and/or prevention of kidney injury and disorders, diseases or conditions associated with kidney injury through the inhibition of IL-11 signalling.

In one aspect of the present invention there is provided an agent capable of inhibiting interleukin 11 (IL-11)-mediated signalling for use in a method of treating or preventing kidney injury and/or a disorder, disease or condition associated with kidney injury.

In another aspect of the present invention, there is provided the use of an agent capable of inhibiting interleukin 11 (IL-11)-mediated signalling for use in the manufacture of a medicament for use in a method of treating or preventing kidney injury and/or a disorder, disease or condition associated with kidney injury.

In another aspect of the present invention, there is provided a method of treating or preventing kidney injury and/or a disorder, disease or condition associated with kidney injury, the method comprising administering to a subject in need of treatment a therapeutically effective amount of an agent capable of inhibiting interleukin 11 (IL-11)-mediated signalling.

The present invention also provides an agent capable of inhibiting interleukin 11 (IL-11)-mediated signalling for use in a method of reversing kidney injury.

Also provided is the use of an agent capable of inhibiting interleukin 11 (IL-11)-mediated signalling for use in the manufacture of a medicament for use in a method of reversing kidney injury.

Also provided is a method of reversing kidney injury, the method comprising administering to a subject in need of treatment a therapeutically effective amount of an agent capable of inhibiting interleukin 11 (IL-11)-mediated signalling.

In some embodiments, the kidney injury is acute kidney injury. In some embodiments, the kidney injury is nephrotoxicity. In some embodiments, the kidney injury is drug-induced kidney injury or ischemia-induced kidney injury. In some embodiments, the kidney injury is cisplatin-induced kidney injury or cisplatin-induced nephrotoxicity. In some embodiments, the kidney injury is characterised by damage to tubular epithelial cells (TECs).

The present invention also provides an agent capable of inhibiting interleukin 11 (IL-11)-mediated signalling for use in a method of improving renal function in a subject suffering from an impairment to renal function.

Also provided is the use of an agent capable of inhibiting interleukin 11 (IL-11)-mediated signalling for use in the manufacture of a medicament for use in a method of improving renal function in a subject suffering from an impairment to renal function.

Also provided is a method of improving renal function in a subject suffering from an impairment to renal function, the method comprising administering to a subject in need of treatment a therapeutically effective amount of an agent capable of inhibiting interleukin 11 (IL-11)-mediated signalling.

The present invention also provides an agent capable of inhibiting interleukin 11 (IL-11)-mediated signalling for use in a method of promoting the proliferation, survival and/or function of tubular epithelial cells (TECs), and/or the growth, maintenance and/or function of renal tissue (e.g. following kidney injury).

Also provided is the use of an agent capable of inhibiting interleukin 11 (IL-11)-mediated signalling for use in the manufacture of a medicament for use in a method of promoting the proliferation, survival and/or function of tubular epithelial cells (TECs), and/or the growth, maintenance and/or function of renal tissue (e.g. following kidney injury).

Also provided is a method of promoting the proliferation, survival and/or function of tubular epithelial cells (TECs), and/or the growth, maintenance and/or function of renal tissue (e.g. following kidney injury), the method comprising administering to a subject in need of treatment a therapeutically effective amount of an agent capable of inhibiting interleukin 11 (IL-11)-mediated signalling.

The present invention also provides an agent capable of inhibiting interleukin 11 (IL-11)-mediated signalling for use in a method of inhibiting SNAIL expression (e.g. following kidney injury).

Also provided is the use of an agent capable of inhibiting interleukin 11 (IL-11)-mediated signalling for use in the manufacture of a medicament for use in a method of inhibiting SNAIL expression (e.g. following kidney injury).

Also provided is a method of inhibiting SNAIL expression (e.g. following kidney injury), the method comprising administering to a subject in need of treatment a therapeutically effective amount of an agent capable of inhibiting interleukin 11 (IL-11)-mediated signalling.

The present invention also provides an agent capable of inhibiting interleukin 11 (IL-11)-mediated signalling for use in a method of inhibiting or reversing the transition of tubular epithelial cells (TECs) to a mesenchymal cell-like phenotype (e.g. following kidney injury).

Also provided is the use of an agent capable of inhibiting interleukin 11 (IL-11)-mediated signalling for use in the manufacture of a medicament for use in a method of inhibiting or reversing the transition of tubular epithelial cells (TECs) to a mesenchymal cell-like phenotype (e.g. following kidney injury).

Also provided is a method of inhibiting or reversing the transition of tubular epithelial cells (TECs) to a mesenchymal cell-like phenotype (e.g. following kidney injury), the method comprising administering to a subject in need of treatment a therapeutically effective amount of an agent capable of inhibiting interleukin 11 (IL-11)-mediated signalling.

In some embodiments in accordance with various aspects of the present invention, the agent is an agent capable of preventing or reducing the binding of interleukin 11 (IL-11) to a receptor for interleukin 11 (IL-11R).

In some embodiments, the agent is capable of binding to interleukin 11 (IL-11) or a receptor for interleukin 11 (IL-11R). In some embodiments, the agent is selected from the group consisting of: an antibody or an antigen-binding fragment thereof, a polypeptide, a peptide, a nucleic acid, an oligonucleotide, an aptamer or a small molecule. The agent may be an antibody or an antigen-binding fragment thereof. The agent may be a decoy receptor.

In some embodiments, the agent is an anti-IL-11 antibody antagonist of IL-11-mediated signalling, or an antigen-binding fragment thereof.

In some embodiments, the antibody or antigen-binding fragment comprises:
(i) a heavy chain variable (VH) region incorporating the following CDRs:
 HC-CDR1 having the amino acid sequence of SEQ ID NO:34
 HC-CDR2 having the amino acid sequence of SEQ ID NO:35
 HC-CDR3 having the amino acid sequence of SEQ ID NO:36; and
(ii) a light chain variable (VL) region incorporating the following CDRs:
 LC-CDR1 having the amino acid sequence of SEQ ID NO:37
 LC-CDR2 having the amino acid sequence of SEQ ID NO:38
 LC-CDR3 having the amino acid sequence of SEQ ID NO:39.

In some embodiments, the antibody or antigen-binding fragment comprises:
(i) a heavy chain variable (VH) region incorporating the following CDRs:
 HC-CDR1 having the amino acid sequence of SEQ ID NO:40
 HC-CDR2 having the amino acid sequence of SEQ ID NO:41
 HC-CDR3 having the amino acid sequence of SEQ ID NO:42; and
(ii) a light chain variable (VL) region incorporating the following CDRs:
 LC-CDR1 having the amino acid sequence of SEQ ID NO:43
 LC-CDR2 having the amino acid sequence of SEQ ID NO:44
 LC-CDR3 having the amino acid sequence of SEQ ID NO:45.

In some embodiments, the agent is an anti-IL-11Rα antibody antagonist of IL-11-mediated signalling, or an antigen-binding fragment thereof.

In some embodiments, the antibody or antigen-binding fragment comprises:
(i) a heavy chain variable (VH) region incorporating the following CDRs:
 HC-CDR1 having the amino acid sequence of SEQ ID NO:46
 HC-CDR2 having the amino acid sequence of SEQ ID NO:47
 HC-CDR3 having the amino acid sequence of SEQ ID NO:48; and
(ii) a light chain variable (VL) region incorporating the following CDRs:
 LC-CDR1 having the amino acid sequence of SEQ ID NO:49
 LC-CDR2 having the amino acid sequence of SEQ ID NO:50
 LC-CDR3 having the amino acid sequence of SEQ ID NO:51.

In some embodiments, the agent is a decoy receptor for IL-11. In some embodiments the decoy receptor for IL-11 comprises: (i) an amino acid sequence corresponding to the cytokine binding module of gp130 and (ii) an amino acid sequence corresponding to the cytokine binding module of IL-11Rα.

In some embodiments the agent is an IL-11 mutein. In some embodiments the IL-11 mutein is W147A.

In some embodiments, the agent is capable of preventing or reducing the expression of interleukin 11 (IL-11) or a receptor for interleukin 11 (IL-11R). The agent may be an oligonucleotide or a small molecule.

In some embodiments the agent is an antisense oligonucleotide capable of preventing or reducing the expression of IL-11. In some embodiments the antisense oligonucleotide capable of preventing or reducing the expression of IL-11 is siRNA targeted to IL11 comprising the sequence of SEQ ID NO:12, 13, 14 or 15.

In some embodiments the agent is an antisense oligonucleotide capable of preventing or reducing the expression of IL-11Rα. In some embodiments the antisense oligonucleotide capable of preventing or reducing the expression of IL-11Rα is siRNA targeted to IL11RA comprising the sequence of SEQ ID NO:16, 17, 18 or 19.

In any embodiments provided herein, the interleukin 11 receptor may be or comprise IL-11Rα.

In any embodiments provided herein, the kidney injury may be one of acute kidney injury (AKI), nephrotoxicity, drug-induced kidney injury (DIKI), acute kidney failure, acute kidney disease, chronic kidney disease, kidney damage, tubular necrosis, acute tubular necrosis, and autoimmune kidney injury.

In any embodiments provided herein, the agent may be administered before, in conjunction with, or after the cause of the kidney injury, e.g. administration or consumption of a nephrotoxic medicine or exposure to a physical, mechanical, chemical or environmental source of kidney injury.

In some embodiments, the agents, uses and methods herein are provided for treating and/or preventing drug-induced kidney injury (DIKI). The DIKI may be intrinsic and/or idiosyncratic kidney injury. In any embodiments, the agents, uses and methods herein may be provided for treating and/or preventing cisplatin-induced kidney injury and/or cisplatin-induced nephrotoxicity.

In some embodiments, the agents, uses and methods herein may be provided for treating and/or preventing ischemia-induced kidney injury (IIKI) or ischemia-induced acute kidney injury.

In any embodiments provided herein, the disorder, disease or condition associated with kidney injury may be a disease, disorder or condition in which kidney injury is pathologically implicated. The pathology may include damage to tubular epithelial cells and/or the transition of TECs to a mesenchymal cell-like phenotype, which may be proximal and/or distal.

In any embodiments, the method comprises administering the agent to a subject in which expression of interleukin 11 (IL-11) or a receptor for IL-11 (IL-11R) may be upregulated.

In any embodiments, the method may comprise administering the agent to a subject in which expression of interleukin 11 (IL-11) or a receptor for interleukin 11 (IL-11R) has been determined to be upregulated.

In some embodiments the method comprises determining whether expression of interleukin 11 (IL-11) or a receptor for IL-11 (IL-11R) is upregulated in the subject and administering the agent to a subject in which expression of interleukin 11 (IL-11) or a receptor for IL-11 (IL-11R) is upregulated.

Also provided is a method of determining the suitability of a subject for the treatment or prevention of kidney injury and/or a disorder, disease or condition associated with kidney injury with an agent capable of inhibiting interleukin 11 (IL-11)-mediated signalling, the method comprising determining, optionally in vitro, whether interleukin 11 (IL-11) or a receptor for IL-11 (IL-11R) expression is upregulated in the subject.

Also provided is a method of selecting a subject for the treatment or prevention of kidney injury and/or a disorder, disease or condition associated with kidney injury with an agent capable of inhibiting interleukin 11 (IL-11)-mediated signalling, the method comprising determining, optionally in vitro, whether interleukin 11 (IL-11) or a receptor for IL-11 (IL-11R) expression is upregulated in the subject.

In one aspect there is provided a method of diagnosing kidney injury and/or a disorder, disease or condition associated with kidney injury, or a risk of developing kidney injury and/or a disorder, disease or condition associated with kidney injury in a subject, the method comprising determining, optionally in vitro, the upregulation of interleukin 11 (IL-11) or an receptor for IL-11 (IL-11R) in a sample obtained from the subject. In some embodiments, the method of diagnosing is a method of confirming a diagnosis of kidney injury and/or a disorder, disease or condition associated with kidney injury in a subject suspected of having kidney injury and/or a disorder, disease or condition associated with kidney injury. In some embodiments a method of diagnosing and/or a method of confirming a diagnosis comprises selecting the subject for treatment with an agent capable of inhibiting interleukin 11 (IL-11)-mediated signalling.

Also provided is a method of providing a prognosis for a subject having, or suspected of having, kidney injury and/or a disorder, disease or condition associated with kidney injury, the method comprising determining, optionally in vitro, whether expression of interleukin 11 (IL-11) or a receptor for IL-11 (IL-11R) is upregulated in a sample obtained from the subject and, based on the determination, providing a prognosis for treatment of the subject with an agent capable of inhibiting interleukin 11 (IL-11)-mediated signalling. In some embodiments, a method of providing a prognosis comprises selecting a subject determined to have upregulated expression of interleukin 11 (IL-11) or a receptor for IL-11 (IL-11R) for treatment with an agent capable of inhibiting interleukin 11 (IL-11)-mediated signalling.

In another aspect there is provided a method of diagnosing kidney injury and/or a disorder, disease or condition associated with kidney injury or a risk of developing kidney injury and/or a disorder, disease or condition associated with kidney injury, the method comprising determining, optionally in vitro, one or more genetic factors in the subject that are predictive of upregulation of expression of IL-11 or a receptor for IL-11, or of upregulation of IL-11 mediated signalling. In some embodiments the method comprises selecting the subject for treatment with an agent capable of inhibiting interleukin 11 (IL-11)-mediated signalling.

Also provided is a method of providing a prognosis for a subject having, or suspected of having, kidney injury and/or a disorder, disease or condition associated with kidney injury, the method comprising determining, optionally in vitro, one or more genetic factors in the subject that are predictive of upregulation of expression of IL-11 or a receptor for IL-11, or of upregulation of IL-11 mediated signalling.

DESCRIPTION

There is ongoing demand for effective prevention and treatment of kidney injury, particularly acute kidney injury.

The cytokine IL-11 has been reported to have a protective effect against acute kidney injury following ischemia-reperfusion injury (Lee et al supra) and IL-11 has been reported to be upregulated and protective in human tubular epithelial cells and mouse kidney upon chemical damage by isoflurane (Ham et al supra).

In contrast, however, the present inventors have found that inhibition of IL-11 mediated signalling is effective to protect tubular epithelial cells, allowing them to proliferate and recover from damage that is a common causative factor of acute kidney injury. Whilst not wishing to be bound by theory, the inventors believe that inhibition of IL-11 enables tubular epithelial cells to proliferate leading to renal tissue regeneration and recovery by preventing or reducing the expression of SNAIL.

Interleukin 11 and Receptors for IL-11

Interleukin 11 (IL-11), also known as adipogenesis inhibitory factor, is a pleiotropic cytokine and a member of the IL-6 family of cytokines that includes IL-6, IL-11, IL-27, IL-31, oncostatin, leukemia inhibitory factor (LIF), cardiotrophin-1 (CT-1), cardiotrophin-like cytokine (CLC), ciliary neurotrophic factor (CNTF) and neuropoetin (NP-1).

Interleukin 11 (IL-11) is expressed in a variety of mesenchymal cell types. IL-11 genomic sequences have been mapped onto chromosome 19 and the centromeric region of chromosome 7, and is transcribed with a canonical signal peptide that ensures efficient secretion from cells. The activator protein complex of IL-11, cJun/AP-1, located within its promoter sequence is critical for basal transcriptional regulation of IL-11 (Du and Williams., Blood 1997, Vol 89: 3897-3908). The immature form of human IL-11 is a 199 amino acid polypeptide whereas the mature form of IL-11 encodes a protein of 178 amino acid residues (Garbers and Scheller., Biol. Chem. 2013; 394(9):1145-1161). The human IL-11 amino acid sequence is available under UniProt accession no. P20809 (P20809.1 GI:124294; SEQ ID NO:1). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species. In preferred embodiments the species is human (*Homo sapiens*). Isoforms, fragments, variants or homologues of an IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature IL-11 from a given species, e.g. human. Isoforms, fragments, variants or homologues of an IL-11 may optionally be characterised by ability to bind IL-11Rα (preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80). A fragment of IL-11 may be of any length (by number of amino acids), although may optionally be at least 25% of the length of mature IL-11 and may have a maximum length of one of 50%, 75%, 80%, 85%, 90%, 91%, 92%, 93%, 94%, 95%, 96%, 97%, 98%, or 99% of the length of mature IL-11. A fragment of IL-11 may have a minimum length of 10 amino acids, and a maximum length of one of 15, 20, 25, 30, 40, 50, 60, 70, 80, 90, 100, 110, 120, 130, 140, 150, 160, 170, 180, 190 or 195 amino acids.

IL-11 signals through a homodimer of the ubiquitously expressed glycoprotein 130 (gp130; also known as glycoprotein 130, IL-6ST, IL-6-beta or CD130). Gp130 is a transmembrane protein that forms one subunit of the type I cytokine receptor with the IL-6 receptor family. Specificity is gained through an individual interleukin 11 receptor subunit alpha (IL-11Rα), which does not directly participate in signal transduction, although the initial cytokine binding event to the α-receptor leads to the final complex formation with gp130.

Human gp130 (including the 22 amino acid signal peptide) is a 918 amino acid protein, and the mature form is 866 amino acids, comprising a 597 amino acid extracellular domain, a 22 amino acid transmembrane domain, and a 277 amino acid intracellular domain. The extracellular domain of the protein comprises the cytokine-binding module (CBM) of gp130. The CBM of gp130 comprises the Ig-like domain D1, and the fibronectin-type III domains D2 and D3 of gp130. The amino acid sequence of human gp130 is available under UniProt accession no. P40189-1 (SEQ ID NO:2).

Human IL-11Rα is a 422 amino acid polypeptide (UniProt 014626; SEQ ID NO:3) and shares ~85% nucleotide and amino acid sequence identity with the murine IL-11Rα. Two isoforms of IL-11Rα have been reported, which differ in the cytoplasmic domain (Du and Williams, supra). The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain (34 amino acids) lacks the Box 1 and 2 regions that are required for activation of the JAK/STAT signalling pathway.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In this specification a receptor for IL-11 (IL-11R) refers to a polypeptide or polypeptide complex capable of binding IL-11. In some embodiments an IL-11 receptor is capable of binding IL-11 and inducing signal transduction in cells expressing the receptor.

An IL-11 receptor may be from any species and includes isoforms, fragments, variants or homologues of an IL-11 receptor from any species. In preferred embodiments the species is human (*Homo sapiens*).

In some embodiments the IL-11 receptor may be IL-11Rα. In some embodiments a receptor for IL-11 may be a polypeptide complex comprising IL-11Rα. In some embodiments the IL-11 receptor may be a polypeptide complex comprising IL-11Rα and gp130. In some embodiments the IL-11 receptor may be gp130 or a complex comprising gp130 to which IL-11 binds.

Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing the IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99%, of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

IL-11 Signalling

IL-11 binds to IL-11Rα with low affinity (Kd ~10 nmol/L), and interaction between these binding partners alone is insufficient to transduce a biological signal. The generation of a high affinity receptor (Kd ~400 to 800 pmol/L) capable of signal transduction requires co-expression of the IL-11Rα and gp130 (Curtis et al Blood 1997; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and downstream signalling, predominantly through the mitogen-activated protein kinase (MAPK)-cascade and the Janus kinase/signal transducer and activator of transcription (Jak/STAT) pathway (Garbers and Scheller, supra).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11R) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R. Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be important for disease pathogenesis, yet its role in human disease has not yet been studied. In preferred embodiments, inhibition of IL-11-mediated signalling is achieved by disrupting IL-11-mediated cis signalling.

As used herein. 'IL-11 trans signalling' is used to refer to signalling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα, termed "IL-11 cis signalling".

IL-11-mediated signalling has been shown to stimulate hematopoiesis and thrombopoiesis, stimulate osteoclast activity, stimulate neurogenesis, inhibit adipogenesis, reduce pro inflammatory cytokine expression, modulate extracellular matrix (ECM) metabolism, and mediate normal growth control of gastrointestinal epithelial cells (Du and Williams, supra).

The physiological role of Interleukin 11 (IL-11) remains unclear. IL-11 has been most strongly linked with activation of haematopoietic cells and with platelet production. IL-11 has also been shown to confer protection against graft-vs-host-disease, inflammatory arthritis and inflammatory bowel disease, leading to IL-11 being considered an anti-inflammatory cytokine (Putoczki and Ernst, J Leukoc Biol 2010, 88(6):1109-1117). However, it is suggested that IL-11 is pro-inflammatory as well as anti-inflammatory, pro-angiogenic and important for neoplasia. Recent studies have shown that IL-11 is readily detectable during viral-induced inflammation in a mouse arthritis model and in cancers, suggesting that the expression of IL-11 can be induced by pathological stimuli. IL-11 is also linked to Stat3-dependent activation of tumour-promoting target genes in neoplastic gastrointestinal epithelium (Putoczki and Ernst, supra).

As used herein, "IL-11 signalling" and "IL-11-mediated signalling" refers to signalling mediated by binding of IL-11, or a fragment thereof having the function of the mature IL-11 molecule, to a receptor for IL-11. It will be appreciated that "IL-11 signalling" and "IL-11 mediated signalling" refer to signalling initiated by IL-11/functional fragment thereof, e.g. through binding to a receptor for IL-11. "Signalling" in turn refers to signal transduction and other cellular processes governing cellular activity.

Kidney Injury

Aspects of the present invention relate to the diagnosis, treatment and prophylaxis of kidney injury, particularly acute kidney injury (AKI; also known as acute renal failure) and/or kidney injury, e.g. AKI.

Herein, 'kidney injury' refers to damage to the kidney, renal tissue, and/or one or more renal cells. Damage to a cell/tissue/organ may result from insult to the cell/tissue/organ, e.g. chemical or physical treatment/experience. In some embodiments kidney injury may be a consequence of chemical insult, e.g. in the case of drug-induced kidney injury, e.g. cisplatin-induced kidney injury. In some embodiments kidney injury may arise from physical insult, e.g. in the case of kidney injury arising as a result of crush, or kidney injury as a result of surgical damage to renal tissue, which may occur e.g. during surgery to treat a disease and/or for kidney transplantation (e.g. the kidney injury may have iatrogenic causes). In some embodiments kidney injury may be a consequence of hypoxia, e.g. as a consequence of ischaemia, or may result from reperfusion. In some embodiments kidney injury may arise from infection, immune response to infection, cancer and/or autoimmunity. Damage may be reversible or irreversible.

In some embodiments, kidney injury comprises damage to one or both of the kidneys. In some embodiments kidney injury comprises damage to one or more of a renal capsule, renal cortex, renal medulla, renal papilla, renal pyramid, renal column, renal calyx, minor calyx, major calyx, hilum, renal pelvis, ureter, renal artery and a renal vein. In some embodiments kidney injury comprises damage to one or more of a renal epithelial cell, a tubule epithelial cell, a proximal tubule epithelial cell, a distal tubule epithelial cell, a renal parietal cell, a podocyte, a loop of Henle thin segment cell, a thick ascending limb cell, a collecting duct principal cell, a collecting duct intercalated cell, and an interstitial kidney cell. In some embodiments, kidney injury comprises damage to a renal epithelial cell, e.g. a tubule epithelial cell, e.g. proximal tubule epithelial cell.

Damage to a cell/tissue/organ may be characterised by a change to the structure and/or function of the cell/tissue/organ. For example, damage to a cell/tissue/organ may be characterised by a reduction in the level of a correlate of normal function of the cell/tissue/organ, and/or an increase in a correlate of impaired function of the cell/tissue/organ. By way of illustration, damage to the kidney/renal tissue/renal cells may be characterised by a reduction in urine output by the subject experiencing kidney damage, and/or an increase in serum creatine levels in the subject experiencing kidney damage. Damage to a cell/tissue/organ may be characterised by cell death, e.g. death of cells of the damaged organ/tissue. The cell death may result from apoptosis (i.e. programmed cell death) or necrosis (premature cell death as a consequence of damage).

As used herein, 'acute kidney injury' generally refers to abrupt deterioration in kidney function. Acute kidney injury may be characterised by a rapid increase serum creatinine and/or a rapid reduction in urine output.

Acute kidney injury may be defined and staged in accordance with the Summary of Recommendation Statements of the Kidney Disease Improving Global Outcomes (KDIGO) group, Kidney International Supplements (2012) 2, 8-12 (hereby incorporated by reference in its entirety).

In some embodiments, acute kidney injury is defined as: (i) an increase in serum creatine by $\geq 0.3$ mg/dl ($\geq 26.5$ μmol/l) within a 48 hour period; (ii) an increase in serum creatine to $\geq 1.5$ times baseline which is known or presumed to have occurred within the previous 7 days: or (iii) urine volume of <0.5 ml/kg/h for 6 hours.

In some embodiments, the acute kidney injury may be stage 1, 2 or 3 acute kidney injury. Stage 1 acute kidney injury may be defined as: (i) an increase in serum creatine to 1.5-1.9 times baseline, (ii) an increase in serum creatine to $\geq 0.3$ mg/dl ($\geq 26.5$ μmol/l), or (iii) urine volume of <0.5 ml/kg/h for 6-12 hours. Stage 2 acute kidney injury may be defined as: (i) an increase in serum creatine to 2.0-2.9 times baseline, or (ii) urine volume of <0.5 ml/kg/h for $\geq 12$ hours. Stage 3 acute kidney injury may be defined as: (i) an increase in serum creatine to $\geq 3.0$ times baseline, (ii) an increase in serum creatine to $\geq 4.0$ mg/dl ($\geq 353.6$ μmol/l), (iii) initiation of renal replacement therapy, (iv) in pateints <18 years, decrease in eGFR to <35 ml/min per 1.73 $m^2$; (v) urine volume of <0.3 mV/kg/h for $\geq 24$ hours, or (vi) anuria for $\geq 12$ hours.

Kidney injury may be characterised by damage to tubular epithelial cells (TECs) and/or the transition of TECs to an epithelial-to-mesenchymal cell-like phenotype (i.e. EMT). Transition of TECs to a mesenchymal cell-like phenotype may be characterised e.g. by reduced expression of E-cadherin, increased expression of SNAIL and/or increased expression of ACTA2.

The kidney injury may have any cause, examples include kidney injury resulting from mechanical (i.e. physical) damage or injury, chemical damage or injury, ischemia or genetic predisposition. The cause or damage will normally result in impaired kidney function, which may lead to kidney failure.

Mechanical damage or injury may include physical injury to the subject, to the kidney, to TECs or to podocytes. It may also include tubular obstruction/blockage, e.g. of the urinary tract.

Chemical damage or injury may be caused by a drug, medicine, toxin, herbal or dietary supplements or other chemical agent administered to, absorbed or ingested by the subject. In some embodiments the chemical damage is a side effect of the administration of such an agent to treat a disease or condition not occurring in the kidney, or occurring both in the kidney and in one or more other tissues. In some embodiments the chemical damage is a side effect of administration of a chemotherapeutic agent administered to the subject in order to prevent or treat cancer. In some embodiments the kidney injury is drug-induced kidney injury or drug-induced acute kidney injury. In some embodiments, tubular obstruction/blockage, e.g. of the urinary tract, may arise as the result of administration of certain chemical agents, e.g. sulphonamides, methotrexate, acyclovir, diethylene glycol, triamterene.

Ischemic damage may arise from a decrease in blood flow to the kidney which may be caused by a number of factors such as low blood pressure e.g. due to sepsis, blood loss or surgery, or the effect of a chemical agent, e.g. a medicine or drug, administered to the subject to treat another disease, disorder or condition. Kidney injury caused by ischemia may be ischemia-induced kidney injury, or ischemia-induced acute kidney injury. Kidney injury caused by crush injury may be ischemia-induced kidney injury with vasoconstriction or can be caused by tubular cast mechanical factors or toxic effects of circulating factors e.g. myoglobin.

In some embodiments the kidney injury, which may be AKI, is characterised by damage to, which may in some cases include or lead to death of, tubular epithelial cells (TECs) of the kidney, i.e. renal tubular epithelial cells. The TECs may be proximal or distal, both of which may be damaged in AKI, as may also the podocytes in the kidney glomerulus. Damage to TECs may also be any type of damage, injury or insult, e.g. as described above this may be mechanical, chemical or ischemic damage. Damage to TECs is a common causative factor of kidney injury, particularly AKI. Proliferation of TECs provides a mechanism for recovery and restoration of kidney function, whereas failure of TECs to proliferate can lead to disease development and progression, e.g. to chronic kidney disease and renal failure. Proliferation of podocyte precursors to restore glomerulus function may also occur, but is not as well described as TEC proliferation.

In some embodiments the kidney injury is, or is characterised by, nephrotoxicity. As used herein, nephrotoxicity refers to toxicity to the kidneys. Toxicity in turn refers to damage, e.g. as described herein. Nephrotoxicity can arise as a result of toxic effects of certain substances on renal function, and may therefore be viewed as a consequence of chemical damage or injury. As with chemical damage or injury, nephrotoxicity may be a side effect of the administration of an agent to treat a disease or condition not occurring in the kidney, or occurring both in the kidney and in one or more other tissues. In some embodiments nephrotoxicity may be a side effect of administration of a chemotherapeutic agent administered to the subject in order to prevent or treat cancer. As such, nephrotoxicity may be a form of drug-induced kidney injury or drug-induced acute kidney injury.

As described above, drug-induced kidney injury, drug-induced acute kidney injury or drug-induced nephrotoxicity may arise as a side effect of the administration of a drug or medicine intended to treat a disease, disorder or condition occurring in tissues outside the kidney, within the kidney or both. A number of drugs are known to exhibit such side-effects, which may depend on the condition being treated, the subject being treated, the dosage amount, dosage regime or mode of administration, and the extent to which the subject exhibits partial kidney failure prior to treatment. For example, the following agents have all been reported to have potential in inducing kidney injury: diuretics, n-blockers, vasodilators, ACE inhibitors, aminoglycoside antibiotics (e.g. gentamicin), amphotericin B, cisplatin, NSAIDs (e.g. aspirin, ibuprofen, diclofenac), ciclosporin, lithium salts, cyclophosphamide, sulphonamides, methotrexate, acyclovir, diethylene glycol, triamterene, β-lactam antibiotics, vancomycin, rilampicin, ciprofloxacin, ranitidine, cimetidine, furosemide, thiazides, phenytoin. Optionally a drug-induced kidney injury is not a folate-induced kidney injury.

In some embodiments, a drug-induced kidney injury, drug-induced acute kidney injury or drug-induced nephrotoxicity may arise as a side effect of the administration of a chemotherapeutic agent intended to treat or prevent cancer in the subject. Examples of chemotherapeutic agents include alkylating agents such as cisplatin, carboplatin, mechlorethamine, cyclophosphamide, chlorambucil, ifosfamide; purine or pyrimidine anti-metabolites such as azathiopurine or mercaptopurine; alkaloids and terpenoids, such as vinca alkaloids (e.g. vincristine, vinblastine, vinorelbine, vindesine), podophyllotoxin, etoposide, teniposide, taxanes such as paclitaxel (Taxol™), docetaxel; topoisomerase inhibitors such as the type I topoisomerase inhibitors camptothecins irinotecan and topotecan, or the type II topoisomerase inhibitors amsacrine, etoposide, etoposide phosphate, teniposide; antitumor antibiotics (e.g. anthracycline antibiotics) such as dactinomycin, doxorubicin (Adriamycin™), epirubicin, bleomycin, rapamycin; antibody based agents, such as anti-VEGF, anti-TNFα, anti-IL-2, antiGpIIb/IIIa, anti-CD-52, anti-CD20, anti-RSV, anti-HER2/neu (erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab; and EGFR inhibitors such as erlotinib, cetuximab, gefitinib.

In some preferred embodiments, the present invention concerns the diagnosis, treatment and/or prophylaxis of cisplatin-induced kidney injury. This may include cisplatin-induced acute kidney injury or cisplatin-induced nephrotoxicity. Cisplatin (dichlorodiamino platinum; SP-4-2)-diamminedichloroplatinum(II)) is a chemotherapeutic agent that is widely used to treat a range of cancers including head and neck, breast, lung, testis, ovarian, brain, and bladder cancers and is widely acknowledged to lead to kidney injury and dysfunction involving tubular damage and necrosis (e.g. Oh et al., Electrolyte Blood Press 2014 December; 12(2): 55-65; P A Arunkumar et al., Asian Pac J Trop Biomed 2012 Aug. 2(8): 640-644). Other platinum-based chemotherapeutics agents also cause kidney damage.

Whilst it is recognised that a subject having kidney injury may also present with fibrosis of the kidney, either as a disease condition having a separable etiology or as a secondary effect of the kidney injury, in some embodiments the kidney injury being diagnosed, treated or prevented is not fibrosis of the kidney, e.g. renal fibrosis. In some embodiments the subject does not have fibrosis. In some embodiments TEC damage occurs in the absence of fibrosis. In some embodiments fibrosis arises separately (e.g. secondarily to) AKI, e.g. due to incomplete regeneration of TECs. In some embodiments, the damaged TECs in the subject are not pro-fibrotic TECs. In some embodiments, fibrosis does not arise.

Agents Capable of Inhibiting the Action of IL-11

Aspects of the present invention involve inhibition of IL-11-mediated signalling.

Herein, 'inhibition' refers to a reduction, decrease or lessening relative to a control condition. For example, inhibition of the action of IL-11 by an agent capable of inhibiting IL-11-mediated signalling refers to a reduction, decrease or lessening of the extent/degree of IL-11-mediated signalling in the absence of the agent, and/or in the presence of an appropriate control agent.

Inhibition may herein also be referred to as neutralisation or antagonism. That is, an agent capable of inhibiting IL-11-mediated signalling (e.g. interaction, signalling or other activity mediated by IL-11 or an IL-11-containing complex) may be said to be a 'neutralising' or 'antagonist' agent with respect to the relevant function or process. For example, an agent which is capable of inhibiting IL-11-mediated signalling may be referred to as an agent which is capable of neutralising IL-11-mediated signalling, or may be referred to as an antagonist of IL-11-mediated signalling.

The IL-11 signalling pathway offers multiple routes for inhibition of IL-11 signalling. An agent capable of inhibiting IL-11-mediated signalling may do so e.g. through inhibiting the action of one or more factors involved in, or necessary for, signalling through a receptor for IL-11.

For example, inhibition of IL-11 signalling may be achieved by disrupting interaction between IL-11 (or an IL-11 containing complex, e.g. a complex of IL-11 and IL-11Rα) and a receptor for IL-11 (e.g. IL-11Rα, a receptor complex comprising IL-11Rα, gp130 or a receptor complex comprising IL-11Rα and gp130). In some embodiments, inhibition of IL-11-mediated signalling is achieved by inhibiting the gene or protein expression of one or more of e.g. IL-11, IL-11Rα and gp130.

In embodiments, inhibition of IL-11-mediated signalling is achieved by disrupting IL-11-mediated cis signalling but not disrupting IL-11-mediated trans signalling, e.g. inhibition of IL-11-mediated signalling is achieved by inhibiting gp130-mediated cis complexes involving membrane bound IL-11Rα. In embodiments, inhibition of IL-11-mediated signalling is achieved by disrupting IL-11-mediated trans signalling but not disrupting IL-11-mediated cis signalling, i.e. inhibition of IL-11-mediated signalling is achieved by inhibiting gp130-mediated trans signalling complexes such as IL-11 bound to soluble IL-11Rα or IL-6 bound to soluble IL-6R. In embodiments, inhibition of IL-11-mediated signalling is achieved by disrupting IL-11-mediated cis signalling and IL-11-mediated trans signalling. Any agent as described herein may be used to inhibit IL-11-mediated cis and/or trans signalling.

In other examples, inhibition of IL-11 signalling may be achieved by disrupting signalling pathways downstream of IL-11/IL-11Rα/gp130. That is, in some embodiments inhibition/antagonism of IL-11-mediated signalling comprises inhibition of a signalling pathway/process/factor downstream of signalling through the IL-11/IL-11 receptor complex.

In some embodiments inhibition/antagonism of IL-11-mediated signalling comprises inhibition of signalling through an intracellular signalling pathway which is activated by the IL-11/IL-11 receptor complex. In some embodiments inhibition/antagonism of IL-11-mediated signalling comprises inhibition of one or more factors whose expression/activity is upregulated as a consequence of signalling through the IL-11/IL-11 receptor complex.

In some embodiments, the methods of the present invention employ agents capable of inhibiting JAK/STAT signalling. In some embodiments, agents capable of inhibiting JAK/STAT signalling are capable of inhibiting the action of JAK1, JAK2, JAK3, TYK2, STAT1, STAT2, STAT3, STAT4, STAT5A, STAT5B and/or STAT6. For example, agents may be capable of inhibiting activation of JAK/STAT proteins, inhibiting interaction of JAK or STAT proteins with cell surface receptors e.g. IL-11Rα or gp130, inhibiting phosphorylation of JAK proteins, inhibiting interaction between JAK and STAT proteins, inhibiting phosphorylation of STAT proteins, inhibiting dimerization of STAT proteins, inhibiting translocation of STAT proteins to the cell nucleus, inhibiting binding of STAT proteins to DNA, and/or promoting degradation of JAK and/or STAT proteins. In some embodiments, a JAK/STAT inhibitor is selected from Ruxolitinib (Jakafi/Jakavi; Incyte), Tofacitinib (Xeljanz/Jakvinus; NIH/Pfizer), Oclacitinib (Apoquel), Baricitinib (Olumiant; Incyte/Eli Lilly), Filgotinib (G-146034/GLPG-0634; Galapagos Nev.), Gandotinib (LY-2784544; Eli Lilly), Lestaurtinib (CEP-701; Teva), Momelotinib (GS-0387/CYT-387; Gilead Sciences), Pacritinib (SB1518; CTI), PF-04965842 (Pfizer), Upadacitinib (ABT-494; AbbVie), Peficitinib (ASP015K/JNJ-54781532; Astellas), Fedratinib (SAR302503; Celgene), Cucurbitacin I (JSI-124) and CHZ868.

In some embodiments, the methods of the present invention employ agents capable of inhibiting MAPK/ERK signalling. In some embodiments, agents capable of inhibiting MAPK/ERK signalling are capable of inhibiting the action of GRB2, inhibiting the action of RAF kinase, inhibiting the action of MEK proteins, inhibiting the activation of MAP3K/MAP2K/MAPK and/or Myc, and/or inhibiting the phosphorylation of STAT proteins. In some embodiments, agents capable of inhibiting ERK signalling are capable of inhibiting ERK p42/44. In some embodiments, an ERK inhibitor is selected from SCH772984, SC1, VX-11e, DEL-22379, Sorafenib (Nexavar; Bayer/Onyx), SB590885, PLX4720, XL281, RAF265 (Novartis), encorafenib (LGX818/Braftovi; Array BioPharma), dabrafenib (Tafinlar; GSK), vemurafenib (Zelboraf; Roche), cobimetinib (Cotellic; Roche), CI-1040, PD0325901, Binimetinib (MEK162/MEKTOVI; Array BioPharma), selumetinib (AZD6244; Array/AstraZeneca) and Trametinib (GSK1120212/Mekinist; Novartis). In some embodiments, the methods of the present invention employ agents capable of inhibiting c-Jun N-terminal kinase (JNK) signalling/activity. In some embodiments, agents capable of inhibiting JNK signalling/activity are capable of inhibiting the action and/or phosphorylation of a JNK (e.g. JNK1, JNK2). In some embodiments, a JNK inhibitor is selected from SP600125, CEP 1347. TCS JNK 6o, c-JUN peptide, SU3327, AEG 3482, TCS JNK 5a, B178D3, IQ3, SR3576, IQ1S, JIP-1 (153-163) and CC401 dihydrochloride.

Widjaja et al., bioRxiv (2019) 830018 demonstrates that NOX4 expression and activity is upregulated by signalling through IL-11/IL-11Rα/gp130. NOX4 is an NADPH oxidase, and a source of reactive oxygen species (ROS). Expression of Nox4 is upregulated in transgenic mice with hepatocyte-specific Il11 expression, and primary human hepatocytes stimulated with IL11 upregulate NOX4 expression.

In some embodiments, the present invention employs agents capable of inhibiting NOX4 expression (gene or protein expression) or function. In some embodiments, the present invention employs agents capable of inhibiting IL-11-mediated upregulation of NOX4 expression/function. Agents capable of inhibiting NOX4 expression or function may be referred to herein as NOX4 inhibitors. For example, a NOX4 inhibitor may be capable of reducing expression (e.g. gene and/or protein expression) of NOX4, reducing the level of RNA encoding NOX4, reduce the level of NOX4 protein, and/or reducing the level of a NOX4 activity (e.g. reducing NOX4-mediated NADPH oxidase activity and/or NOX4-mediated ROS production).

NOX4 inhibitors include a NOX4-binding molecules and molecules capable of reducing NOX4 expression. NOX4-binding inhibitors include peptide/nucleic acid aptamers, antibodies (and antibody fragments) and fragments of interaction partners for NOX4 which behave as antagonists of NOX4 function, and small molecules inhibitors of NOX4. Molecules capable of reducing NOX4 expression include antisense RNA (e.g. siRNA, shRNA) to NOX4. In some embodiments, a NOX4 inhibitor is selected from a NOX4 inhibitor described in Altenhofer et al., Antioxid Redox Signal. (2015) 23(5): 406-427 or Augsburder et al., Redox Biol. (2019) 26: 101272, such as GKT137831.

Binding Agents

In some embodiments, agents capable of inhibiting IL-11-mediated signalling may bind to IL-11. In some embodiments, agents capable of inhibiting IL-11-mediated signalling may bind to a receptor for IL-11 (e.g. IL-11Rα, gp130, or a complex containing IL-11Rα and/or gp130). Binding of such agents may inhibit IL-11-mediated signalling by reducing/preventing the ability of IL-11 to bind to receptors for IL-11, thereby inhibiting downstream signalling. Binding of such agents may inhibit IL-11 mediated cis and/or trans-signalling by reducing/preventing the ability of IL-11 to bind to receptors for IL-11, e.g. IL-11Rα and/or gp130, thereby inhibiting downstream signalling. Agents may bind to trans-signalling complexes such as IL-11 and soluble IL-11Rα and inhibit gp130-mediated signalling.

Agents capable of binding to IL-11/an IL-11 containing complex or a receptor for IL-11 may be of any kind, but in some embodiments the agent may be an antibody, an antigen-binding fragment thereof, a polypeptide, a peptide, a nucleic acid, an oligonucleotide, an aptamer or a small molecule. The agents may be provided in isolated or purified form, or may be formulated as a pharmaceutical composition or medicament.

Antibodies and Antigen-Binding Fragments

In some embodiments, an agent capable of binding to IL-11/an IL-11 containing complex or a receptor for IL-11 is an antibody, or an antigen-binding fragment thereof. In some embodiments, an agent capable of binding to IL-11/an IL-11 containing complex or a receptor for IL-11 is a polypeptide, e.g. a decoy receptor molecule. In some embodiments, an agent capable of binding to IL-11/an IL-11 containing complex or a receptor for IL-11 may be an aptamer.

In some embodiments, an agent capable of binding to IL-11/an IL-11 containing complex or a receptor for IL-11 is an antibody, or an antigen-binding fragment thereof. An "antibody" is used herein in the broadest sense, and encompasses monoclonal antibodies, polyclonal antibodies, monospecific and multispecific antibodies (e.g., bispecific antibodies), and antibody fragments, as long as they display binding to the relevant target molecule.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799). Monoclonal antibodies (mAbs) are particularly useful in the methods of the invention, and are a homogenous population of antibodies specifically targeting a single epitope on an antigen.

Polyclonal antibodies are also useful in the methods of the invention. Monospecilic polyclonal antibodies are preferred. Suitable polyclonal antibodies can be prepared using methods well known in the art.

Antigen-binding fragments of antibodies, such as Fab and Fab2 fragments may also be used/provided as can genetically engineered antibodies and antibody fragments. The variable heavy (VH) and variable light (VL) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sd. USA* 81, 6851-6855).

Antibodies and antigen-binding fragments according to the present disclosure comprise the complementarity-determining regions (CDRs) of an antibody which is capable of binding to the relevant target molecule (i.e. IL-11/an IL-11 containing complex/a receptor for IL-11).

Antibodies capable of binding to IL-11 include e.g. monoclonal mouse anti-human IL-11 antibody clone #22626; Catalog No. MAB218 (R&D Systems, MN, USA), used e.g. in Bockhorn et al. *Nat. Commun.* (2013) 4(0):1393, clone 6D9A (Abbiotec), clone KT8 (Abbiotec), clone M3103F11 (BioLegend), clone 1F1 (Abnova Corporation), clone 3C6 (Abnova Corporation), clone GF1 (LifeSpan Biosciences), clone 13455 (Source BioScience), 11h3/19.6.1 (Hermann et al., Arthritis Rheum. (1998) 41(8):1388-97), AB-218-NA (R&D Systems), X203 (Ng et al., Sci Transl Med. (2019) 11(511) pii: eaaw1237, which is also published as Ng, et al., "IL-11 is a therapeutic target in idiopathic pulmonary fibrosis." bioRxiv 336537; doi: https://doi.org/10.1101/336537) and anti-IL-11 antibodies disclosed in US 2009/0202533 A1, WO 99/59608 A2, WO 2018/109174 A2 and WO 2019/238882 A1.

In particular, anti-IL-11 antibody clone 22626 (also known as MAB218) has been shown to be an antagonist of IL-11 mediated signalling, e.g. in Schaefer et al., Nature (2017) 552(7683):110-115. Monoclonal antibody 11h3/19.6.1 is disclosed in Hermann et al., Arthritis Rheum. (1998) 41(8):1388-97 to be a neutralising anti-IL-11 IgG1. AB-218-NA from R&D Systems, used e.g. in McCoy et al., BMC Cancer (2013) 13:16, is another example of neutralizing anti-IL-11 antibody. WO 2018/109174 A2 and WO 2019/238882 A1 disclose yet further exemplary anti-IL-11 antibody antagonists of IL-11 mediated signalling. X203 (also referred to as Enx203) disclosed in Ng, et al., "IL-11 is a therapeutic target in idiopathic pulmonary fibrosis." bioRxiv 336537; doi: https://doi.org/10.1101/336537 and WO 2019/238882 A1 is an anti-IL-11 antibody antagonist of IL-11-mediated signalling, and comprises the VH region according to SEQ ID NO:92 of WO 2019/238882 A1 (SEQ ID NO:22 of the present disclosure), and the VL region according to SEQ ID NO:94 of WO 2019/238882 A1 (SEQ ID NO:23 of the present disclosure). Humanised versions of the X203 are described in WO 2019/238882 A1, including hEnx203 which comprises the VH region according to SEQ ID NO: 17 of WO 2019/238882 A1 (SEQ ID NO:30 of the present disclosure), and the VL region according to SEQ ID NO:122 of WO 2019/238882 A1 (SEQ ID NO:31 of the present disclosure). Enx108A is a further example of an anti-IL-11 antibody antagonist of IL-11-mediated signalling, and comprises the VH region according to SEQ ID NO:8 of WO 2019/238882 A1 (SEQ ID NO:26 of the present disclosure), and the VL region according to SEQ ID NO:20 of WO 2019/238882 A1 (SEQ ID NO:27 of the present disclosure).

Antibodies capable of binding to IL-11Rα include e.g. monoclonal antibody clone 025 (Sino Biological), clone EPR5446 (Abcam), clone 473143 (R & D Systems), clones 8E2, 8D10 and 8E4 and the affinity-matured variants of 8E2 described in US 2014/0219919 A1, the monoclonal antibodies described in Blanc et al (*J. Immunol Methods.* 2000 Jul. 31; 241(1-2); 43-59), X209 (Widjaja et al., Gastroenterology (2019) 157(3):777-792, which is also published as Widjaja, et al., "IL-11 neutralising therapies target hepatic stellate cell-induced liver inflammation and fibrosis in NASH." bioRxiv 470062; doi: https://doi.org/10.1101/470062) antibodies disclosed in WO 2014121325 A1 and US 2013/0302277 A1, and anti-IL-11Rα antibodies disclosed in US 2009/0202533 A1, WO 99/59608 A2, WO 2018/109170 A2 and WO 2019/238884 A1.

In particular, anti-IL-11Rα antibody clone 473143 (also known as MAB1977) has been shown to be an antagonist of IL-11 mediated signalling, e.g. in Schaefer et al., Nature (2017) 552(7683):110-115. US 2014/0219919 A1 provides sequences for anti-human IL-11Rα antibody clones 8E2, 8D10 and 8E4, and discloses their ability to antagonise IL-11 mediated signalling—see e.g. [0489] to [0490] of US 2014/0219919 A1. US 2014/0219919 A1 moreover provides sequence information for an additional 62 affinity-matured variants of clone 8E2, 61 of which are disclosed to antagonise IL-11 mediated signalling—see Table 3 of US 2014/0219919 A1. WO 2018/109170 A2 and WO 2019/238884 A1 disclose yet further exemplary anti-IL-11Rα antibody antagonists of IL-11 mediated signalling. X209 (also referred to as Enx209) disclosed in Widjaja, et al., "IL-11 neutralising therapies target hepatic stellate cell-induced liver inflammation and fibrosis in NASH." bioRxiv 470062; doi: https://doi.org/i0.1101/470062 and WO 2019/238884 A1 is an anti-IL-11Rα antibody antagonist of IL-11-mediated signalling, and comprises the VH region according to SEQ ID NO:7 of WO 2019/238884 A1 (SEQ ID NO:24 of the present disclosure), and the VL region according to SEQ ID NO:14 of WO 2019/238884 A1 (SEQ ID NO:25 of the present disclosure). Humanised versions of the X209 are described in WO 2019/238884 A1, including hEnx209 which comprises the VH region according to SEQ ID NO:1 of WO 2019/238884 A1 (SEQ ID NO:32 of the present disclosure), and the VL region according to SEQ ID NO:17 of WO 2019/238884 A1 (SEQ ID NO:33 of the present disclosure).

The skilled person is well aware of techniques for producing antibodies suitable for therapeutic use in a given species/subject. For example, procedures for producing antibodies suitable for therapeutic use in humans are described in Park and Smolen Advances in Protein Chemistry (2001) 56: 369-421 (hereby incorporated by reference in its entirely).

Antibodies to a given target protein (e.g. IL-11 or IL-11Rα) can be raised in model species (e.g. rodents, lagomorphs), and subsequently engineered in order to improve their suitability for therapeutic use in a given species/subject. For example, one or more amino acids of monoclonal antibodies raised by immunisation of model species can be substituted to arrive at an antibody sequence which is more similar to human germline immunoglobulin sequences (thereby reducing the potential for anti-xenogenic antibody immune responses in the human subject treated with the antibody). Modifications in the antibody variable domains may focus on the framework regions in order to preserve the antibody paratope. Antibody humanisation is a matter of routine practice in the art of antibody technology, and is reviewed e.g. in Almagro and Fransson, Frontiers in Bioscience (2008) 13:1619-1633, Safdari et al., Biotechnology and Genetic Engineering Reviews (2013) 29(2): 175-186 and Lo et al., Microbiology Spectrum (2014) 2(1), all of which are hereby incorporated by reference in their entirety. The requirement for humanisation can be circumvented by raising antibodies to a given target protein (e.g. IL-11 or IL-11Rα) in transgenic model species expressing human immunoglobulin genes, such that the antibodies raised in such animals are fully-human (described e.g. in Brüggemann et al., Arch Immunol Ther Exp (Warsz) (2015) 63(2): 101-108, which is hereby incorporated by reference in its entirety).

Phage display techniques may also be employed to the identification of antibodies to a given target protein (e.g. IL-11 or IL-11Rα), and are well known to the skilled person. The use of phage display for the identification of fully human antibodies to human target proteins is reviewed e.g. in Hoogenboom, Nat. Biotechnol. (2005) 23, 1105-1116 and Chan et al., International Immunology (2014) 26(12): 649-657, which are hereby incorporated by reference in their entirety.

The antibodies/fragments may be antagonist antibodies/fragments that inhibit or reduce a biological activity of IL-11. The antibodies/fragments may be neutralising antibodies that neutralise the biological effect of IL-11, e.g. its ability to stimulate productive signalling via an IL-11 receptor. Neutralising activity may be measured by ability to neutralise IL-11 induced proliferation in the T11 mouse plasmacytoma cell line (Nordan, R. P. et al. (1987) J. Immunol. 139:813).

IL-11- or IL-11Rα-binding antibodies can be evaluated for the ability to antagonise IL-11-mediated signalling, e.g. using the assay described in US 2014/0219919 A1 or Blanc et al (J. Immunol Methods. 2000 Jul. 31; 241(1-2); 43-59. Briefly, IL-11- and IL-11Rα-binding antibodies can be evaluated in vitro for the ability to inhibit proliferation of Ba/F3 cells expressing IL-11Rα and gp130 from the appropriate species, in response to stimulation with IL-11 from the appropriate species. Alternatively, IL-11- and IL-11Rα-binding antibodies can be analysed in vitro for the ability to inhibit the fibroblast-to-myofibroblast transition following stimulation of fibroblasts with TGFβ1, by evaluation of αSMA expression (as described e.g. in WO 2018/109174 A2 (Example 6) and WO 2018/109170 A2 (Example 6), Ng et al., Sci Transl Med. (2019) 11(511) pii: eaaw1237 and Widjaja et al., Gastroenterology (2019) 157(3):777-792).

Antibodies generally comprise six CDRs; three in the light chain variable region (VL): LC-CDR1, LC-CDR2, LC-CDR3, and three in the heavy chain variable region (VH): HC-CDR1, HC-CDR2 and HC-CDR3. The six CDRs together define the paratope of the antibody, which is the part of the antibody which binds to the target molecule. The VH region and VL region comprise framework regions (FRs) either side of each CDR, which provide a scaffold for the CDRs. From N-terminus to C-terminus, VH regions comprise the following structure: N term-[HC-FR1]-[HC-CDR1]-[HC-FR2]-[HC-CDR2]-[HC-FR3]-[HC-CDR3]-[HC-FR4]-C term; and VL regions comprise the following structure: N term-[LC-FR1]-[LC-CDR1]-[LC-FR2]-[LC-CDR2]-[LC-FR3]-[LC-CDR3]-[LC-FR4]-C term.

There are several different conventions for defining antibody CDRs and FRs, such as those described in Kabat et al., Sequences of Proteins of Immunological Interest, 5th Ed. Public Health Service, National Institutes of Health, Bethesda, MD (1991), Chothia et al., *J. Mol. Biol.* 196:901-917 (1987), and VBASE2, as described in Retter et al., *Nucl. Acids Res.* (2005) 33 (suppl 1): D671-D674. The CDRs and FRs of the VH regions and VL regions of the antibodies described herein are defined according to the Kabat system.

In some embodiments an antibody, or an antigen-binding fragment thereof, according to the present disclosure is derived from an antibody which binds specifically to IL-11 (e.g. Enx108A, Enx203 or hEnx203). In some embodiments an antibody, or an antigen-binding fragment thereof, according to the present disclosure is derived from an antibody which binds specifically to IL-11Rα (e.g. Enx209 or hEnx209).

Antibodies and antigen-binding fragments according to the present disclosure preferably inhibit IL-11-mediated signalling. Such antibodies/antigen-binding fragments may be described as being antagonists of IL-11-mediated signalling, and/or may be described as having the ability to neutralise IL-11-mediated signalling.

In some embodiments, the antibody/antigen-binding fragment comprises the CDRs of an antibody which binds to IL-11. In some embodiments the antibody/antigen-binding fragment comprises the CDRs of, or CDRs derived from, the CDRs of an IL-11-binding antibody described herein (e.g. Enx108A, Enx203 or hEnx203).

In some embodiments the antibody/antigen-binding fragment comprises a VH region incorporating the following CDRs:

(1)
HC-CDR1 having the amino acid sequence of SEQ ID NO:34
HC-CDR2 having the amino acid sequence of SEQ ID NO:35
HC-CDR3 having the amino acid sequence of SEQ ID NO:36,
or a variant thereof in which one or two or three amino acids in one or more of HC-CDR1, HC-CDR2, or HC-CDR3 are substituted with another amino acid.

In some embodiments the antibody/antigen-binding fragment comprises a VL region incorporating the following CDRs:

(2)
LC-CDR1 having the amino acid sequence of SEQ ID NO:37
LC-CDR2 having the amino acid sequence of SEQ ID NO:38
LC-CDR3 having the amino acid sequence of SEQ ID NO:39,
or a variant thereof in which one or two or three amino acids in one or more of LC-CDR1. LC-CDR2, or LC-CDR3 are substituted with another amino acid.

In some embodiments the antibody/antigen-binding fragment comprises a VH region incorporating the following CDRs:

(3)
HC-CDR1 having the amino acid sequence of SEQ ID NO:40
HC-CDR2 having the amino acid sequence of SEQ ID NO:41
HC-CDR3 having the amino acid sequence of SEQ ID NO:42.
or a variant thereof in which one or two or three amino acids in one or more of HC-CDR1, HC-CDR2, or HC-CDR3 are substituted with another amino acid.

In some embodiments the antibody/antigen-binding fragment comprises a VL region incorporating the following CDRs:

(4)
LC-CDR1 having the amino acid sequence of SEQ ID NO:43
LC-CDR2 having the amino acid sequence of SEQ ID NO:44
LC-CDR3 having the amino acid sequence of SEQ ID NO:45,
or a variant thereof in which one or two or three amino acids in one or more of LC-CDR1. LC-CDR2, or LC-CDR3 are substituted with another amino acid.

In some embodiments the antibody/antigen-binding fragment comprises a VH region incorporating the CDRs according to (1), and a VL region incorporating the CDRs according to (2). In some embodiments the antibody/antigen-binding fragment comprises a VH region incorporating the CDRs according to (3), and a VL region incorporating the CDRs according to (4).

In some embodiments the antibody/antigen-binding fragment comprises the VH region and the VL region of an antibody which binds to IL-11. In some embodiments the antibody/antigen-binding fragment comprises the VH region and VL region of, or a VH region and VL region derived from, the VH region and VL region of an IL-11-binding antibody described herein (e.g. Enx108A, Enx203 or hEnx203).

In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:26. In some embodiments the antibody/antigen-binding fragment comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:27. In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:26 and a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:27.

In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97/c, 98%, 99%, or 100%, sequence identity to the amino acid sequence of SEQ ID NO:22. In some embodiments the antibody/antigen-binding fragment comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:23. In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:22 and a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:23.

In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:30. In some embodiments the antibody/antigen-binding fragment comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:31. In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:30 and a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:31.

In some embodiments, the antibody/antigen-binding fragment comprises the CDRs of an antibody which binds to IL-11Rα. In some embodiments the antibody/antigen-binding fragment comprises the CDRs of, or CDRs derived from, the CDRs of an IL-11Rα-binding antibody described herein (e.g. Enx209 or hEnx209).

In some embodiments the antibody/antigen-binding fragment comprises a VH region incorporating the following CDRs:

(5)
HC-CDR1 having the amino acid sequence of SEQ ID NO:46
HC-CDR2 having the amino acid sequence of SEQ ID NO:47
HC-CDR3 having the amino acid sequence of SEQ ID NO:48,
or a variant thereof in which one or two or three amino acids in one or more of HC-CDR1, HC-CDR2, or HC-CDR3 are substituted with another amino acid.

In some embodiments the antibody/antigen-binding fragment comprises a VL region incorporating the following CDRs:

(6)
LC-CDR1 having the amino acid sequence of SEQ ID NO:49
LC-CDR2 having the amino acid sequence of SEQ ID NO:50
LC-CDR3 having the amino acid sequence of SEQ ID NO:51,
or a variant thereof in which one or two or three amino acids in one or more of LC-CDR1, LC-CDR2, or LC-CDR3 are substituted with another amino acid.

In some embodiments the antibody/antigen-binding fragment comprises a VH region incorporating the CDRs according to (5), and a VL region incorporating the CDRs according to (6).

In some embodiments the antibody/antigen-binding fragment comprises the VH region and the VL region of an antibody which binds to IL-11Rα. In some embodiments the antibody/antigen-binding fragment comprises the VH region and VL region of, or a VH region and VL region derived from, the VH region and VL region of an IL-11Rα-binding antibody described herein (e.g. Enx209 or hEnx209).

In embodiments in accordance with the present invention in which one or more amino acids of a reference amino acid sequence (e.g. a CDR sequence, VH region sequence or VL region sequence described herein) are substituted with another amino acid, the substitutions may conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. target binding) of the antibody/fragment comprising the substitution relative to the equivalent unsubstituted molecule.

In some embodiments, substitution(s) relative to a reference VH region or VL region sequence may be focused in a particular region or regions of the VH region or VL region sequence. For example, variation from a reference VH region or VL region sequence may be focused in one or more of the framework regions (FR1, FR2, FR3 and/or FR4).

Antibodies and antigen-binding fragments according to the present disclosure may be designed and prepared using the sequences of monoclonal antibodies (mAbs) capable of binding to the relevant target molecule. Antigen-binding regions of antibodies, such as single chain variable fragment (scFv), Fab and Fab2 fragments may also be used/provided. An 'antigen-binding region' or 'antigen binding fragment' is any fragment of an antibody which is capable of binding to the target for which the given antibody is specific.

In some embodiments the antibodies/fragments comprise the VL and VH regions of an antibody which is capable of binding to IL-11, an IL-11 containing complex, or a receptor for IL-11. The VL and VH region of an antigen-binding region of an antibody together constitute the Fv region. In some embodiments the antibodies/fragments comprise or consist of the Fv region of an antibody which is capable of binding to IL-11, an IL-11 containing complex, or a receptor for IL-11. The Fv region may be expressed as a single chain wherein the VH and VL regions are covalently linked, e.g. by a flexible oligopeptide. Accordingly, antibodies/fragments may comprise or consist of an scFv comprising the VL and VH regions of an antibody which is capable of binding to IL-11, an IL-11 containing complex, or a receptor for IL-11.

The VL and light chain constant (CL) region, and the VH region and heavy chain constant 1 (CH1) region of an antigen-binding region of an antibody together constitute the Fab region. In some embodiments the antibodies/fragments comprise or consist of the Fab region of an antibody which is capable of binding to IL-11, an IL-11 containing complex, or a receptor for IL-11.

In some embodiments, antibodies/fragments comprise, or consist of, whole antibody capable of binding to IL-11, an IL-11 containing complex, or a receptor for IL-11. A "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety. Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprises a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments the antibody/antigen-binding fragment of the present disclosure comprises an immunoglobulin heavy chain constant sequence. In some embodiments, an immunoglobulin heavy chain constant sequence may be a human immunoglobulin heavy chain constant sequence. In some embodiments the immunoglobulin heavy chain constant sequence is, or is derived from, the heavy chain constant sequence of an IgG (e.g. IgG1, IgG2, IgG3, IgG4), IgA (e.g. IgA1, IgA2), IgD, IgE or IgM, e.g. a human IgG (e.g. hIgG1, hIgG2, hIgG3, hIgG4), hIgA (e.g. hIgA1, hIgA2), hIgD, hIgE or hIgM. In some the immunoglobulin heavy chain constant sequence is, or is derived from, the heavy chain constant sequence of a human IgG1 allotype (e.g. G1m1, G1m2, G1m3 or G1m17).

In some embodiments the immunoglobulin heavy chain constant sequence is, or is derived from, the constant region sequence of human immunoglobulin G 1 constant (IGHG1; UniProt: P01857-1, v1). In some embodiments the immunoglobulin heavy chain constant sequence is, or is derived from, the constant region sequence of human immunoglobulin G 1 constant (IGHG1: UniProt: P01857-1, v1) comprising substitutions K214R, D356E and L358M (i.e. the G1m3 allotype). In some embodiments the antibody/antigen-binding fragment comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:52.

In some embodiments the immunoglobulin heavy chain constant sequence is, or is derived from, the constant region sequence of human immunoglobulin G 4 constant (IGHG4; UniProt: P01861, v1). In some embodiments the immunoglobulin heavy chain constant sequence is, or is derived from, the constant region sequence of human immunoglobulin G 4 constant (IGHG4; UniProt: P01861, v1) comprising substitutions S241P and/or L248E. The S241P mutation is hinge stabilising while the L248E mutation further reduces the already low ADCC effector function of IgG4 (Davies and Sutton, Immunol Rev. 2015 November; 268(1):139-159; Angal et al Mol Immunol. 1993 January; 30(1):105-8). In some embodiments the antibody/antigen-binding fragment comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:53.

In some embodiments the antibody/antigen-binding fragment of the present disclosure comprises an immunoglobulin light chain constant sequence. In some embodiments, an immunoglobulin light chain constant sequence may be a human immunoglobulin light chain constant sequence. In some embodiments the immunoglobulin light chain constant sequence is, or is derived from, a kappa (κ) or lambda (λ) light chain, e.g. human immunoglobulin kappa constant (IGKC; Cκ; UniProt: P01834-1, v2), or human immunoglobulin lambda constant (IGLC; Cλ), e.g. IGLC1 (UniProt: P0CG04-1, v1), IGLC2 (UniProt: P0DOY2-1, v1), IGLC3 (UniProt: P0DOY3-1, v1), IGLC6 (UniProt: P0CF74-1, v1) or IGLC7 (UniProt: A0M8Q6-1, v3).

In some embodiments the antibody/antigen-binding fragment comprises an immunoglobulin light chain constant sequence. In some embodiments the immunoglobulin light chain constant sequence is, or is derived from human immunoglobulin kappa constant (IGKC; Cκ; UniProt: P01834-1, v2; SEQ ID NO:90). In some embodiments the immunoglobulin light chain constant sequence is a human immunoglobulin lambda constant (IGLC; Cλ), e.g. IGLC1, IGLC2, IGLC3, IGLC6 or IGLC7. In some embodiments the antibody/antigen-binding fragment comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:54. In some embodiments the antibody/antigen-binding fragment comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:55.

In some embodiments, the antibody/antigen-binding fragment comprises: (i) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:28, and (ii) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO-29.

In some embodiments, the antibody/antigen-binding fragment comprises: (i) a polypeptide comprising or consisting of an amino acid sequence having at least 70%, preferably one of 75%, 80%, 85%, 90%$_6$, 91%, 92%, 93%, 94%, 95%, 96%, 97%, 98%, 99% or 100% amino acid sequence identity to the amino acid sequence of SEQ ID NO:56, and (ii) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:57.

In some embodiments, the antibody/antigen-binding fragment comprises: (i) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:58, and (ii) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:59.

Fab, Fv, ScFv and dAb antibody fragments can all be expressed in and secreted from *E. coli*, thus allowing the facile production of large amounts of the said fragments.

Whole antibodies, and F(ab')2 fragments are "bivalent". By "bivalent" we mean that the said antibodies and F(ab')2 fragments have two antigen combining sites. In contrast, Fab, Fv, ScFv and dAb fragments are monovalent, having only one antigen combining site. Synthetic antibodies capable of binding to IL-11, an IL-11 containing complex, or a receptor for IL-11 may also be made using phage display technology as is well known in the art.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992): Barbas et al. *Proc Nat. Acad. Sci. USA* 91:3809-3813 (1994): Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins el al, *J. Mol. Biol.* 226:889-896 (1992).

Antibodies/fragments include bi-specific antibodies, e.g. composed of two different fragments of two different antibodies, such that the bi-specific antibody binds two types of antigen. The bispecific antibody comprises an antibody/fragment as described herein capable of binding to IL-11, an IL-11 containing complex, or a receptor for IL-11. The antibody may contain a different fragment having affinity for a second antigen, which may be any desired antigen. Techniques for the preparation of bi-specific antibodies are well known in the art, e.g. see Mueller, D et al., (2010 *Biodrugs* 24 (2): 89-98), Wozniak-Knopp G et al., (2010 *Protein Eng Des* 23 (4): 289-297), and Baeuerle, P A et al., (2009 *Cancer Res* 69 (12): 4941-4944). Bispecific antibodies and bispecific antigen-binding fragments may be provided in any suitable format, such as those formats described in Kontermann MAbs 2012, 4(2): 182-197, which is hereby incorporated by reference in its entirety. For example, a bispecific antibody or bispecific antigen-binding fragment may be a bispecific antibody conjugate (e.g. an IgG2, F(ab')2 or CovX-Body), a bispecific IgG or IgG-like molecule (e.g. an IgG, scFv4-Ig, IgG-scFv, scFv-IgG, DVD-Ig, IgG-sVD, sVD-IgG, 2 in 1-IgG, mAb2, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (db), dsDb, DART, scDb, tandAbs, tandem scFv (taFv), tandem dAb/VHH, triple body, triple head, Fab-scFv, or F(ab')2-scFv2), a bispecific Fc and CH3 fusion protein (e.g. a taFv-Fc, Di-diabody, scDb-CH3, scFv-Fc-scFv, HCAb-VHH, scFv-kih-Fc, or scFv-kih-CH3), or a bispecific fusion protein (e.g. a scFv2-albumin, scDb-albumin, taFv-toxin, DNL-Fab3, DNL-Fab4-IgG, DNL-Fab4-IgG-cytokine2). See in particular FIG. 2 of Kontermann MAbs 2012, 4(2): 182-19.

Methods for producing bispecific antibodies include chemically crosslinking antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)2 heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen-binding fragments can also be produced recombinantly, by expression from e.g. a nucleic acid construct encoding polypeptides for the antigen binding molecules, for example as described in Antibody Engineering: Methods and Protocols, Second Edition (Humana Press. 2012), at Chapter 40: Production of Bispecific Antibodies: Diabodies and Tandem scFv (Hornig and Färber-Schwarz), or French, How to make bispecific antibodies. Methods Mol. Med. 2000; 40:333-339.

For example, a DNA construct encoding the light and heavy chain variable domains for the two antigen binding domains (i.e. the light and heavy chain variable domains for the antigen binding domain capable of binding to IL-11, an IL-11 containing complex, or a receptor for IL-11, and the light and heavy chain variable domains for the antigen binding domain capable of binding to another target protein), and including sequences encoding a suitable linker or dimerization domain between the antigen binding domains can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Decoy Receptors

Peptide or polypeptide based agents capable of binding to IL-11 or IL-11 containing complexes may be based on the IL-11 receptor, e.g. an IL-11 binding fragment of an IL-11 receptor.

In some embodiments, the binding agent may comprise an IL-11-binding fragment of the IL-11Rα chain, and may preferably be soluble and/or exclude one or more, or all, of the transmembrane domain(s). In some embodiments, the binding agent may comprise an IL-11-binding fragment of gp130, and may preferably be soluble and/or exclude one or more, or all, of the transmembrane domain(s). Such molecules may be described as decoy receptors. Binding of such agents may inhibit IL-11 mediated cis and/or trans-signalling by reducing/preventing the ability of IL-11 to bind to receptors for IL-11, e.g. IL-11Rα or gp130, thereby inhibiting downstream signalling.

Curtis et al (*Blood* 1997 Dec. 1; 90 (11):4403-12) report that a soluble murine IL-11 receptor alpha chain (sIL-11R) was capable of antagonizing the activity of IL-11 when tested on cells expressing the transmembrane IL-11R and gp130. They proposed that the observed IL-11 antagonism by the sIL-11R depends on limiting numbers of gp130 molecules on cells already expressing the transmembrane IL-11R.

The use of soluble decoy receptors as the basis for inhibition of signal transduction and therapeutic intervention has also been reported for other signalling molecule:receptor pairs, e.g. VEGF and the VEGF receptor (De-Chao Yu et al., Molecular Therapy (2012); 20 5, 938-947; Konner and Dupont Clin Colorectal Cancer 2004 October; 4 Suppl 2:S81-5).

As such, in some embodiments a binding agent may be a decoy receptor, e.g. a soluble receptor for IL-11 and/or IL-11 containing complexes. Competition for IL-11 and/or IL-11 containing complexes provided by a decoy receptor has been reported to lead to IL-11 antagonist action (Curtis et al., supra). Decoy IL-11 receptors are also described in WO 2017/103108 A1 and WO 2018/109168 A1, which are hereby incorporated by reference in their entirety.

Decoy IL-11 receptors preferably bind IL-11 and/or IL-11 containing complexes, and thereby make these species unavailable for binding to gp130, IL-11Rα and/or gp130:IL-11Rα receptors. As such, they act as 'decoy' receptors for IL-11 and IL-11 containing complexes, much in the same way that etanercept acts as a decoy receptor for TNFα. IL-11-mediated signalling is reduced as compared to the level of signalling in the absence of the decoy receptor.

Decoy IL-11 receptors preferably bind to IL-11 through one or more cytokine binding modules (CBMs). The CBMs are, or are derived from or homologous to, the CBMs of naturally occurring receptor molecules for IL-11. For example, decoy IL-11 receptors may comprise, or consist of, one or more CBMs which are from, are derived from or homologous to the CBM of gp130 and/or IL-11Rα.

In some embodiments, a decoy IL-11 receptor may comprise, or consist of, an amino acid sequence corresponding to the cytokine binding module of gp130. In some embodiments, a decoy IL-11 receptor may comprise an amino acid sequence corresponding to the cytokine binding module of IL-11Rα. Herein, an amino acid sequence which 'corresponds' to a reference region or sequence of a given peptide/polypeptide has at least 60%, e.g. one of at least 65%, 70%, 75%, 80%, 85%, 90%, 91%, 92%, 93%, 94%, 95%, 96%, 97%, 98% or 99% sequence identity to the amino acid sequence of the reference region/sequence.

In some embodiments a decoy receptor may be able to bind IL-11, e.g. with binding affinity of at least 100 μM or less, optionally one of 10 μM or less, 1 μM or less, 100 nM or less, or about 1 to 100 nM. In some embodiments a decoy receptor may comprise all or part of the IL-11 binding domain and may optionally lack all or part of the transmembrane domains. The decoy receptor may optionally be fused to an immunoglobulin constant region, e.g. IgG Fc region.

Inhibitors

The present invention contemplates the use of inhibitor molecules capable of binding to one or more of IL-11, an IL-11 containing complex, IL-11Rα, gp130, or a complex containing IL-11Rα and/or gp130, and inhibiting IL-11 mediated signalling.

In some embodiments the agent is a peptide- or polypeptide-based binding agent based on IL-11, e.g. mutant, variant or binding fragment of IL-11. Suitable peptide or polypeptide based agents may bind to a receptor for IL-11 (e.g. IL-11Rα, gp130, or a complex containing IL-11Rα and/or gp130) in a manner that does not lead to initiation of signal transduction, or which produces sub-optimal signalling. IL-11 mutants of this kind may act as competitive inhibitors of endogenous IL-11.

For example, W147A is an IL-11 antagonist in which the amino acid 147 is mutated from a tryptophan to an alanine, which destroys the so-called 'site III' of IL-11. This mutant can bind to IL-11Rα, but engagement of the gp130 homodimer fails, resulting in efficient blockade of IL-11 signalling (Underhill-Day et al., 2003; *Endocrinology* 2003 August; 144(8):3406-14). Lee et al (*Am J respire Cell Mol Biol.* 2008 December; 39(6):739-746) also report the generation of an IL-11 antagonist mutant (a "mutein") capable of specifically inhibiting the binding of IL-11 to IL-11Rα. IL-11 muteins are also described in WO 2009/052588 A1.

Menkhorst et al (Biology of Reproduction May 1, 2009 vol. 80 no. 5 920-927) describe a PEGylated IL-11 antagonist, PEGIL11A (CSL Limited, Parkvill, Victoria, Australia) which is effective to inhibit IL-11 action in female mice.

Pasqualini et al. *Cancer* (2015) 121(14):2411-2421 describe a ligand-directed, peptidomimetic drug, bone metastasis-targeting peptidomimetic-11 (BMTP-11) capable of binding to IL-11Rα.

In some embodiments a binding agent capable of binding to a receptor for IL-11 may be provided in the form of a small molecule inhibitor of one of IL-11Rα, gp130, or a complex containing IL-11Rα and/or gp130. In some embodiments a binding agent may be provided in the form of a small molecule inhibitor of IL-11 or an IL-11 containing complex, e.g. IL-11 inhibitor described in Lay et al., Int. J. Oncol. (2012); 41(2): 759-764, which is hereby incorporated by reference in its entirety.

Aptamers

In some embodiments, an agent capable of binding to IL-11/an IL-11 containing complex or a receptor for IL-11 (e.g. IL-11Rα, gp130, or a complex containing IL-11Rα and/or gp130) is an aptamer. Aptamers, also called nucleic acid/peptide ligands, are nucleic acid or peptide molecules characterised by the ability to bind to a target molecule with high specificity and high affinity. Almost every aptamer identified to date is a non-naturally occurring molecule.

Aptamers to a given target (e.g. IL-11, an IL-11 containing complex or a receptor for IL-11) may be identified and/or produced by the method of Systematic Evolution of Ligands by EXponential enrichment (SELEX™), or by developing SOMAmers (slow off-rate modified aptamers) (Gold L et al. (2010) PLoS ONE 5(12):e15004). Aptamers and SELEX are described in Tuerk and Gold, Science (1990) 249(4968):505-10, and in WO 91/19813. Applying the SELEX and the SOMAmer technology includes for instance adding functional groups that mimic amino acid side chains to expand the aptamer's chemical diversity. As a result high affinity aptamers for a target may be enriched and identified.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesised by methods which are well known to the skilled person. For example, aptamers may be chemically synthesised, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer (e.g., see Sinha, N. D.; Biernat, J.; McManus, J.; Köster, H. Nucleic Acids Res. 1984, 12, 4539; and Beaucage, S. L.; Lyer, R. P. (1992), Tetrahedron 48 (12): 2223).

Suitable nucleic acid aptamers may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Suitable nucleic acid aptamers may optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. Suitable nucleic acid aptamers may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Aptamers may be peptides selected or engineered to bind specific target molecules. Peptide aptamers and methods for their generation and identification are reviewed in Reverdatto et al., *Curr Top Med Chem.* (2015) 15(12):1082-101, which is hereby incorporated by reference in its entirety. Peptide aptamers may optionally have a minimum length of one of 2, 3, 4, 5, 6, 7, 8, 9 or 10 amino acids. Peptide aptamers may optionally have a maximum length of one of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. Suitable peptide aptamers may optionally have a length of one of 2-30, 2-25, 2-20, 5-30, 5-25 or 5-20 amino acids.

Aptamers may have $K_D$'s in the nM or pM range, e.g. less than one of 500 nM, 100 nM, 50 nM, 10 nM, 1 nM, 500 pM, 100 pM.

Properties of IL-11 Binding Agents

Agents capable of binding to IL-11/an IL-11 containing complex or a receptor for IL-11 according to the present invention may exhibit one or more of the following properties:

Specific binding to IL-11/IL-11 containing complex or a receptor for IL-11;
Binding to IL-11/IL-11 containing complex, or a receptor for IL-11, with a KD of 10 µM or less, preferably one of ≤5 µM ≤1 µM, ≤500 nM, ≤100 nM, ≤10 nM, ≤1 nM or ≤100 pM;
Inhibition of interaction between IL-11 and IL-11Rα;
Inhibition of interaction between IL-11 and gp130;
Inhibition of interaction between IL-11 and IL-11Rα: gp130 receptor complex;
Inhibition of interaction between IL-11:IL-11Rα complex and gp130.

These properties can be determined by analysis of the relevant agent in a suitable assay, which may involve comparison of the performance of the agent to suitable control agents. The skilled person is able to identify an appropriate control conditions for a given assay.

For example, a suitable negative control for the analysis of the ability of a test antibody/antigen-binding fragment to bind to IL-11/an IL-11 containing complex/a receptor for IL-11 may be an antibody/antigen-binding fragment directed against a non-target protein (i.e. an antibody/antigen-binding fragment which is not specific for IL-11/an IL-11 containing complex/a receptor for IL-11). A suitable positive control may be a known, validated (e.g. commercially available) IL-11- or IL-11 receptor-binding antibody. Controls may be of the same isotype as the putative IL-11/IL-11 containing complex/IL-11 receptor-binding antibody/antigen-binding fragment being analysed, and may e.g. have the same constant regions.

In some embodiments, the agent may be capable of binding specifically to IL-11 or an IL-11 containing complex, or a receptor for IL-11 (e.g. IL-11Rα, gp130, or a complex containing IL-11Rα and/or gp130). An agent which specifically binds to a given target molecule preferably binds the target with greater affinity, and/or with greater duration than it binds to other, non-target molecules.

In some embodiments the agent may bind to IL-11 or an IL-11 containing complex with greater affinity than the affinity of binding to one or more other members of the IL-6 cytokine family (e.g. IL-6, leukemia inhibitory factor (LIF), oncostatin M (OSM), cardiotrophin-1 (CT-1), ciliary neurotrophic factor (CNTF) and cardiotrophin-like cytokine (CLC)). In some embodiments the agent may bind to a receptor for IL-11 (e.g. IL-11Rα, gp130, or a complex containing IL-11Rα and/or gp130) with greater affinity than the affinity of binding to one or more other members of the IL-6 receptor family. In some embodiments the agent may bind with greater affinity to IL-11Rα than the affinity of binding to one or more of IL-6Rα, leukemia inhibitory factor receptor (LIFR), oncostatin M receptor (OSMR), ciliary neurotrophic factor receptor alpha (CNTFRα) and cytokine receptor-like factor 1 (CRLF1).

In some embodiments, the extent of binding of a binding agent to an non-target is less than about 10% of the binding of the agent to the target as measured, e.g., by ELISA, SPR, Bio-Layer Interferometry (BLI), MicroScale Thermophoresis (MST), or by a radioimmunoassay (RIA). Alternatively, the binding specificity may be reflected in terms of binding affinity, where the binding agent binds to IL-11, an IL-11 containing complex or a receptor for IL-11 with a $K_D$ that is at least 0.1 order of magnitude (i.e. 0.1×10n, where n is an integer representing the order of magnitude) greater than the $K_D$ towards another, non-target molecule. This may optionally be one of at least 0.2, 0.3, 0.4, 0.5, 0.6, 0.7, 0.8, 0.9, 1.0, 1.5, or 2.0.

Binding affinity for a given binding agent for its target is often described in terms of its dissociation constant ($K_D$). Binding affinity can be measured by methods known in the art, such as by ELISA, Surface Plasmon Resonance (SPR; see e.g. Hearty et al., *Methods Mol Biol* (2012) 907:411-442; or Rich et al., *Anal Biochem.* 2008 Feb. 1; 373(1):112-20), Bio-Layer Interferometry (see e.g. Lad et al., (2015) *J Biomol Screen* 20(4): 498-507; or Concepcion et al., *Comb Chem High Throughput Screen.* 2009 September; 12(8):791-800), MicroScale Thermophoresis (MST) analysis (see e.g. Jerabek-Willemsen et al., *Assay Drug Dev Technol.* 2011 August; 9(4): 342-353), or by a radiolabelled antigen binding assay (RIA).

In some embodiments, the agent is capable of binding to IL-11 or an IL-11 containing complex, or a receptor for IL-11 with a $K_D$ of 50 µM or less, preferably one of ≤10 µM, ≤5 µM, ≤4 µM, ≤3 µM, ≤2 µM, ≤1 µM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 pM, ≤400 pM, ≤300 pM, ≤200 pM, or ≤100 pM.

In some embodiments, the agent binds to IL-11, an IL-11 containing complex or a receptor for IL-11 with an affinity of binding (e.g. as determined by ELISA) of EC50=10,000 ng/ml or less, preferably one of ≤5,000 ng/ml, ≤1000 ng/ml, ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, 40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml. Such ELISAs can be performed e.g. as described in Antibody Engineering, vol. 1 (2nd Edn), Springer Protocols, Springer (2010), Part V, pp 657-665.

In some embodiments, the agent binds to IL-11 or an IL-11-containing complex in a region which is important for binding to a receptor for the IL-11 or IL-11-containing complex, e.g. gp130 or IL-11Rα, and thereby inhibits interaction between IL-11 or an IL-11-containing complex and a receptor for IL-11, and/or signalling through the receptor. In some embodiments, the agent binds to a receptor for IL-11 in a region which is important for binding to IL-11 or an IL-11-containing complex, and thereby inhibits interaction between IL-11 or an IL-11-containing complex and a receptor for IL-11, and/or signalling through the receptor.

The ability of a given binding agent (e.g. an agent capable of binding IL-11/an IL-11 containing complex or a receptor for IL-11) to inhibit interaction between two proteins can be determined for example by analysis of interaction in the presence of, or following incubation of one or both of the interaction partners with, the binding agent. An example of a suitable assay to determine whether a given binding agent is capable of inhibiting interaction between two interaction partners is a competition ELISA.

A binding agent which is capable of inhibiting a given interaction (e.g. between IL-11 and IL-11Rα, or between IL-11 and gp130, or between IL-11 and IL-11Rα:gp130, or between IL-11:IL-11Rα and gp130) is identified by the observation of a reduction/decrease in the level of interaction between the interaction partners in the presence of—or following incubation of one or both of the interaction partners with—the binding agent, as compared to the level of interaction in the absence of the binding agent (or in the presence of an appropriate control binding agent). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the binding agent may be labelled or used in conjunction with a detectable entity for the purposes of detecting and/or measuring the level of interaction. For example, the agent may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding agent may be directly labelled with a detectable label or it may be indirectly labelled. For example, the binding agent may be unlabelled, and detected by another binding agent which is itself labelled.

Alternatively, the second binding agent may have bound to it biotin and binding of labelled streptavidin to the biotin may be used to indirectly label the first binding agent.

Ability of a binding agent to inhibit interaction between two binding partners can also be determined by analysis of the downstream functional consequences of such interaction, e.g. IL-11-mediated signalling. For example, downstream functional consequences of interaction between IL-11 and IL-11Rα:gp130 or between IL-11:IL-11Rα and gp130 may include e.g. a process mediated by IL-11, or gene/protein expression of e.g. collagen or IL-11.

Inhibition of interaction between IL-11 or an IL-11 containing complex and a receptor for IL-11 can be analysed using 3H-thymidine incorporation and/or Ba/F3 cell proliferation assays such as those described in e.g. Curtis et al. Blood, 1997, 90(11) and Karpovich et al. Mol. Hum. Reprod. 2003 9(2): 75-80. Ba/F3 cells co-express IL-11Rα and gp130.

In some embodiments, the binding agent may be capable of inhibiting interaction between IL-11 and IL-11Rα to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα in the absence of the binding agent (or in the presence of an appropriate control binding agent). In some embodiments, the binding agent may be capable of inhibiting interaction between IL-11 and IL-11Rα to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα in the absence of the binding agent (or in the presence of an appropriate control binding agent).

In some embodiments, the binding agent may be capable of inhibiting interaction between IL-11 and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and gp130 in the absence of the binding agent (or in the presence of an appropriate control binding agent). In some embodiments, the binding agent may be capable of inhibiting interaction between IL-11 and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and gp130 in the absence of the binding agent (or in the presence of an appropriate control binding agent).

In some embodiments, the binding agent may be capable of inhibiting interaction between IL-11 and IL-11Rα:gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα:gp130 in the absence of the binding agent (or in the presence of an appropriate control binding agent). In some embodiments, the binding agent may be capable of inhibiting interaction between IL-11 and IL-11Rα:gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα:gp130 in the absence of the binding agent (or in the presence of an appropriate control binding agent).

In some embodiments, the binding agent may be capable of inhibiting interaction between IL-11:IL-11Rα complex and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the binding agent (or in the presence of an appropriate control binding agent). In some embodiments, the binding agent is capable of inhibiting interaction between IL-11:IL-11Rα complex and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11:IL-11Rα complex and gp130 in the absence of the binding agent.

Agents Capable of Reducing Expression of IL-11 or an IL-11 Receptor

In aspects of the present invention the agent capable of inhibiting IL-11-mediated signalling may be capable of preventing or reducing the expression of one or more of IL-11, IL-11Rα or gp130.

Expression may be gene or protein expression, and may be determined as described herein or by methods in the art that will be well known to a skilled person. Expression may be by a cell/tissue/organ/organ system of a subject.

Suitable agents may be of any kind, but in some embodiments an agent capable of preventing or reducing the expression of one or more of IL-11, IL-11Rα or gp130 may be a small molecule or an oligonucleotide.

An agent capable of preventing or reducing of the expression of one or more of IL-11, IL-11Rα or gp130 may do so e.g. through inhibiting transcription of the gene encoding IL-11, IL-11Rα or gp130, inhibiting post-transcriptional processing of RNA encoding IL-11, IL-11Rα or gp130, reducing the stability of RNA encoding IL-11, IL-11Rα or gp130, promoting degradation of RNA encoding IL-11, IL-11Rα or gp130, inhibiting post-translational processing of IL-11, IL-11Rα or gp130 polypeptide, reducing the stability of IL-11, IL-11Rα or gp130 polypeptide or promoting degradation of IL-11, IL-11Rα or gp130 polypeptide.

Taki et al. *Clin Exp Immunol* (1998) April; 112(1): 133-138 reported a reduction in the expression of IL-11 in rheumatoid synovial cells upon treatment with indomethacin, dexamethasone or interferon-gamma (IFNγ).

The present invention contemplates the use of antisense nucleic acid to prevent/reduce expression of IL-11, IL-11Rα or gp130. In some embodiments, an agent capable of preventing or reducing the expression of IL-11, IL-11Rα or gp130 may cause reduced expression by RNA interference (RNAi).

In some embodiments, the agent may be an inhibitory nucleic acid, such as antisense or small interfering RNA, including but not limited to shRNA or siRNA.

In some embodiments the inhibitory nucleic acid is provided in a vector. For example, in some embodiments the agent may be a lentiviral vector encoding shRNA for one or more of IL-11, IL-11Rα or gp130.

Oligonucleotide molecules, particularly RNA, may be employed to regulate gene expression. These include antisense oligonucleotides, targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

An antisense oligonucleotide is an oligonucleotide, preferably single-stranded, that targets and binds, by complementary sequence binding, to a target oligonucleotide, e.g. mRNA. Where the target oligonucleotide is an mRNA, binding of the antisense to the mRNA blocks translation of the mRNA and expression of the gene product. Antisense oligonucleotides may be designed to bind sense genomic nucleic acid and inhibit transcription of a target nucleotide sequence.

In view of the known nucleic acid sequences for IL-11, IL-11Rα and gp130 (e.g. the known mRNA sequences available from GenBank under Accession No.s: BC012506.1 G:15341754 (human IL-11), BC134354.1 G:126632002 (mouse IL-11), AF347935.1 GI:13549072 (rat IL-11), NM_001142784.2 GI:391353394 (human IL-11Rα), NM_001163401.1 GI:254281268 (mouse IL-11Rα), NM_139116.1 GI:20806172 (rat IL-11Rα), NM_001190981.1 GI:300244534 (human gp130), NM_010560.3 GI:225007624 (mouse gp130), NM_001008725.3 GI:300244570 (rat gp130)) oligonucleotides may be designed to repress or silence the expression of IL-11, IL-11Rα or gp130.

Such oligonucleotides may have any length, but may preferably be short, e.g. less than 100 nucleotides, e.g. 10-40 nucleotides, or 20-50 nucleotides, and may comprise a nucleotide sequence having complete- or near-complementarity (e.g. 80%, 85%, 90%, 91%, 92%, 93%, 94%, 95%, 96%, 97%, 98%, 99% or 100% complementarity) to a sequence of nucleotides of corresponding length in the target oligonucleotide, e.g. the IL-11, IL-11Rα or gp130 mRNA. The complementary region of the nucleotide sequence may have any length, but is preferably at least 5, and optionally no more than 50, nucleotides long, e.g. one of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

Repression of expression of IL-11, IL-11Rα or gp130 will preferably result in a decrease in the quantity of IL-11, IL-11Rα or gp130 expressed by a cell/tissue/organ/organ system/subject. For example, in a given cell the repression of IL-11, IL-11Rα or gp130 by administration of a suitable nucleic acid will result in a decrease in the quantity of IL-11, IL-11Rα or gp130 expressed by that cell relative to an untreated cell. Repression may be partial. Preferred degrees of repression are at least 50%, more preferably one of at least 60%, 70%, 80%, 85% or 90%. A level of repression between 90% and 100% is considered a 'silencing' of expression or function.

A role for the RNAi machinery and small RNAs in targeting of heterochromatin complexes and epigenetic gene silencing at specific chromosomal loci has been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA. RNAi based therapeutics have been progressed into Phase I, II and III clinical trials for a number of indications (Nature 2009 Jan. 22; 457(7228):426-433).

In the art, these RNA sequences are termed "short or small interfering RNAs" (siRNAs) or "microRNAs" (miRNAs) depending on their origin. Both types of sequence may be used to down-regulate gene expression by binding to complementary RNAs and either triggering mRNA elimination (RNAi) or arresting mRNA translation into protein. siRNA are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

siRNA ligands are typically double stranded and, in order to optimise the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, *PLoS Biology*, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such the Ambion siRNA finder. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of IL-11, IL-11Rα or gp130. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of IL-11, IL-11Rα or gp130.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific (e.g. heart, liver, or kidney specific) promoter. In a further embodiment, the siRNA, longer dsRNA or miRNA is produced exogenously (in vitro) by transcription from a vector.

Suitable vectors may be oligonucleotide vectors configured to express the oligonucleotide agent capable of IL-11, IL-11Rα or gp130 repression. Such vectors may be viral vectors or plasmid vectors. The therapeutic oligonucleotide may be incorporated in the genome of a viral vector and be operably linked to a regulatory sequence, e.g. promoter, which drives its expression. The term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence.

Viral vectors encoding promoter-expressed siRNA sequences are known in the art and have the benefit of long term expression of the therapeutic oligonucleotide. Examples include lentiviral (*Nature* 2009 Jan. 22; 457 (7228):426-433), adenovirus (Shen et al., *FEBS Lett* 2003 Mar. 27; 539(1-3)111-4) and retroviruses (Barton and Medzhitov *PNAS* Nov. 12, 2002 vol. 99, no. 23 14943-14945).

In other embodiments a vector may be configured to assist delivery of the therapeutic oligonucleotide to the site at which repression of IL-11, IL-11Rα or gp130 expression is required. Such vectors typically involve complexing the oligonucleotide with a positively charged vector (e.g., cationic cell penetrating peptides, cationic polymers and dendrimers, and cationic lipids): conjugating the oligonucleotide with small molecules (e.g., cholesterol, bile acids, and lipids), polymers, antibodies, and RNAs; or encapsulating the oligonucleotide in nanoparticulate formulations (Wang et al., *AAPS J.* 2010 December; 12(4): 492-503).

In one embodiment, a vector may comprise a nucleic acid sequence in both the sense and antisense orientation, such that when expressed as RNA the sense and antisense sections will associate to form a double stranded RNA.

Alternatively, siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through-O-or-S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3'position and other than a phosphate group at the 5'position. Thus modified nucleotides may also include 2'substituted sugars such as 2'-O-methyl-; 2'-O-alkyl; 2'-O-allyl; 2'-S-alkyl; 2'-S-allyl; 2'-fluoro-; 2'-halo or azido-ribose, carbocyclic sugar analogues, a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine,5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methylthio-N6-isopentenyladenine, uracil-5-oxyacetic acid methyl ester, pseudouracil, 2-thiocytosine, 5-methyl-2 thiouracil, 2-thiouracil, 4-thiouracil, 5methyluracil, N-uracil-5-oxyacetic acid methylester, uracil 5-oxyacetic acid, queosine, 2-thiocytosine, 5-propyluracil, 5-propylcytosine, 5-ethyluracil, 5ethylcytosine, 5-butyluracil, 5-phenyluracil, 5-pentylcytosine, and 2,6,diaminopurine, methylpsuedouracil, 1-methylguanine, 1-methylcytosine.

Methods relating to the use of RNAi to silence genes in *C. elegans, Drosophila*, plants, and mammals are known in the art (Fire A, et al., 1998 *Nature* 391:806-811; Fire A. *Trends Genet.* 15, 358-363 (1999); Sharp, P. A. *RNA interference* 2001. *Genes Dev.* 15, 485-490 (2001); Hammond, S. M., et al., *Nature Rev. Genet.* 2, 110-1119 (2001); Tuschl, T. *Chem. Biochem.* 2, 239-245 (2001); Hamilton, A. et al., *Science* 286, 950-952 (1999); Hammond, S. M., et al., *Nature* 404, 293-296 (2000); Zamore, P. D., et al., *Cell* 101, 25-33 (2000): Bernstein, E., et al., *Nature* 409, 363-366 (2001); Elbashir, S. M., et al., *Genes Dev.* 15, 188-200 (2001); WO0129058; WO9932619, and Elbashir S M, et al., 2001 *Nature* 411:494-498).

Accordingly, the invention provides nucleic acid that is capable, when suitably introduced into or expressed within a mammalian, e.g. human, cell that otherwise expresses IL-11, IL-11Rα or gp130, of suppressing IL-11, IL-11Rα or gp130 expression by RNAi.

Nucleic acid sequences for IL-11, IL-11Rα and gp130 (e.g. the known mRNA sequences available from GenBank under Accession No.s: BC012506.1 GI:15341754 (human IL-11), BC134354.1 GI:126632002 (mouse IL-11), AF347935.1 GI:13549072 (rat IL-11), NM_001142784.2 GI:391353394 (human IL-11Rα), NM_001163401.1 GI:254281268 (mouse IL-11Rα), NM_139116.1 GI:20806172 (rat IL-11Rα), NM_001190981.1 GI:300244534 (human gp130), NM_010560.3 GI:225007624 (mouse gp130), NM_001008725.3 GI:300244570 (rat gp130)) oligonucleotides may be designed to repress or silence the expression of IL-11, IL-11Rα or gp130.

The nucleic acid may have substantial sequence identity to a portion of IL-11, IL-11Rα or gp130 mRNA, e.g. as defined in GenBank accession no. NM_000641.3 GI:391353405 (IL-11), NM_001142784.2 GI:391353394 (IL-11Rα), NM_001190981.1 GI:300244534 (gp130) or the complementary sequence to said mRNA.

The nucleic acid may be a double-stranded siRNA. (As the skilled person will appreciate, and as explained further below, a siRNA molecule may include a short 3' DNA sequence also.)

Alternatively, the nucleic acid may be a DNA (usually double-stranded DNA) which, when transcribed in a mammalian cell, yields an RNA having two complementary portions joined via a spacer, such that the RNA takes the form of a hairpin when the complementary portions hybridise with each other. In a mammalian cell, the hairpin structure may be cleaved from the molecule by the enzyme DICER, to yield two distinct, but hybridised, RNA molecules.

In some preferred embodiments, the nucleic acid is generally targeted to the sequence of one of SEQ ID NOs 4 to 7 (IL-11) or to one of SEQ ID NOs 8 to 11 (IL-11Rα).

Only single-stranded (i.e. non self-hybridised) regions of an mRNA transcript are expected to be suitable targets for RNAi. It is therefore proposed that other sequences very close in the IL-11 or IL-11Rα mRNA transcript to the sequence represented by one of SEQ ID NOs 4 to 7 or 8 to 11 may also be suitable targets for RNAi. Such target sequences are preferably 17-23 nucleotides in length and preferably overlap one of SEQ ID NOs 4 to 7 or 8 to 11 by at least 1, 2, 3, 4, 5, 6, 7, 8, 9, 10, 11, 12, 13, 14, 15, 16, 17, 18 or all 19 nucleotides (at either end of one of SEQ ID NOs 4 to 7 or 8 to 11).

Accordingly, the invention provides nucleic acid that is capable, when suitably introduced into or expressed within a mammalian cell that otherwise expresses IL-11 or IL-11Rα, of suppressing IL-11 or IL-11Rα expression by RNAi, wherein the nucleic acid is generally targeted to the sequence of one of SEQ ID NOs 4 to 7 or 8 to 11.

By "generally targeted" the nucleic acid may target a sequence that overlaps with SEQ ID NOs 4 to 7 or 8 to 11. In particular, the nucleic acid may target a sequence in the mRNA of human IL-11 or IL-11Rα that is slightly longer or shorter than one of SEQ ID NOs 4 to 7 or 8 to 11 (preferably from 17-23 nucleotides in length), but is otherwise identical to one of SEQ ID NOs 4 to 7 or 8 to 11.

It is expected that perfect identity/complementarity between the nucleic acid of the invention and the target sequence, although preferred, is not essential. Accordingly, the nucleic acid of the invention may include a single mismatch compared to the mRNA of IL-11 or IL-11Rα. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

In one embodiment, the nucleic acid (herein referred to as double-stranded siRNA) includes the double-stranded RNA sequences shown in SEQ ID NOs 12 to 15. In another embodiment, the nucleic acid (herein referred to as double-stranded siRNA) includes the double-stranded RNA sequences shown in SEQ ID NOs 16 to 19.

However, it is also expected that slightly shorter or longer sequences directed to the same region of IL-11 or IL-11Rα mRNA will also be effective. In particular, it is expected that double-stranded sequences between 17 and 23 bp in length will also be effective.

The strands that form the double-stranded RNA may have short 3' dinucleotide overhangs, which may be DNA or RNA. The use of a 3' DNA overhang has no effect on siRNA activity compared to a 3' RNA overhang, but reduces the cost of chemical synthesis of the nucleic acid strands (Elbashir et al., 2001c). For this reason, DNA dinucleotides may be preferred.

When present, the dinucleotide overhangs may be symmetrical to each other, though this is not essential. Indeed, the 3' overhang of the sense (upper) strand is irrelevant for RNAi activity, as it does not participate in mRNA recognition and degradation (Elbashir et al., 2001a, 2001b, 2001c).

While RNAi experiments in *Drosophila* show that antisense 3' overhangs may participate in mRNA recognition and targeting (Elbashir et al. 2001c), 3' overhangs do not appear to be necessary for RNAi activity of siRNA in mammalian cells. Incorrect annealing of 3' overhangs is therefore thought to have little effect in mammalian cells (Elbashir et al. 2001c; Czauderna et al. 2003).

Any dinucleotide overhang may therefore be used in the antisense strand of the siRNA. Nevertheless, the dinucleotide is preferably -UU or -UG (or -TT or -TG if the overhang is DNA), more preferably -UU (or -TT). The -UU (or -TT) dinucleotide overhang is most effective and is consistent with (i.e. capable of forming part of) the RNA polymerase III end of transcription signal (the terminator signal is TTTTT). Accordingly, this dinucleotide is most preferred. The dinucleotides AA, CC and GG may also be used, but are less effective and consequently less preferred.

Moreover, the 3' overhangs may be omitted entirely from the siRNA.

The invention also provides single-stranded nucleic acids (herein referred to as single-stranded siRNAs) respectively consisting of a component strand of one of the aforementioned double-stranded nucleic acids, preferably with the 3'-overhangs, but optionally without. The invention also provides kits containing pairs of such single-stranded nucleic acids, which are capable of hybridising with each other in vitro to form the aforementioned double-stranded siRNAs, which may then be introduced into cells.

The invention also provides DNA that, when transcribed in a mammalian cell, yields an RNA (herein also referred to as an shRNA) having two complementary portions which are capable of self-hybridising to produce a double-stranded motif, e.g. including a sequence selected from the group consisting of SEQ ID NOs: 12 to 15 or 16 to 19 or a sequence that differs from any one of the aforementioned sequences by a single base pair substitution.

The complementary portions will generally be joined by a spacer, which has suitable length and sequence to allow the two complementary portions to hybridise with each other. The two complementary (i.e. sense and antisense) portions may be joined 5'-3' in either order. The spacer will typically be a short sequence, of approximately 4-12 nucleotides, preferably 4-9 nucleotides, more preferably 6-9 nucleotides.

Preferably the 5' end of the spacer (immediately 3' of the upstream complementary portion) consists of the nucleotides -UU- or -UG-, again preferably -UU- (though, again, the use of these particular dinucleotides is not essential). A suitable spacer, recommended for use in the pSuper system of OligoEngine (Seattle, Washington, USA) is UUCAAGAGA. In this and other cases, the ends of the spacer may hybridise with each other, e.g. elongating the double-stranded motif beyond the exact sequences of SEQ ID NOs 12 to 15 or 16 to 19 by a small number (e.g. 1 or 2) of base pairs.

Similarly, the transcribed RNA preferably includes a 3' overhang from the downstream complementary portion. Again, this is preferably -UU or -UG, more preferably -UU.

Such shRNA molecules may then be cleaved in the mammalian cell by the enzyme DICER to yield a double-stranded siRNA as described above, in which one or each strand of the hybridised dsRNA includes a 3' overhang.

Techniques for the synthesis of the nucleic acids of the invention are of course well known in the art.

The skilled person is well able to construct suitable transcription vectors for the DNA of the invention using well-known techniques and commercially available materials. In particular, the DNA will be associated with control sequences, including a promoter and a transcription termination sequence.

Of particular suitability are the commercially available pSuper and pSuperior systems of OligoEngine (Seattle, Washington, USA). These use a polymerase-III promoter (H1) and a T5 transcription terminator sequence that contributes two U residues at the 3' end of the transcript (which, after DICER processing, provide a 3' UU overhang of one strand of the siRNA).

Another suitable system is described in Shin et al. (RNA, 2009 May; 15(5): 898-910), which uses another polymerase-III promoter (U6).

The double-stranded siRNAs of the invention may be introduced into mammalian cells in vitro or in vivo using known techniques, as described below, to suppress expression of IL-11 or a receptor for IL-11.

Similarly, transcription vectors containing the DNAs of the invention may be introduced into tumour cells in vitro or in vivo using known techniques, as described below, for transient or stable expression of RNA, again to suppress expression of IL-11 or a receptor for IL-11.

Accordingly, the invention also provides a method of suppressing expression of IL-11 or a receptor for IL-11 in a mammalian, e.g. human, cell, the method comprising administering to the cell a double-stranded siRNA of the invention or a transcription vector of the invention.

Similarly, the invention further provides a method of treating kidney injury and/or a disorder, disease or condition associated with kidney injury, the method comprising administering to a subject a double-stranded siRNA of the invention or a transcription vector of the invention.

The invention further provides the double-stranded siRNAs of the invention and the transcription vectors of the invention, for use in a method of treatment, preferably a method of treating kidney injury and/or a disorder, disease or condition associated with kidney injury.

The invention further provides the use of the double-stranded siRNAs of the invention and the transcription vectors of the invention in the preparation of a medicament for the treatment of kidney injury and/or a disorder, disease or condition associated with kidney injury.

The invention further provides a composition comprising a double-stranded siRNA of the invention or a transcription vector of the invention in admixture with one or more pharmaceutically acceptable carriers. Suitable carriers include lipophilic carriers or vesicles, which may assist in penetration of the cell membrane.

Materials and methods suitable for the administration of siRNA duplexes and DNA vectors of the invention are well known in the art and improved methods are under development, given the potential of RNAi technology.

Generally, many techniques are available for introducing nucleic acids into mammalian cells. The choice of technique will depend on whether the nucleic acid is transferred into cultured cells in vitro or in vivo in the cells of a patient. Techniques suitable for the transfer of nucleic acid into mammalian cells in vitro include the use of liposomes, electroporation, microinjection, cell fusion, DEAE, dextran and calcium phosphate precipitation. In vivo gene transfer techniques include transfection with viral (typically retroviral) vectors and viral coat protein-liposome mediated transfection (Dzau et al. (2003) *Trends in Biotechnology* 11, 205-210).

In particular, suitable techniques for cellular administration of the nucleic acids of the invention both in vitro and in vivo are disclosed in the following articles:

General reviews: Borkhardt, A. 2002. Blocking oncogenes in malignant cells by RNA interference—new hope for a highly specific cancer treatment? Cancer Cell. 2:167-8. Hannon, G. J. 2002. RNA interference. Nature. 418:244-51. McManus, M. T., and P. A. Sharp. 2002. Gene silencing in mammals by small interfering RNAs. Nat Rev Genet. 3:737-47. Scherr, M., M. A. Morgan, and M. Eder. 2003b. Gene silencing mediated by small interfering RNAs in mammalian cells. Curr Med Chem. 10:245-56. Shuey, D. J., D. E. McCallus, and T. Giordano. 2002. RNAi: gene-silencing in therapeutic intervention. Drug Discov Today. 7:1040-6.

Systemic delivery using liposomes: Lewis, D. L., J. E. Hagstrom, A. G. Loomis, J. A. Wolff, and H. Herweijer. 2002. Efficient delivery of siRNA for inhibition of gene expression in postnatal mice. Nat Genet. 32:107-8. Paul, C. P., P. D. Good, I. Winer, and D. R. Engelke. 2002. Effective expression of small interfering RNA in human cells. Nat Biotechnol. 20:505-8. Song, E., S. K. Lee, J. Wang, N. Ince, N. Ouyang, J. Min, J. Chen, P. Shankar, and J. Lieberman. 2003. RNA interference targeting Fas protects mice from fulminant hepatitis. Nat Med. 9:347-51. Sorensen, D. R., M. Leirdal, and M. Sioud. 2003. Gene silencing by systemic delivery of synthetic siRNAs in adult mice. J Mol Biol. 327:761-6.

Virus mediated transfer: Abbas-Terki, T., W. Blanco-Bose, N. Deglon, W. Pralong, and P. Aebischer. 2002. Lentiviral-mediated RNA interference. Hum Gene Ther. 13:2197-201. Barton, G. M., and R. Medzhitov. 2002. Retroviral delivery of small interfering RNA into primary cells. Proc Natl Acad Sci USA. 99:14943-5. Devroe, E., and P. A. Silver. 2002. Retrovirus-delivered siRNA. BMC Biotechnol. 2:15. Lori, F., P. Guallini, L. Galluzzi, and J. Lisziewicz. 2002. Gene therapy approaches to HIV infection. Am J Pharmacogenomics. 2:245-52. Matta, H., B. Hozayev, R. Tomar, P. Chugh, and P. M. Chaudhary. 2003. Use of lentiviral vectors for delivery of small interfering RNA. Cancer Biol Ther. 2:206-10. Qin, X. F., D. S. An, I. S. Chen, and D. Baltimore. 2003. Inhibiting HIV-1 infection in human T cells by lentiviral-mediated delivery of small interfering RNA against CCR5. Proc Natl Acad Sci USA. 100:183-8. Scherr, M., K. Battmer, A. Ganser, and M. Eder. 2003a. Modulation of gene expression by lentiviral-mediated delivery of small interfering RNA. Cell Cycle. 2:251-7. Shen, C., A. K. Buck, X. Liu, M. Winkler, and S. N. Reske. 2003. Gene silencing by adenovirus-delivered siRNA. FEBS Lett. 539:111-4.

Peptide delivery: Morris, M. C., L. Chaloin, F. Heitz, and G. Divita. 2000. Translocating peptides and proteins and their use for gene delivery. Curr Opin Biotechnol. 11:461-6. Simeoni, F., M. C. Morris, F. Heitz, and G. Divita. 2003. Insight into the mechanism of the peptide-based gene delivery system MPG: implications for delivery of siRNA into mammalian cells. Nucleic Acids Res. 31:2717-24. Other technologies that may be suitable for delivery of siRNA to the target cells are based on nanoparticles or nanocapsules such as those described in U.S. patent numbers 6,649,192B and 5,843,509B.

Inhibition of IL-11-Mediated Signalling

In embodiments of the present invention, agents capable of inhibiting the action of IL-11 may possess one or more of the following functional properties:

Inhibition of signalling mediated by IL-11;
Inhibition of signalling mediated by binding of IL-11 to IL-11Rα:gp130 receptor complex;
Inhibition of signalling mediated by binding of IL-11:IL-11Rα complex to gp130 (i.e. IL-11 trans signalling);
Inhibition of a process mediated by IL-11;
Inhibition of gene/protein expression of IL-11 and/or IL-11Rα.

These properties can be determined by analysis of the relevant agent in a suitable assay, which may involve comparison of the performance of the agent to suitable control agents. The skilled person is able to identify an appropriate control conditions for a given assay.

IL-11-mediated signalling and/or processes mediated by IL-11 includes signalling mediated by fragments of IL-11 and polypeptide complexes comprising IL-11 or fragments thereof. IL-11-mediated signalling may be signalling mediated by human IL-11 and/or mouse IL-11. Signalling mediated by IL-11 may occur following binding of IL-11 or an IL-11 containing complex to a receptor to which IL-11 or said complex binds.

In some embodiments, an agent may be capable of inhibiting the biological activity of IL-11 or an IL-11-containing complex.

In some embodiments, the agent is an antagonist of one or more signalling pathways which are activated by signal transduction through receptors comprising IL-11Rα and/or gp130, e.g. IL-11Rα:gp130. In some embodiments, the agent is capable of inhibiting signalling through one or more immune receptor complexes comprising IL-11Rα and/or gp130, e.g. IL-11Rα:gp130. In various aspects of the present invention, an agent provided herein is capable of inhibiting IL-11-mediated cis and/or trans signalling. In some embodiments in accordance with the various aspects of the present invention an agent provided herein is capable of inhibiting IL-11-mediated cis signalling.

In some embodiments, the agent may be capable of inhibiting IL-11-mediated signalling to less than 100%, e.g. one of 99% or less, 95% or less, 90% or less, 85% or less, 80/6 or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the agent (or in the presence of an appropriate control agent). In some embodiments, the agent is capable of reducing IL-11-mediated signalling to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the agent (or in the presence of an appropriate control agent).

In some embodiments, the IL-11-mediated signalling may be signalling mediated by binding of IL-11 to IL-11Rα:gp130 receptor. Such signalling can be analysed e.g. by treating cells expressing IL-11Rα and gp130 with IL-11, or by stimulating IL-11 production in cells which express IL-11Rα and gp130.

The $IC_{50}$ for an agent for inhibition of IL-11-mediated signalling may be determined, e.g. by culturing Ba/F3 cells expressing IL-11Rα and gp130 in the presence of human IL-11 and the agent, and measuring 3H-thymidine incorporation into DNA. In some embodiments, the agent may exhibit an $IC_{50}$ of 10 µg/ml or less, preferably one of ≤5 µg/ml, ≤4 µg/ml, ≤3.5 µg/ml, ≤3 µg/ml, ≤2 µg/ml, ≤1 µg/ml, ≤0.9 µg/ml, ≤0.8 µg/ml, ≤0.7 µg/ml, ≤0.6 µg/ml, or ≤0.5 µg/ml in such an assay.

In some embodiments, the IL-11-mediated signalling may be signalling mediated by binding of IL-11:IL-11Rα complex to gp130. In some embodiments, the IL-11:IL-11Rα complex may be soluble, e.g. complex of extracellular domain of IL-11Rα and IL-11, or complex of soluble IL-11Rα isoform/fragment and IL-11. In some embodiments, the soluble IL-11Rα is a soluble (secreted) isoform of IL-11Rα, or is the liberated product of proteolytic cleavage of the extracellular domain of cell membrane bound IL-11Rα.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα, e.g. hyper IL-11. Hyper IL-11 was constructed using fragments of IL-11Rα (amino acid residues 1 to 317 consisting of domain 1 to 3; UniProtKB: 014626) and IL-11 (amino acid residues 22 to 199 of UniProtKB: P20809) with a 20 amino acid long linker (SEQ ID NO:20). The amino acid sequence for Hyper IL-11 is shown in SEQ ID NO:21.

In some embodiments, the agent may be capable of inhibiting signalling mediated by binding of IL-11:IL-11Rα complex to gp130, and is also capable of inhibiting signalling mediated by binding of IL-11 to IL-11Rα:gp130 receptor.

In some embodiments, the agent may be capable of inhibiting a process mediated by IL-11.

In some embodiments, the agent may be capable of inhibiting gene/protein expression of IL-11 and/or IL-11Rα. Gene and/or protein expression can be measured as described herein or by methods in the art that will be well known to a skilled person.

In some embodiments, the agent may be capable of inhibiting gene/protein expression of IL-11 and/or IL-11Rα to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of expression in the absence of the agent (or in the presence of an appropriate control agent). In some embodiments, the agent is capable of inhibiting gene/protein expression of IL-11 and/or IL-11Rα to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, 50.55 times, ≤0.5 times, ≤0.45 times, ≤0.4 times, ≤0.35 times, ≤0.3 times, ≤0.25 times, ≤0.2 times, ≤0.15 times, ≤0.1 times the level of expression in the absence of the agent (or in the presence of an appropriate control agent).

Treatment/Prevention of Kidney Injury

The present invention provides methods and articles (agents and compositions) for the treatment/prevention of kidney injury, e.g. as described herein and disorders, diseases or conditions associated with kidney injury.

Treatment is achieved by inhibition of IL-11-mediating signalling (i.e. antagonism of IL-11-mediated signalling). That is, the present invention provides for the treatment/prevention of kidney injury and disorders, diseases and conditions associated with kidney injury through inhibition of IL-11 mediated signalling, in e.g. a cell, tissue/organ/organ system/subject. In some embodiments, inhibition of IL-11-mediated signalling in accordance with the present disclosure comprises inhibition of IL-11-mediated signalling in cells of the kidney (e.g. tubule epithelial cells).

Provided is an agent capable of inhibiting interleukin 11 (IL-11)-mediated signalling for use in a method of treating or preventing kidney injury and/or a disorder, disease or condition associated with kidney injury.

Also provided is use of an agent capable of inhibiting interleukin 11 (IL-11)-mediated signalling for use in the manufacture of a medicament for use in a method of treating or preventing kidney injury and/or a disorder, disease or condition associated with kidney injury.

Further provided is a method of treating or preventing kidney injury and/or a disorder, disease or condition associated with kidney injury, the method comprising administering to a subject in need of treatment a therapeutically effective amount of an agent capable of inhibiting interleukin 11 (IL-11)-mediated signalling.

In some embodiments, the present invention provides for the treatment/prevention of kidney injury-related pathology in a disease/condition. That is, the present invention provides for the treatment/prevention of a disease/condition in which kidney injury is pathologically implicated. Kidney injury-related pathology is described herein. In particular, relevant pathology includes damage to tubular epithelial cells, either proximal, distal or both.

Agents capable of inhibiting interleukin 11 (IL-11)-mediated signalling are moreover demonstrated herein to be capable of reversing kidney injury. That is, inhibition of IL-11 mediated signalling is shown to be able to improve renal function following kidney injury.

Accordingly, the present invention contemplates to employ antagonists of IL-11 mediated signalling to enhance/improve renal function in subjects having impaired renal function. e.g. as a consequence of kidney injury.

Agents capable of inhibiting interleukin 11 (IL-11)-mediated signalling are useful for promoting the proliferation TECs, for the generation of functional, renal tissue. Thus agents capable of inhibiting interleukin 11 (IL-11)-mediated signalling are provided herein for promoting the proliferation, survival and/or function of tubular epithelial cells (TECs), and/or the growth, maintenance and/or function of renal tissue.

Agents capable of inhibiting interleukin 11 (IL-11)-mediated signalling are provided herein for regenerating tubular epithelial cells (TECs), and/or renal tissue.

The epithelial and/or acta to mesenchymal cell phenotype transition (also referred to herein as 'EMT') by tubular epithelial cells is associated with reduced kidney function. EMT by TECs is induced by soluble factors produced following tissue injury, such as TGFB1. Antagonism of IL-11 mediated signalling is shown herein to inhibit the EMT by TECs, and thereby preserve/improve renal function.

Expression of SNAIL is implicated in the loss of the ability of TECs to proliferate, and EMT. IL-11-mediated signalling is demonstrated herein to have a central role in upregulating SNAIL expression. Accordingly, the present invention contemplates to employ antagonists of IL-11 mediated signalling to inhibit SNAIL expression, e.g. in TECs. Antagonism of IL-11-mediated signalling releases TECs from SNAIL-mediated inhibition of TEC proliferation.

Accordingly, the present invention contemplates to employ antagonists of IL-11 mediated signalling to preserve/increase the number/proportion of cells in the kidney having a TEC phenotype. TEC phenotype may be characterised e.g. by E-cadherin expression. The present invention contemplates to employ antagonists of IL-11 mediated signalling to reduce the number/proportion of cells in the kidney having a mesenchymal cell-like phenotype. A mesenchymal cell-like phenotype may be characterised e.g. by SNAIL and/or ACTA2 expression, optionally with lack of E-cadherin expression.

Antagonists of IL-11 mediated signalling may be used in methods to preserve/increase the level of a function of TECs or renal tissue. TEC/renal tissue function may be evaluated e.g. by evaluation of a correlate of such activity. For example, TEC/renal tissue function may be evaluated by analysing the level of urea and/or creatine in the serum/blood (e.g. blood urea nitrogen), or by monitoring the albumin to creatine ratio (ACR). Antagonists of IL-11 mediated signalling may be used in methods to reduce the level of creatine and/or urea in the serum/blood, or to reduce ACR.

It will be clear to the person skilled in the art that the therapeutic and prophylactic utility of the present invention extends to essentially any disease/condition which would benefit from a reduction in kidney injury and/or kidney injury-related pathology. The therapeutic and prophylactic utility of the present invention extends to any subject suffering from kidney injury and/or a disorder, disease or condition associated with kidney injury. The therapeutic and prophylactic utility of the present invention also extends to any subject suffering from a disease in which kidney injury-related pathology is present.

In some embodiments, the present invention provides for the treatment/prevention of diseases/conditions that are caused/exacerbated by kidney injury. In some embodiments, there is provided the treatment/prevention of diseases/conditions in a subject in which kidney injury provides a poor prognosis.

Diagnosis and management of acute kidney injury is described in Rahman M et al., Acute Kidney injury: a guide to diagnosis and management. Am Fam Physician 2012 Oct. 1:86(7): 631-9. As described therein, acute kidney injury is characterized by abrupt deterioration in kidney function, manifested by an increase in serum creatinine level with or without reduced urine output.

In some embodiments, kidney injury and/or a disorder, disease or condition associated with kidney injury to be treated/prevented may be characterised by an increase in one or more of the following in an organ/tissue/subject affected by kidney injury and/or a disorder, disease or condition associated with kidney injury e.g. as compared to normal organ/tissue/subject (i.e. without kidney injury or a disorder, disease or condition associated with kidney injury): expression of one or more of IL-11, and IL-11Rα.

In some embodiments, the present invention provides for the treatment/prevention of kidney injury in the context of a disease/disorder/condition associated with kidney injury e.g. as described herein. In some embodiments, the present invention provides for the treatment/prevention of kidney injury and an underlying disease/disorder/condition associated with kidney injury. For example, inhibition of IL-11-mediated signalling has utility in antagonising the role of IL-11 in chemotherapy-associated kidney injury, as well as antagonising the role of IL-11 in the cancer itself.

Treatment/prevention of kidney injury and/or a disorder, disease or condition associated with kidney injury according to the present invention may be of kidney injury and/or a disorder, disease or condition associated with kidney injury that is associated with an upregulation of IL-11, e.g. an upregulation of IL-11 in cells or tissue in which the symptoms of the disease/disorder/condition manifests or may occur, or upregulation of extracellular IL-11 or IL-11Rα.

The disorder, disease or condition associated with kidney injury may affect any tissue or organ or organ system. In some embodiments, the disease/disorder/condition may affect several tissues/organs/organ systems. In some embodiments, the disease/disorder/condition affects the kidney.

In some embodiments, the disorder, disease or condition associated with kidney injury affects one or more of: the cardiovascular system, the digestive system, the excretory system, the respiratory system, the renal system, the reproductive system, the circulatory system, the muscular system, the endocrine system, the exocrine system, the lymphatic system, the immune system, the nervous system, and/or the skeletal system.

In some embodiments, the present invention provides for the treatment/prevention of kidney injury-related pathology in acute kidney injury, nephrotoxicity, drug-induced kidney injury, drug-induced acute kidney injury, drug-induced nephrotoxicity, cisplatin-induced kidney injury, cisplatin-induced acute kidney injury, cisplatin-induced nephrotoxicity.

Treatment may be effective to prevent progression of kidney injury and/or a disorder, disease or condition associated with kidney injury, e.g. to reduce/delay/prevent worsening of, or to reduce/delay/prevent development of, kidney injury and/or a disorder, disease or condition associated with kidney injury. In some embodiments treatment may lead to an improvement, e.g. a reduction in the severity of, and/or a reversal of, the symptoms of kidney injury and/or a disorder, disease or condition associated with kidney injury. In some embodiments treatment may increase survival. In some embodiments treatment is effective to reverse the effects and/or symptoms of kidney injury and/or a disorder, disease or condition associated with kidney injury.

Prevention may refer to prevention of development of kidney injury and/or a disorder, disease or condition associated with kidney injury, and/or prevention of worsening of kidney injury and/or a disorder, disease or condition associated with kidney injury, e.g. prevention of progression of kidney injury and/or a disorder, disease or condition associated with kidney injury to a later or chronic stage.

In some embodiments, the present invention provides for the treatment/prevention of acute kidney injury (AKI), acute kidney failure, acute kidney disease, chronic kidney disease, kidney damage, drug-induced kidney injury, tubular necrosis, acute tubular necrosis, autoimmune kidney injury and cancer.

Acute tubular necrosis is the most common type of intrinsic acute kidney injury in hospitalized patients (Rahman M et al supra). The cause is often ischemic (from prolonged hypotension) or nephrotoxic (from an agent that is toxic to the tubular cells). Acute kidney injury caused by acute tubular necrosis often does not improve with adequate repletion of intravascular volume and blood flow to the kidneys. Both ischemic and nephrotoxic acute tubular necrosis can resolve over time, although temporary renal replacement therapy may be required, depending on the degree of renal injury and the presence of preexisting chronic kidney disease.

A "cancer" as referred to herein may be any unwanted cell proliferation (or any disease manifesting itself by unwanted cell proliferation), neoplasm or tumour or increased risk of or predisposition to the unwanted cell proliferation, neoplasm or tumour. The cancer may be benign or malignant and may be primary or secondary (metastatic). A neoplasm or tumour may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node (including abdominal lymph node, axillary lymph node, cervical lymph node, inguinal lymph node, mediastinal lymph node, pelvic lymph node, periaortic lymph node), lymphoblast, maxilla, mediastinum, mesentery, myometrium, nasopharynx, omentume, oral cavity, ovary, pancreas, parotid gland, peripheral nervous system peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Cancers may be of a particular type. Examples of types of cancer include astrocytoma, carcinoma (e.g. adenocarcinoma, hepatocellular carcinoma, medullary carcinoma, papillary carcinoma, squamous cell carcinoma), glioma, lymphoma, medulloblastoma, melanoma, myeloma, meningioma, neuroblastoma, sarcoma (e.g. angiosarcoma, chrondrosarcoma, osteosarcoma).

A "cancer" as used herein can comprise any one or more of the following: acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and Wilms' tumor.

In accordance with various aspects of the present invention, the methods may comprise one or more of the following (e.g. in the context of kidney injury):

Reducing necrosis of renal tissue and/or renal cells;
Reducing fibrosis of the kidney and/or renal tissue;
Reducing collagen content of, and/or inhibiting collagen deposition in, the kidney and/or renal
tissue;
Increasing/maintaining renal function;
Increasing/maintaining urine output;
Reducing urinary albumin/creatinine ratio;
Reducing serum creatinine level;
Reducing serum urea level;
Reducing serum TGFβ1 level;
Increasing/maintaining kidney weight;
Increasing/maintaining renal cortical volume;
Increasing/maintaining body weight;
Inhibiting epithelial-to-mesenchymal cell transition of tubule epithelial cells;
Reducing the number/proportion of ACTA2+ve cells in the kidney;
Reducing SNAIL expression by renal cells and/or in the kidney/renal tissue; and
Increasing/maintaining E-cadherin expression by renal cells and/or in the kidney/renal tissue.

Administration

Administration of an agent capable of inhibiting IL-11-mediated signalling is preferably in a "therapeutically effective" or "prophylactically effective" amount, this being sufficient to show benefit to the subject.

In some embodiments, the agent may be administered before, in conjunction with, or after the cause of the kidney injury, e.g. administration or consumption of a nephrotoxic medicine or exposure to an environmental source of kidney injury.

The actual amount administered, and rate and time-course of administration, will depend on the nature and severity of the kidney injury and the nature of the agent. Prescription of treatment, e.g. decisions on dosage etc., is within the responsibility of general practitioners and other medical doctors, and typically takes account of the disease/condition to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Multiple doses of the agent may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

In therapeutic applications, agents capable of inhibiting IL-11-mediated signalling are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio.

Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for topical, parenteral, systemic, intravenous, intra-arterial, intramuscular, intrathecal, intraocular, intra-conjunctival, subcutaneous, oral or transdermal routes of administration which may include injection. Injectable formulations may comprise the selected agent in a sterile or isotonic medium. The formulation and mode of administration may be selected according to the agent and disease/disorder/condition to be treated.

In some cases, an article (e.g. agent/composition) as described herein is administered for treatment as described herein in conjunction with treatment for a disease/disorder/condition associated with kidney injury. Suitable treatments for a disease/disorder/condition associated with kidney injury are known in the art. A composition may be administered alone or in combination with other treatments, either simultaneously or sequentially dependent upon the disease/disorder/condition to be treated. For example, the article may be administered before, at the same time as, or after the treatment. The article and the treatment may be formulated together, e.g. in a formulation described above, or formulated separately.

Detection of IL-11 and Receptors for IL-11

Some aspects and embodiments of the present invention concern detection of expression of IL-11 or a receptor for IL-11 (e.g. IL-11Rα, gp130, or a complex containing IL-11Rα and/or gp130) in a sample obtained from a subject.

In some aspects and embodiments the present invention concerns the upregulation of expression (over-expression) of IL-11 or a receptor for IL-11 (as a protein or oligonucleotide encoding the respective IL-11 or receptor for IL-11) and detection of such upregulation as an indicator of suitability for treatment with an agent capable of inhibiting the action of IL-11 or with an agent capable of preventing or reducing the expression of IL-11 or a receptor for IL-11.

Upregulated expression comprises expression at a level that is greater than would normally be expected for a cell or tissue of a given type. Upregulation may be determined by measuring the level of expression of the relevant factor in a cell or tissue. Comparison may be made between the level of expression in a cell or tissue sample from a subject and a reference level of expression for the relevant factor, e.g. a value or range of values representing a normal level of expression of the relevant factor for the same or corresponding cell or tissue type. In some embodiments reference levels may be determined by detecting expression of IL-11 or a receptor for IL-11 in a control sample, e.g. in corresponding cells or tissue from a healthy subject or from healthy tissue of the same subject. In some embodiments reference levels may be obtained from a standard curve or data set.

Levels of expression may be quantitated for absolute comparison, or relative comparisons may be made.

In some embodiments upregulation of IL-11 or a receptor for IL-11 (e.g. IL-11Rα, gp130, or a complex containing IL-11Rα and/or gp130) may be considered to be present when the level of expression in the test sample is at least 1.1 times that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that of the reference level.

Expression levels may be determined by one of a number of known in vitro assay techniques, such as PCR based assays, in situ hybridisation assays, flow cytometry assays, immunological or immunohistochemical assays.

By way of example suitable techniques involve a method of detecting the level of IL-11 or a receptor for IL-11 in a sample by contacting the sample with an agent capable of binding IL-11 or a receptor for IL-11 and detecting the formation of a complex of the agent and IL-11 or receptor for IL-11. The agent may be any suitable binding molecule, e.g. an antibody, polypeptide, peptide, oligonucleotide, aptamer or small molecule, and may optionally be labelled to permit detection, e.g. visualisation, of the complexes formed.

Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5), isotope markers, radioisotopes (e.g. 32P, 33P, 35S), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

Assays may be configured to quantify the amount of IL-11 or receptor for IL-11 in a sample. Quantified amounts of IL-11 or receptor for IL-11 from a test sample may be compared with reference values, and the comparison used to determine whether the test sample contains an amount of IL-11 or receptor for IL-11 that is higher or lower than that of the reference value to a selected degree of statistical significance.

Quantification of detected IL-11 or receptor for IL-11 may be used to determine up- or down-regulation or amplification of genes encoding IL-11 or a receptor for IL-11. In cases where the test sample contains fibrotic cells, such up-regulation, down-regulation or amplification may be compared to a reference value to determine whether any statistically significant difference is present.

A sample obtained from a subject may be of any kind. A biological sample may be taken from any tissue or bodily fluid, e.g. a blood sample, blood-derived sample, serum sample, lymph sample, semen sample, saliva sample, synovial fluid sample. A blood-derived sample may be a selected fraction of a patient's blood, e.g. a selected cell-containing fraction or a plasma or serum fraction. A sample may comprise a tissue sample or biopsy; or cells isolated from a subject. Samples may be collected by known techniques, such as biopsy or needle aspirate. Samples may be stored and/or processed for subsequent determination of IL-11 expression levels.

Samples may be used to determine the upregulation of IL-11 or receptor for IL-11 in the subject from which the sample was taken.

In some preferred embodiments a sample may be a tissue sample, e.g. biopsy, taken from kidney tissue, cardiac tissue, visceral organ tissue, respiratory system organ tissue, or urinary/renal system tissue. A sample may contain cells.

A subject may be selected for therapy/prophylaxis in accordance with the present invention based on determination that the subject has an upregulated level of expression of IL-11 or of a receptor for IL-11 (e.g. IL-11Rα, gp130, or a complex containing IL-11Rα and/or gp130). Upregulated expression of IL-11 or of a receptor for IL-11 may serve as a marker of kidney injury and/or a disorder, disease or condition associated with kidney injury suitable for treatment with an agent capable of inhibiting IL-11 mediated signalling.

Upregulation may be in a given tissue or in selected cells from a given tissue. A preferred tissue may be kidney/renal tissue. Upregulation of expression of IL-11 or of a receptor for IL-11 may also be determined in a circulating fluid, e.g. blood, or in a blood derived sample. Upregulation may be of extracellular IL-11 or IL-11Rα. In some embodiments expression may be locally or systemically upregulated.

Following selection, a subject may be administered with an agent capable of inhibiting IL-11 mediated signalling.

Diagnosis and Prognosis

Detection of upregulation of expression of IL-11 or a receptor for IL-11 (e.g. IL-11Rα, gp130, or a complex containing IL-11Rα and/or gp130) may also be used in a method of diagnosing kidney injury and/or a disorder, disease or condition associated with kidney injury, identifying a subject at risk of developing kidney injury and/or a disorder, disease or condition associated with kidney injury, and in methods of prognosing or predicting a subject's response to treatment with an agent capable of inhibiting IL-11 mediated signalling.

"Developing", "development" and other forms of "develop" may refer to the onset of a disorder/disease, or the continuation or progression of a disorder/disease.

In some embodiments a subject may be suspected of having or suffering from kidney injury and/or a disorder, disease or condition associated with kidney injury, e.g. based on the presence of other symptoms indicative of kidney injury and/or a disorder, disease or condition associated with kidney injury in the subject's body or in selected cells/tissues of the subject's body, or be considered at risk of developing kidney injury and/or a disorder, disease or condition associated with kidney injury, e.g. because of genetic predisposition or exposure to environmental conditions, known to be risk factors for kidney injury and/or a disorder, disease or condition associated with kidney injury. Determination of upregulation of expression of IL-11 or a receptor for IL-11 may confirm a diagnosis or suspected diagnosis, or may confirm that the subject is at risk of developing kidney injury and/or a disorder, disease or condition associated with kidney injury. The determination may also diagnose kidney injury and/or a disorder, disease or condition associated with kidney injury or predisposition as one suitable for treatment with an agent capable of inhibiting IL-11-mediated signalling.

As such, a method of providing a prognosis for a subject having, or suspected of having kidney injury and/or a disorder, disease or condition associated with kidney injury may be provided, the method comprising determining whether the expression of IL-11 or a receptor for IL-11 is upregulated in a sample obtained from the subject and, based on the determination, providing a prognosis for treatment of the subject with an agent capable of inhibiting IL-11-mediated signalling.

In some aspects, methods of diagnosis or methods of prognosing or predicting a subject's response to treatment with an agent capable of inhibiting IL-11-mediated signalling may not require determination of the expression of IL-11 or a receptor for IL-11, but may be based on determining genetic factors in the subject that are predictive of upregulation of expression or activity. Such genetic factors may include the determination of genetic mutations, single nucleotide polymorphisms (SNPs) or gene amplification in IL-11, IL-11Rα and/or gp130 which are correlated with and/or predictive of upregulation of expression or activity and/or IL-11 mediated signalling. The use of genetic factors to predict predisposition to a disease state or response to treatment is known in the art, e.g. see Peter Stärkel Gut 2008; 57:440-442; Wright et al., Mol. Cell. Biol. March 2010 vol. 30 no. 6 1411-1420.

Genetic factors may be assayed by methods known to those of ordinary skill in the art, including PCR based assays, e.g. quantitative PCR, competitive PCR. By determining the presence of genetic factors, e.g. in a sample obtained from a subject, a diagnosis may be confirmed, and/or a subject may be classified as being at risk of developing kidney injury and/or a disorder, disease or condition associated with kidney injury, and/or a subject may be identified as being suitable for treatment with an agent capable of inhibiting IL-11 mediated signalling.

Some methods may comprise determination of the presence of one or more SNPs linked to secretion of IL-11 or susceptibility to development of kidney injury and/or a disorder, disease or condition associated with kidney injury. SNPs are usually bi-allelic and therefore can be readily determined using one of a number of conventional assays known to those of skill in the art (e.g. see Anthony J. Brookes. The essence of SNPs. Gene Volume 234, Issue 2, 8 Jul. 1999, 177-186; Fan et al., Highly Parallel SNP Genotyping. Cold Spring Harb Symp Quant Biol 2003. 68: 69-78; Matsuzaki et al., Parallel Genotyping of Over 10,000 SNPs using a one-primer assay on a high-density oligonucleotide array. Genome Res. 2004. 14: 414-425).

The methods may comprise determining which SNP allele is present in a sample obtained from a subject. In some embodiments determining the presence of the minor allele may be associated with increased IL-11 secretion or susceptibility to development of kidney injury and/or a disorder, disease or condition associated with kidney injury.

Accordingly, in one aspect of the present invention a method for screening a subject is provided, the method comprising:

obtaining a nucleic acid sample from the subject;

determining which allele is present in the sample at the polymorphic nucleotide position of one or more of the SNPs listed in FIG. 33, FIG. 34, or FIG. 35 of WO 2017/103108 A1 (incorporated by reference herein), or a SNP in linkage disequilibrium with one of the listed SNPs with an $r^2 \geq 0.8$.

The determining step may comprise determining whether the minor allele is present in the sample at the selected polymorphic nucleotide position. It may comprise determining whether 0, 1 or 2 minor alleles are present.

The screening method may be, or form part of, a method for determining susceptibility of the subject to development of kidney injury and/or a disorder, disease or condition associated with kidney injury, or a method of diagnosis or prognosis as described herein.

The method may further comprise the step of identifying the subject as having susceptibility to, or an increased risk of, developing kidney injury and/or a disorder, disease or condition associated with kidney injury, e.g. if the subject is determined to have a minor allele at the polymorphic nucleotide position. The method may further comprise the step of selecting the subject for treatment with an agent capable of inhibiting IL-11 mediated signalling and/or administering an agent capable of inhibiting IL-11 mediated signalling to the subject in order to provide a treatment for kidney injury and/or a disorder, disease or condition associated with kidney injury in the subject or to prevent development or progression of kidney injury and/or a disorder, disease or condition associated with kidney injury in the subject.

In some embodiments, a method of diagnosing kidney injury and/or a disorder, disease or condition associated with kidney injury, identifying a subject at risk of developing kidney injury and/or a disorder, disease or condition associated with kidney injury, and methods of prognosing or predicting a subject's response to treatment with an agent capable of inhibiting IL-11 mediated signalling employs an indicator that is not detection of upregulation of expression of IL-11 or a receptor for IL-11, or genetic factors.

In some embodiments, a method of diagnosing kidney injury and/or a disorder, disease or condition associated with kidney injury, identifying a subject at risk of developing kidney injury and/or a disorder, disease or condition associated with kidney injury, and methods of prognosing or predicting a subject's response to treatment with an agent capable of inhibiting IL-11 mediated signalling is based on detecting, measuring and/or identifying one or more of the following indicators or performing one of the following analyses:

Elevated serum creatinine, blood urea and/or nitrogen

Urinary sodium and creatinine levels

Reduced urine output

Renal ultrasonography to identify presence/absence of tubular obstruction

Renal biopsy

Performing urinalysis.

Reference levels for laboratory kidney tests can be found in e.g. Rahman et al supra, which is hereby incorporated by reference in its entirety.

Methods of diagnosis or prognosis may be performed in vitro on a sample obtained from a subject, or following processing of a sample obtained from a subject. Once the sample is collected, the patient is not required to be present for the in vitro method of diagnosis or prognosis to be performed and therefore the method may be one which is not practised on the human or animal body. The sample obtained from a subject may be of any kind, as described herein above.

Other diagnostic or prognostic tests may be used in conjunction with those described here to enhance the accuracy of the diagnosis or prognosis or to confirm a result obtained by using the tests described here.

Subjects

Subjects may be animal or human. Subjects are preferably mammalian, more preferably human. The subject may be a non-human mammal, but is more preferably human. The subject may be male or female. The subject may be a patient. The patient may have kidney injury and/or a disorder, disease or condition associated with kidney injury as described herein. A subject may have been diagnosed with kidney injury and/or a disorder, disease or condition associated with kidney injury requiring treatment, may be suspected of having such kidney injury and/or a disorder, disease or condition associated with kidney injury, or may be at risk from developing kidney injury and/or a disorder, disease or condition associated with kidney injury.

In embodiments according to the present invention the subject is preferably a human subject. In embodiments according to the present invention, a subject may be selected for treatment according to the methods based on characterisation for certain markers of kidney injury and/or a disorder, disease or condition associated with kidney injury.

In some embodiments the subject may be a subject who is being administered a drug or medicine in order to treat a disease, condition or disorder that may or may not be manifest in kidney tissue. The subject may have developed a drug-induced kidney injury as a consequence, e.g. side-effect, of such treatment. The subject may be selected for treatment or preventative therapy according to this invention on the basis of having developed such drug-induced kidney injury.

In some embodiments, the subject may have received treatment with a chemotherapeutic agent, or may be receiving treatment with a chemotherapeutic agent. The subject may have, be suspected of having, or be in recovery or remission from, cancer and administration of the chemotherapeutic agent may form part of the subject's treatment. Accordingly, the subject may be a subject having chemotherapeutic agent-induced kidney injury, chemotherapeutic agent-induced acute kidney injury or chemotherapeutic agent-induced nephrotoxicity.

In some preferred embodiments, the subject may have received treatment with cisplatin, or may be receiving treatment with cisplatin. The subject may have, be suspected of having, or be in recovery or remission from, cancer and administration of cisplatin may form part of the subject's treatment. Accordingly, the subject may be a subject having cisplatin-induced kidney injury, cisplatin-induced acute kidney injury or cisplatin-induced nephrotoxicity.

A subject may optionally be receiving intermittent or regular dialysis.

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, *Bioinformatics* 21, 951-960), T-coffee (Notredame et al. 2000, *J. Mol. Biol.* (2000)

302, 205-217), Kalign (Lassmann and Sonnhammer 2005, *BMC Bioinformatics*, 6(298)) and MAFFT (Katoh and Standley 2013, *Molecular Biology and Evolution*, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Human IL-11 (UniProt P20809) | MNCVCRLVLVVLSLWPDTAVAPGPPPGPPPRVSPDPRAELDSTVLLTRSLLADTRQLA AQLRDKFPADGDHNLDSLPTLAMSAGALGALQLPGVLTRLRADLLSYLRHVQWLRRA GGSSLKTLEPELGTLQARLDRLLRRLQLLMSRLALPQPPPDPPAPPLAPPSSAWGGI RAAHAILGGLHLTLDWAVRGLLLLKTRL |
| 2 | Human gp130 (UniProt P40189-1) | MLTLQTWLVQALFIFLTTESTGELLDPCGYISPESPVVQLHSNFTAVCVLKEKCMDY HFVNANYIVWKTNHFTIPKEQYTIINRTASSVTFTDIASLNIQLTCNILTFGQLEQN VYGITIISGLPPEKPKNLSCIVNEGKKMRCEWDGGRETHLETNFTLKSEWATHKFAD CKAKRDTPTSCTVDYSTVYFVNIEVWVEAENALGKVTSDHINFDPVYKVKPNPPHNL SVINSEELSSILKLTWTNPSIKSVIILKYNIQYRTKDASTWSQIPPEDTASTRSSFT VQDLKPFTEYVFRIRCMKEDGKGYWSDWSEEASGITYEDRPSKAPSFWYKIDPSHTQ GYRTVQLVWKTLPPFEANGKILDYEVTLTRWKSHLQNYTVNATKLTVNLTNDRYLAT LTVRNLVGKSDAAVLTIPACDFQATHPVMDLKAFPKDNMLWVEWTTPRESVKKYILE WCVLSDKAPCITDWQQEDGTVHRTYLRGNLAESKCYLITVTPVYADGPGSPESIKAY LKQAPPSKGPTVRTKKVGKNEAVLEWDQLPVDVQNGFIRNYTIFYRTIIGNETAVNV DSSHTEYTLSSLTSDTLYMVRMAAYTDEGGKDGPEFTFTTPKFAQGEIEAIVVPVCL AFLLTTLLGVLFCFNKRDLIKKHIWPNVPDPSKSHIAQWSPHTPPRHNFNSKDQMYS DGNFTDVSVVEIEANDKKPFPEDLKSLDLFKKEKINTEGHSSGIGGSSCMSSSRPSI SSSDENESSQNTSSTVQYSTVVHSGYRHQVPSVQVFSRSESTQPLLDSEERPEDLQL VDHVDGGDGILPRQQYFKQNCSQHESSPDISHFERSKQVSSVNEEDFVRLKQQISDH ISQSCGSGQMKMFQEVSAADAFGPGTEGQVERFETVGMEAATDEGMPKSYLPQTVRQ GGYMPQ |
| 3 | Human IL11 RA (UniProt Q14626) | MSSSCSGLSRVLVAVATALVSASSPCPQAWGPPGVQYGQPGRSVKLCCPGVTAGDPV SWFRDGEPKLLQGPDSGLGHELVLAQADSTDEGTYICQTLDGALGGTVTLQLGYPPA RPVVSCQAADYENFSCTWSPSQISGLPTRYLTSYRKKTVLGADSQRRSPSTGPWPCP QDPLGAARCWHGAEFWSQYRINVTEVNPLGASTRLLDVSLQSILRPDPPQGLRVESV PGYPRRLRASWTYPASWPCQPHFLLKFRLQYRPAQHPAWSTVEPAGLEEVITDAVAG LPHAVRVSARDFLDAGTWSTWSPEAWGTPSTGTIPKEIPAWGQLHTQPEVEPQVDSP APPRPSLQPHPRLLDHRDSVEQVAVLASLGILSFLGLVAGALALGLWLRLRRGGKDG SPKPGFLASVIPVDRRPGAPNL |
| 4 | siRNA target IL-11 | CCTTCCAAAGCCAGATCTT |
| 5 | siRNA target IL-11 | GCCTGGGCAGGAACATATA |
| 6 | siRNA target IL-11 | CCTGGGCAGGAACATATAT |
| 7 | siRNA target IL-11 | GGTTCATTATGGCTGTGTT |
| 8 | siRNA target IL-11 Ra | GGACCATACCAAAGGAGAT |
| 9 | siRNA target IL-11 Ra | GCGTCTTTGGGAATCCTTT |
| 10 | siRNA target IL-11 Ra | GCAGGACAGTAGATCCCT |
| 11 | siRNA target IL-11 Ra | GCTCAAGGAACGTGTGTAA |
| 12 | siRNA to IL-11 (NM_000641.3) | CCUUCCAAAGCCAGAUCUUdTdT-AAGAUCUGGCUUUGGAAGGdTdT |
| 13 | siRNA to IL-11 (NM_000641.3) | GCCUGGGCAGGAACAUAUAdTdT-UAUAUGUUCCUGCCCAGGCdTdT |
| 14 | siRNA to IL-11 (NM_000641.3) | CCUGGGCAGGAACAUAUAUdTdT-AUAUAUGUUCCUGCCCAGGdTdT |
| 15 | siRNA to IL-11 (NM_000641.3) | GGUUCAUUAUGGCUGUGUUdTdT-AACACAGCCAUAAUGAACCdTdT |
| 16 | siRNA to IL-11 Ra (U32324.1) | GGACCAUACCAAAGGAGAUdTdT-AUCUCCUUUGGUAUGGUCCdTdT |
| 17 | siRNA to IL-1 1 Ra (U32324.1) | GCGUCUUUGGGAAUCCUUUdTdT-AAAGGAUUCCCAAAGACGCdTdT |
| 18 | siRNA to IL-11 Ra (U32324.1) | GCAGGACAGUAGAUCCCUAdTdT-UAGGGAUCUACUGUCCUGCdTdT |
| 19 | siRNA to IL-11 Ra (U32324.1) | GCUCAAGGAACGUGUGUAAdTdT-UUACACACGUUCCUUGAGCdTdT |
| 20 | 20 amino acid linker | GPAGQSGGGGSGGGSGGGSV |
| 21 | Hyper IL-11 (IL-11RA: IL-11 fusion) | MSSSCSGLSRVLVAVATALVSASSPCPQAWGPPGVQYGQPGRSVKLCCPGVTAGDPV SWFRDGEPKLLQGPDSGLGHELVLAQADSTDEGTYICQTLDGALGGTVTLQLGYPPA RPVVSCQAADYENFSCTWSPSQISGLPTRYLTSYRKKTVLGADSQRRSPSTGPWPCP QDPLGAARCVVHGAEFWSQYRINVTEVNPLGASTRLLDVSLQSILRPDPPQGLRVES VPGYPRRLRASWTYPASWPCQPHFLLKFRLQYRPAQHPAWSTVEPAGLEEVITDAVA |

| SEQ ID NO: | DESCRIPTION | SEQUENCE |
|---|---|---|
| | | GLPHAVRVSARDFLDAGTWSTWSPEAWGTPSTGPAGQSGGGGSGGGSGGGSVPGPP PGPPRVSPDPRAELDSTVLLTRSLLADTRQLAAQLRDKFPADGDHNLDSLPTLAMSA GALGALQLPGVLTRLRADLLSYLRHVQWLRRAGGSSLKTLEPELGTLQARLDRLLRR LQLLMSRLALPQPPPDPPAPPLAPPSSAWGGIRAAHAILGGLHLTLDWAVRGLLLLK TRL |
| 22 | Enx203 VH | EVQLQQSGPELVKPGASVKIPCKASGYTFTDYNMDWVKQSHGKSLEWIGDINPHNGG PIYNQKFTGKATLTVDKSSSTAYMELRSLTSEDTAVYYCARGELGHWYFDVWGTGTT VTVSS |
| 23 | Enx203 VL | DIVLTQSPASLAVSLGQRATISCRASKSVSTSGYSYIHWYQQKPGQPPKLLIYLASN LDSGVPARFSGSGSGTDFTLNIHPVEEEDAATYYCQHSRDLPPTFGGGTKLEIK |
| 24 | Enx209 VH | QVQLQQPGAELVRPGSSVKLSCKASGYTFTNYWMHWLKQRPVQGLEWIGNIGPSDSK THYNQKFKDKATLTVDKSSSTAYMQLNSLTSEDSAVYYCARGDYVLFTYWGQGTLVT VSA |
| 25 | Enx209 VL | DIVLTQSPATLSLSPGERATLSCRASQSISNNLHWYQQKSHEAPRLLIYASQSISGI PARFSGSGSGTDFTLSFSSLETEDFAVYFCQQSYSWPLTFGQGTKLEIK |
| 26 | Enx108A VH | QVQLVQSGGGWQPGRSLRLSCAASGFTFSSYGMHWVRQAPGKGLEWVAVISYDGSNK YYADSVKGRFTISRDNSKNTLYLQMNSLRAEDTAVYYCAKIGATDPLDYWGQGTLVT VSS |
| 27 | Enx108.A VL | QSALTQPRSVSGSPGQSVTLSCTGTSSDVGGYNYVSWYQHYPGKAPKLMIFDVNERS SGVPDRFSGSKSGNTASLTiSGLQAEDEADYYCASYAGRYTWMFGGGTKVTVLG |
| 28 | EnxA hIgG4 (L248E, S241P) HC | QVQLVQSGGGWQPGRSLRLSCAASGFTFSSYGMHWVRQAPGKGLEWVAVISYDGSNK YYADSVKGRFTISRDNSKNTLYLQMNSLRAEDTAVYYCAKIGATDPLDYWGQGTLVT VSSASTKGPSVFPLAPCSRSTSESTAALGCLVKDYFPEPVTVSWNSGALTSGVHTFP AVLQSSGLYSLSSVVTVPSSSLGTKTYTCNVDHKPSNTKVDKRVESKYGPPCPPCPA PEFEGGPSVFLFPPKPKDTLMiSRTPEVTCVWDVSQEDPEVQFNWYVDGVEVHNAKT KPREEQFNSTYRVVSVLTVLHQDWLNGKEYKCKVSNKGLPSSIEKTISKAKGQPREP QVYTLPPSQEEMTKNQVSLTCLVKGFYPSDIAVEWESNGQPENNYKTTPPVLDSDGS FFLYSRLTVDKSRWQEGNVFSCSVMHEALHNHYTQKSLSLSLGK |
| 29 | Enx108A lambda LC | QSALTQPRSVSGSPGQSVTLSCTGTSSDVGGYNYVSWYQHYPGKAPKLMIFDVNERS SGVPDRFSGSKSGNTASLTISGLQAEDEADYYCASYAGRYTWMFGGGTKVTVLGQPK AAPSVILFPPSSEELQANKATLVCLISDFYPGAVTVAWKADSSPVKAGVETTTPSKQ SNNKYAASSYLSLTPEQWKSHRSYSCQVTHEGSTVEKTVAPTECS |
| 30 | hEnx203 VH | EVQLVQSGAEVKKPGASVKISCKASGYTFTDYNMDWVKQAPGQRLEWIGDINPHNGG PIYNQKFTGRATLTVDKSASTAYMELSSLRSEDTAVYYCARGELGHWYFDVWGQGTT VTVSS |
| 31 | hEnx203 VL | DIVLTQSPASLALSPGERATLSCRASKSVSTSGYSYIHWYQQKPGQAPRLLIYLASN LDSGVPARFSGSGSGTDFTLTISSLEEEDFATYYCQHSRDLPPTFGQGTKLEIK |
| 32 | hEnx209 VH | QVQLVQSGAEVKKPGASVKVSCKASGYTFTNYWMHWLRQRPGQGLEWIGNIGPSDSK THYNQKFKDRVTMTVDKSTSTAYMELSSLRSEDTAVYYCARGDYVLFTYWGQGTLVT VSS |
| 33 | hEnx209 VL | DIVLTQSPATLSLSPGERATLSCRASQSISNNLHWYQQKPGQAPRLLIKYASQSISG IPARFSGSGSGTDFTLTISSLEPEDFAVYYCQQSYSWPLTFGQGTKLEIK |
| 34 | Enx108A VH CDR1 | SYGMH |
| 35 | Enx108A VH CDR2 | VISYDGSNKYYADSVKG |
| 36 | Enx108A VH CDR3 | IGATDPLDY |
| 37 | Enx108A VL CDR1 | TGTSSDVGGYNYVS |
| 38 | Enx108A VL CDR2 | DVNERSS |
| 39 | Enx108A VL CDR3 | ASYAGRYTWM |
| 40 | Enx203, hEnx203 VH CDR1 | DYNMD |
| 41 | Enx203, hEnx203 VH CDR2 | DINPHNGGPIYNQKFTG |

| SEQ ID NO: | DESCRIPTION | SEQUENCE |
|---|---|---|
| 42 | Enx203, hEnx203 VH CDR3 | GELGHWYFDV |
| 43 | Enx203, hEnx203 VL CDR1 | RASKSVSTSGYSYIH |
| 44 | Enx203, hEnx203 VL CDR2 | LASNLDS |
| 45 | Enx203, hEnx203 VL CDR3 | QHSRDLPPT |
| 46 | Enx209, hEnx209 VH CDR1 | NWMH |
| 47 | Enx209, hEnx209 VH CDR2 | NIGPSDSKTHYNQKFKD |
| 48 | Enx209, hEnx209 VH CDR3 | GDYVLFTY |
| 49 | Enx209, hEnx209 VL CDR1 | RASQSISNNLH |
| 50 | Enx209, hEnx209 VL CDR2 | YASQSIS |
| 51 | Enx209, hEnx209 VL CDR3 | QQSYSWPLT |
| 52 | Human IGHG1 constant (K214R, D356E, L358M) | ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKRVEPKSCDKTHTCPPCPA PELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGK |
| 53 | Human IGHG4 constant (L248E, S241P) | ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPEF EGGPSVFLFPPKPKDTLMISRTPEVTCVVVDVSQEDPEVQFNWYVDGVEVHNAKTKPR EEQFNSTYRVVSVLTVLHQDWLNGKEYKCKVSNKGLPSSIEKTISKAKGQPREPQVY TLPPSQEEMTKNQVSLTCLVKGFYPSDIAVEWESNGQPENNYKTTPPVLDSDGSFFL YSRLTVDKSRWQEGNVFSCSVMHEALHNHYTQKSLSLSLGK |
| 54 | Human IGKC constant | RTVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC |
| 55 | Human IGLC2 constant | GQPKAAPSVTLFPPSSEELQANKATLVCLISDFYPGAVTVAWKADSSPVKAGVETTT PSKQSNNKYAASSYLSLTPEQWKSHRSYSCQVTHEGSTVEKTVAPTECS |
| 56 | hEnx203 hIgG1 HC | EVQLVQSGAEVKKPGASVKISCKASGYTFTDYNMDWVKQAPGQRLEWIGDINPHNGG PIYNQKFTGRATLTVDKSASTAYMELSSLRSEDTAVYYCARGELGHWYFDVWGQGTT VTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKRVEPKSCDKTHTC PPCPAPELLGGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISKAK GQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 57 | hEnx203 kappa LC | DIVLTQSPASLALSPGERATLSCRASKSVSTSGYSYIHWYQQKPGQAPRLLIYLASN LDSGVPARFSGSGSGTDFTLTISSLEEEDFATYYCQHSRDLPPTFGQGTKLEIKRTV AAPSVFIFPPSDEQLKSGTASVVCLLNNFYPREAKVQWKVDNALQSGNSQESVTEQD SKDSTYSLSSTLTLSKADYEKHKVYAGEVTHQGLSSPVTKSFNRGEC |
| 58 | hEnx209 hIgG4 (L248E, S241P) HC | QVQLVQSGAEVKKPGASVKVSCKASGYTFTNYWMHWLRQRPGQGLEWIGNIGPSDSK THYNQKFKDRVTMTVDKSTSTAYMELSSLRSEDTAVYYCARGDYVLFTYWGQGTLVT VSSASTKGPSVFPLAPCSRSTSESTAALGCLVKDYFPEPVTVSWNSGALTSGVHTFP AVLQSSGLYSLSSVVTVPSSSLGTKTYTCNVDHKPSNTKVDKRVESKYGPPCPPCPA PEFEGGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQPRE PQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGK |

-continued

Sequences

| SEQ ID NO: | DESCRIPTION | SEQUENCE |
|---|---|---|
| 59 | hEnx209 kappa LC | DIVLTQSPATLSLSPGERATLSCRASQSISNNLHWYQQKPGQAPRLLIKYASQSISG IPARFSGSGSGTDFTLTISSLEPEDFAVYYCQQSYSWPLTFGQGTKLEIKRTVAAPS VFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC |

The invention includes the combination of the aspects and preferred features described except where such a combination is clearly impermissible or expressly avoided.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Methods disclosed herein may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

Where a nucleic acid sequence is disclosed herein, the reverse complement thereof is also expressly contemplated.

For standard molecular biology techniques, see Sambrook, J., Russel, D. W. Molecular Cloning, A Laboratory Manual. 3 ed. 2001, Cold Spring Harbor, New York: Cold Spring Harbor Laboratory Press Aspects and embodiments of the present invention will now be discussed with reference to the accompanying figures. Further aspects and embodiments will be apparent to those skilled in the art. All documents mentioned in this text are incorporated herein by reference. While the invention has been described in conjunction with the exemplary embodiments described below, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

BRIEF DESCRIPTION OF THE FIGURES

Embodiments and experiments illustrating the principles of the invention will now be discussed with reference to the accompanying figures.

EXAMPLES

Figure 1:
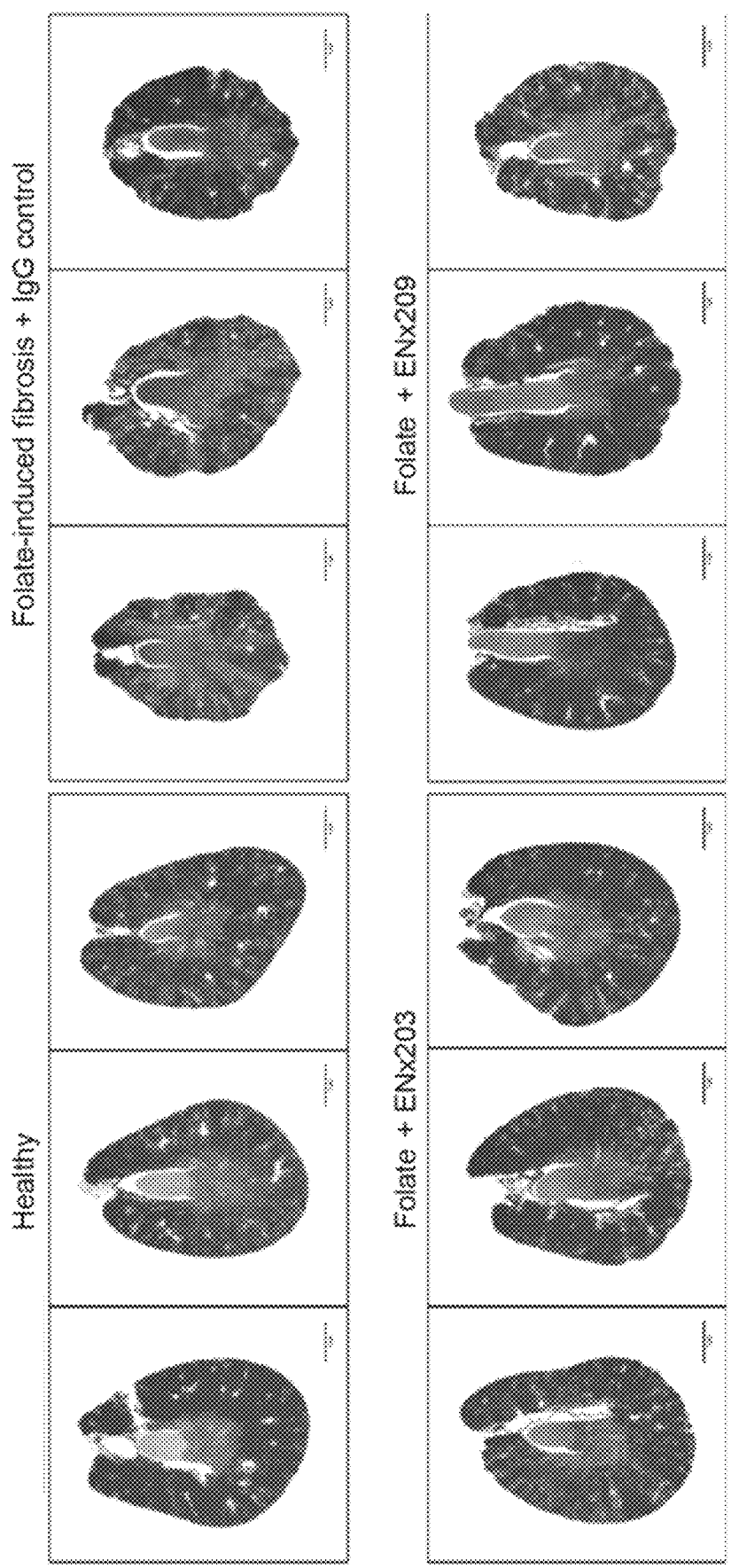
FIG. 1. Micrographs showing neutralising anti-IL-11 antibodies prevent progression from AKI to CKD as compared to IgG control antibody. Mice were subjected to folate induced kidney injury (a model of acute tubular necrosis (ATN) and secondary fibrosis) and administered either IgG control, Enx203 (anti-IL-11 antibody) or ENx209 (anti-IL-11RA antibody). Kidneys were harvested after 28 days and used for Masson's trichrome staining. Both antibodies were remarkably effective at preventing collagen deposition.

In the following examples, the inventors demonstrate that anti-IL-11 therapy can ameliorate kidney injury through extensive regeneration and reversal of renal impairment in models of acute and chronic kidney disease.

Example 1: Materials and Methods 1.1 Primary Human Renal Proximal Tubule Epithelial Cells Culture and Stimulation Conditions Primary human renal proximal tubule epithelial cells (HRPTEC, PCS-400-010, ATCC) were grown and maintained at 37° C. and 5% $CO_2$ in complete renal epithelial cell growth medium (PCS-400-030 and PCS-400-040, ATCC). HRPTEC medium was renewed every 2-3 days and cells were passaged at 80% confluence using standard trypsinization techniques. All the experiments were carried out at P3 and cells were serum-starved for 16 hours prior to respective stimulations (24 hours) that were performed in serum-free renal epithelial cell media. Stimulated cells were compared to unstimulated cells that have been grown for the same duration under the same conditions (serum-free renal epithelial cell media), but without the stimuli.

Operetta Phenotyping Assay

HRPTEC were seeded in 96-well CellCarrier plates (600550, PerkinElmer) at a density of $1\times10^4$ cells per well. Cells were stimulated with the indicated concentrations of IL-11 (Genscript) or TGF-β1 (PHC 143B, Bio-Rad) with and without the presence of 2 μg/ml of either anti IL-11 (ENx203) or IgG isotype control antibodies for 24 hours. Following experimental conditions, cells were fixed in 4% paraformaldehyde (PFA, 28908, Thermo Fisher Scientific), permeabilized with 0.1% Triton X-100 (T8787, Sigma) in PBS. Non-specific binding sites were blocked 0.5% BSA (A7906, Sigma) and 0.1% Tween-20 (170-6531, Bio-Rad) in PBS. Cells were incubated overnight (4 C) with primary antibodies (1:500) i.e. ACTA2 (ab7817, Abcam), Collagen I (34710, Abcam), SNAIL (ab180714, Abcam) and followed by incubation with the appropriate AlexaFluor488-conjugated secondary antibodies (Goat anti-mouse 488, ab150113 and Goat anti-Rabbit 488, ab150077, Abcam) for 1 hour (1:1000, RT, dark). Cells were counter-stained with Rhodamine-Phalloidin (R415, Thermo Fisher Scientific) and DAPI (1 μg/ml, D1306, Thermo Fisher Scientific) in blocking solution. Plates were scanned and images were collected with an Operetta high-content imaging system (1483, PerkinElmer). Each condition was assayed from at least two wells and a minimum of seven fields per well. The quantification of ACTA2+ cells was done using Harmony software version 3.5.2. The measurement of Collagen I fluorescence intensity per area was performed with Columbus version 2.7.1.

1.2 Western Blot

Western blot was carried out on HRPTE total protein extracts. HRPTE were lysed in radioimmunoprecipitation assay (RIPA) buffer containing protease and phosphatase inhibitors (Thermo Scientifics), followed by centrifugation to clear the lysate. Protein concentrations were determined by Bradford assay (Bio-Rad). Equal amount of protein lysates were separated by SDS-PAGE, transferred to PVDF membrane, and subjected to immunoblot analysis for SNAIL (3879, CST) and GAPDH (2118, CST). Proteins were visualized using the ECL detection system (Pierce) with anti-rabbit-HRP (7074, CST).

1.3 Animal Models

All animal procedures were approved and conducted in accordance with the SingHealth Institutional Animal Care and Use Committee (IACUC). All mice were provided food and water ad libitum.

Mouse Model of Chemically Induced-Acute Kidney Injury

Kidney injury was induced by IP injection of folic acid (200 mg/kg) in vehicle (0.3M $NaHCO_3$) to 10 weeks old male mice; control mice were administered vehicle alone. Animals were sacrificed 28 days post-FA. Mice were intraperitoneally injected with anti-IL-11 antibody (ENx203), anti-IL-11Rα antibody (ENx209) or identical concentration of IgG isotype control. Durations of treatment and dosage of antibody therapies are outlined in the figures.

Mouse Model of Surgically Induced-Acute Kidney Injury

Unilateral ureteral obstruction (UUO) surgeries were carried out on 12 weeks old male mice. Briefly, mice were anesthetized by IP injection of ketamine (100 mg/kg)/xylazine (10 mg/kg) and full depth of anaesthesia was accessed with the pedal reflex. Mice were then shaved on the left side of the abdomen. A vertical incision was made through the skin with a scalpel, a second incision was made through the peritoneum to reveal the kidney. Using forceps, the kidney was brought to the surface and the ureter was tied with surgical silk, twice, below the kidney. The ligated kidney was placed gently back into its correct anatomical position and sterile saline was added to replenish loss of fluid. The incisions were then sutured. Animals were post-operatively treated with antibiotic enrofloxacin (15 mg/kg, SC) and analgesic buprenorphine (0.1 mg/kg, SC) for three consecutive days.

1.4 Colorimetric Assays and ELISA

The levels of blood urea nitrogen (BUN) in mouse serum were measured using Urea Assay Kit (ab83362, Abcam). Urine albumin and creatinine levels were measured using Mouse Albumin ELISA kit (ab108792, Abcam) and Creatinine Assay Kit (ab204537, Abcam), respectively. Serum TGFβ1 levels were measured by ELISA. All ELISA and colorimetric assays were performed according to the manufacturer's protocol.

1.5 Histology

Kidney tissues were fixed for 48 h at RT in 10% neutral-buffered formalin (NBF), dehydrated, embedded in paraffin blocks and sectioned at 4 μm. Sections were then stained with Masson's Trichrome according to standard protocol and examined by light microscopy.

Example 2: Analysis of the Effect of Inhibition of IL-11 Mediated Signalling in a Model of Chemically-Induced Kidney Injury Kidney injury was chemically-induced in 10-12 week old littermate mice of similar weight by intraperitoneal (i.p.) injection of folic acid (180 mg $kg^{-1}$) in vehicle (0.3 M $NaHCO_3$); control mice were administered vehicle alone.

Enx203 (an antibody capable of binding to mouse IL-11 (and human IL-11) and inhibiting IL-11 mediated signalling) or Enx209 (an antibody capable of binding to mouse IL-11 (and human IL-11) and inhibiting IL-11 mediated signalling) were administered one day after folic acid treatment, and then 3 times per week at a dose of 20 mg/kg. Mice were euthanized 28 days post-injection.

Enx203 and Enx209 are antagonists of IL-11 mediated signalling. Enx203 is a mouse anti-mouse IL-11 IgG, and is described e.g. in Ng et al., Sci Transl Med. (2019) 11(511) pii: eaaw1237 (also published as Ng, et al., "IL-11 is a therapeutic target in idiopathic pulmonary fibrosis." bioRxiv 336537; doi: https://doi.org/10.1101/336537). Enx203 is also referred to as "X203". Enx203 comprises the VH region according to SEQ ID NO:92 of WO 2019/238882 A1 (SEQ ID NO:22 of the present disclosure), and the VL region according to SEQ ID NO:94 of WO 2019/238882 A1 (SEQ ID NO:23 of the present disclosure). Enx209 is a mouse anti-mouse IL-11Rα IgG, and is described e.g. in Widjaja et al., Gastroenterology (2019) 157(3):777-792 (also published as Widjaja, et al., "IL-11 neutralising therapies target hepatic stellate cell-induced liver inflammation and fibrosis in NASH." bioRxiv 470062; doi: https://doi.org/10.1101/470062). Enx209 is also referred to as "X209". Enx209 comprises the VH region according to SEQ ID NO:7 of WO 2019/238884 A1 (SEQ ID NO:24 of the present disclosure), and the VL region according to SEQ ID NO:14 of WO 2019/238884 A1 (SEQ ID NO:25 of the present disclosure).

The mouse plasma levels of urea and creatinine were quantified using urea assay kit (ab83362, Abcam) and creatinine assay kit (ab65340, Abcam), respectively according to the manufacturer's instructions. The amount of total collagen in the kidney was quantified on the basis of colourimetric detection of hydroxyproline using a Quickzyme Total Collagen assay kit (Quickzyme Biosciences). All colourimetric assays were performed according to the manufacturer's instructions.

Tissues were paraffin-embedded, and kidneys were sectioned at 3 μm. For paraffin sections, tissues were fixed for 24 h, at room temperature in 10% neutral-buffered formalin (Sigma-Aldrich), dehydrated and embedded in paraffin. For cryosections, freshly dissected organs were embedded with Tissue-Tek Optimal Cutting Temperature compound (VWR International). Cryomoulds were then frozen in a metal beaker with isopentane cooled in liquid nitrogen and sections were stored in −80° C. Total collagen was stained with Masson's trichrome stain kit (HT15, Sigma-Aldrich) according to the manufacturer's instructions. Images of the sections were captured and blue-stained areas were semi-quantitatively determined with ImageJ software (version 1.49). For immunohistochemistry, the tissue sections were incubated with anti-ACTA2 antibody (ab5694, Abcam).

Primary antibody staining was visualized using an ImmPRESS HRP Anti-Rabbit IgG Polymer Detection kit (Vector Laboratories) with ImmPACT DAB Peroxidase Substrate (Vector Laboratories) as the chromogen. The sections were then counterstained with Mayer's haematoxylin (Merck).

Figure 2A:
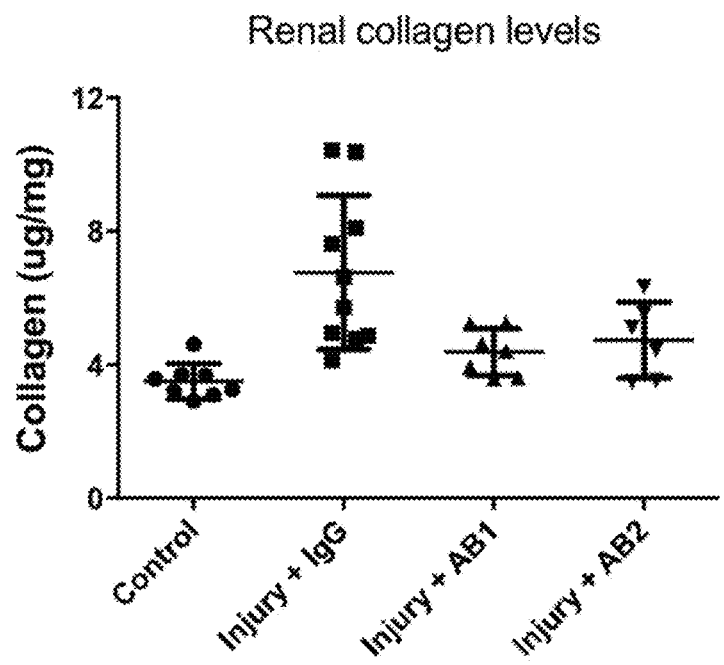
FIGS. 2A and 2B. Charts showing neutralising anti-IL-11 antibodies prevent AKI progression. Mice were subjected to folate induced kidney injury and administered either IgG control or anti-IL-11 antibody (Enx203, AB1) or anti-IL11RA antibody (ENx209, AB2). At 28 days, kidneys were collected for HPA collagen assay and serum urine (collected in metabolic cages) assessed for urinary albumin/creatinine ratios. Note—day 2 makers of kidney injury were similar between treatment groups showing equal levels of initial renal damage but mice receiving anti-IL-11 therapies largely recovered function whereas those receiving IgG less effectively recovered function. (2A) Shows renal collagen content, and (2B) shows urinary albumin/creatinine ratios at day 28 for mice subjected to different treatments.
Figure 2B:
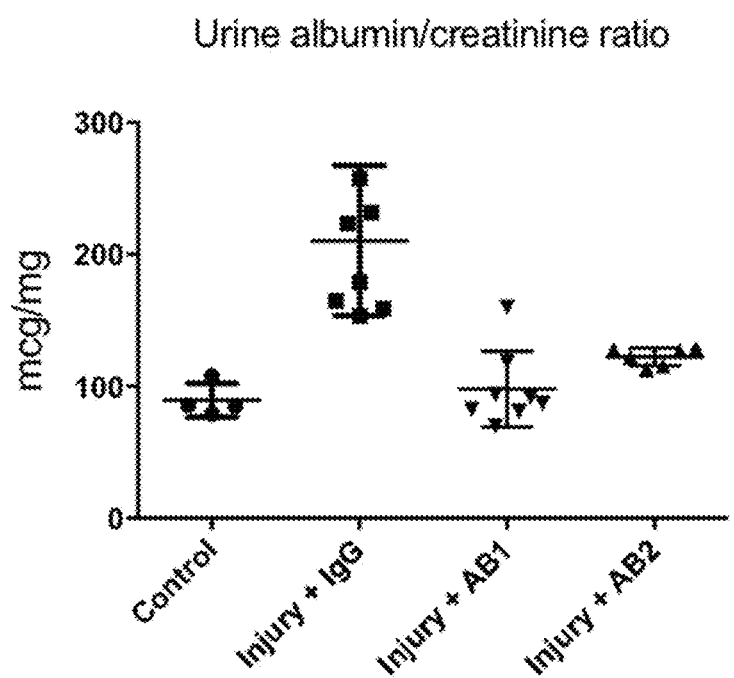

FIGS. 1 and 2 show that mice treated with anti-IL11 antibody or anti-IL-11Rα antibody antagonists were found to have significantly reduced staining for collagen.

FIG. 2 also shows that the urinary albumin/creatine ratio was significantly reduced by treatment with anti-IL-11 antibody or anti-IL-11Rα antibody, indicating a reduced level of kidney damage.

Importantly, the serum levels of urea and creatine at day 2 following chemical induction of kidney damage were similar between treatment groups (data not shown), however mice receiving antagonist IL-11 therapies largely recovered function whereas those receiving IgG less effectively recovered function.

In a separate experiment, a similar folate-induced model of kidney injury was used to evaluate the therapeutic efficacy of antagonists of IL-11 mediated signalling to treat/prevent kidney injury. Mice were treated with folate as described above, and antibodies were administered from one hour prior to injury. Renal collagen content was assessed after 28 days. Animals were treated with 1 mg/kg Enx203 biweekly, 5 mg/kg Enx203 biweekly, 5 mg/kg Enx203 triweekly, 10 mg/kg Enx203 biweekly, 10 mg/kg Enx203 triweekly, 20 mg/kg Enx203 triweekly, 20 mg/kg Enx209 biweekly, or 10 mg/kg or 20 mg/kg IgG control antibody biweekly.

Figure 3:
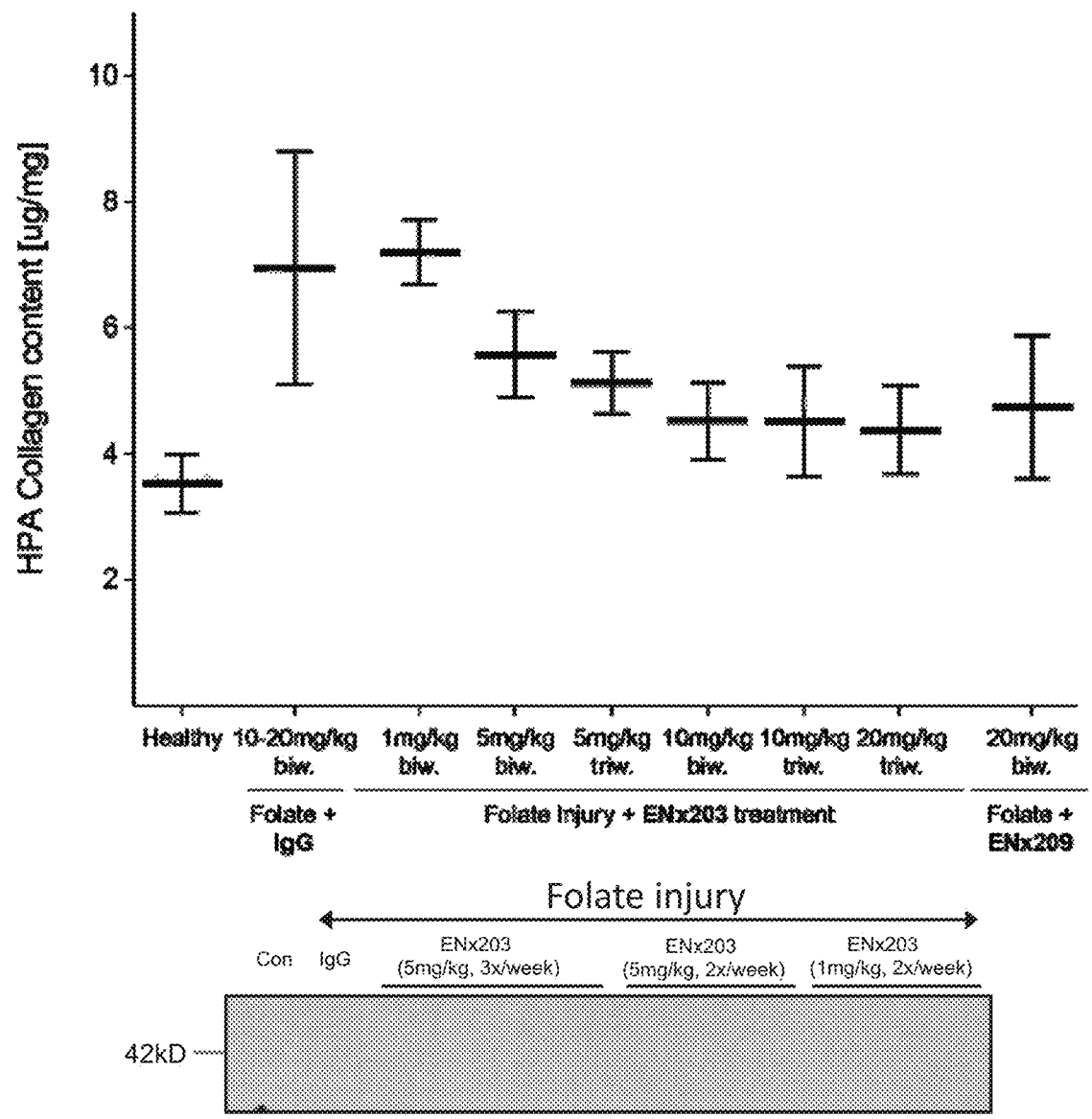
FIG. 3. Graph and image showing dose-dependent effects of ENx203 and ENx209 on kidney injury responses and ERK activation. Animals were treated with folate and antibodies were injected from one hour before injury. Renal collagen content was assessed after 28 days. Animals were treated with either 10 mg/kg or 20 mg/kg biweekly with IgG control antibody. No difference in between groups was observed and animals from both groups are plotted together. The folate model of kidney injury is very severe (see FIG. 4). However, even in the context of the strong chemical stimulus, ENx203 at doses down to 5 mg/kg twice a week was highly effective (upper panel). Individuals points indicate biological replicates. Data is shown as mean±SD. Biweekly (biw.) and triweekly (triw.) injection of antibodies. Monitoring IL-11-mediated ERK activation in the fibrotic kidney as a read out of target engagement (lower panel), the inventors were able to show effects of ExN203 at 1 mg/kg twice a week.

FIG. 3 shows that treatment with the antibody antagonists of IL-11-mediated signalling reduced the levels of collagen content associated with folic acid-induced kidney injury in a dose-dependent fashion. An effect on collagen levels was seen even when Enx203 was administered at 5 mg/kg, biweekly.

Monitoring IL-11-mediated ERK activation in the fibrotic kidney as a read out of target engagement, the inventors demonstrated an effect for ExN203 at a dose of 1 mg/kg, administered twice per week.

Figure 4A:
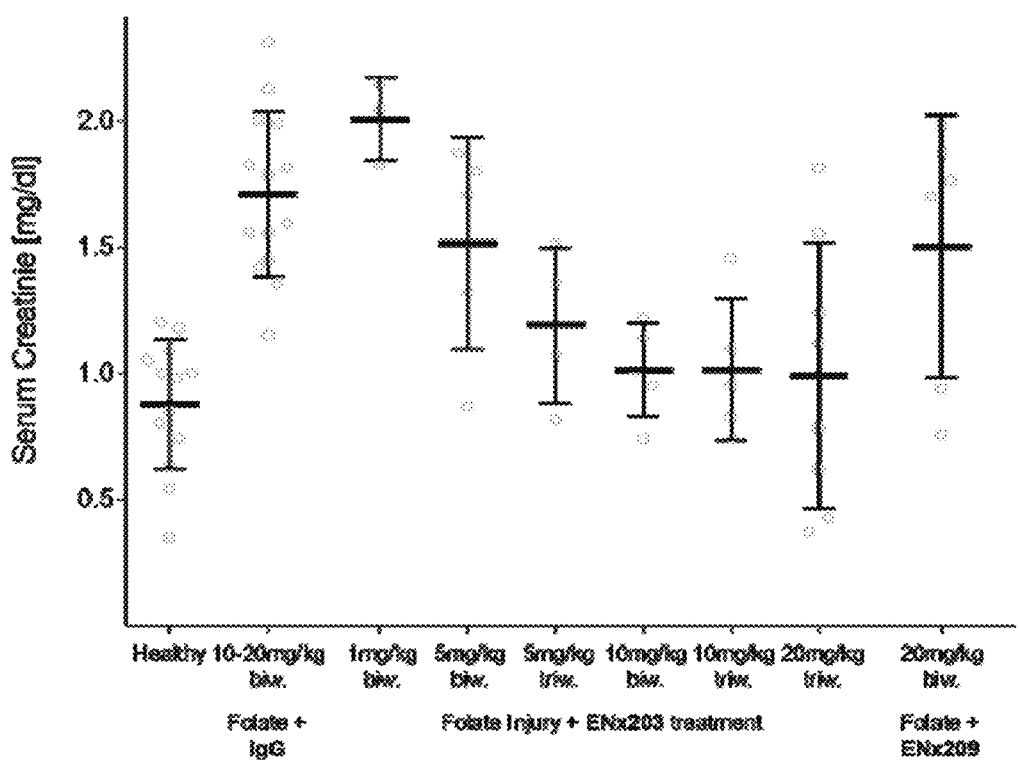
FIGS. 4A to 4C. Graphs showing dose-dependent effects of ENx203 and ENx209 on (4A) serum creatinine, (4B) serum urea and (4C) serum TGFB1 levels. Animals were treated with folate and antibodies were injected from one hour before injury. Serum marker levels were assessed after 28 days. Animals were treated with either 10 mg/kg or 20 mg/kg biweekly with IgG control antibody. No difference in between groups was observed and animals from both groups are plotted together. Individual points indicate biological replicates. Data is shown as mean±SD. Biweekly (biw.) and triweekly (triw.) injection of antibodies.
Figure 4B:
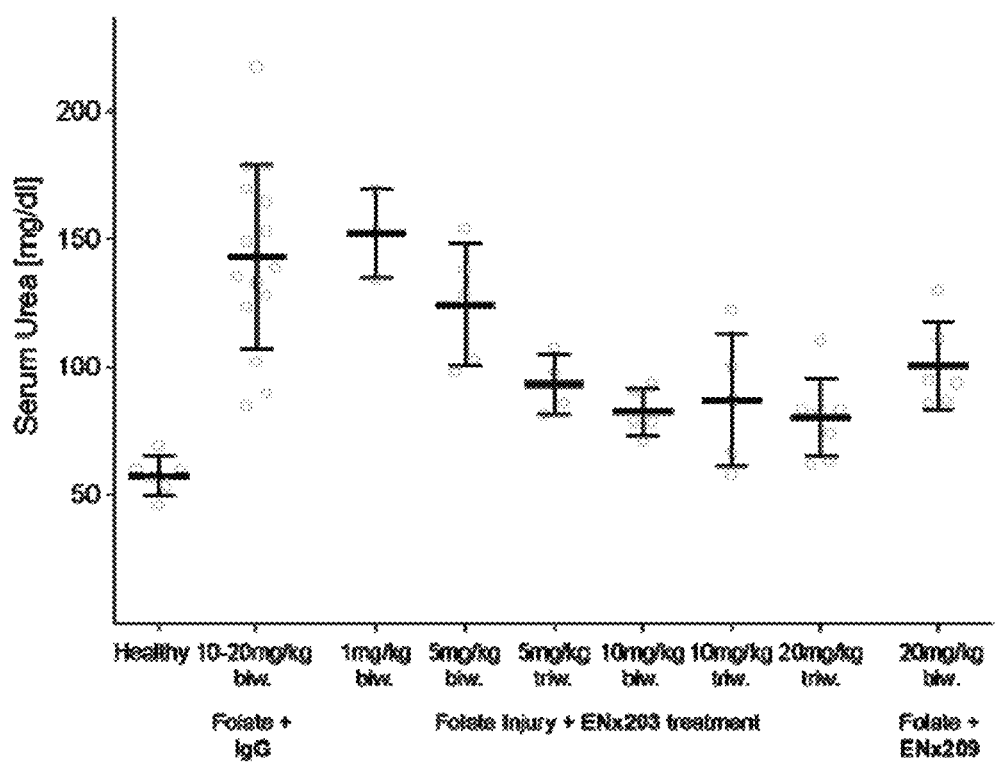
Figure 4C:
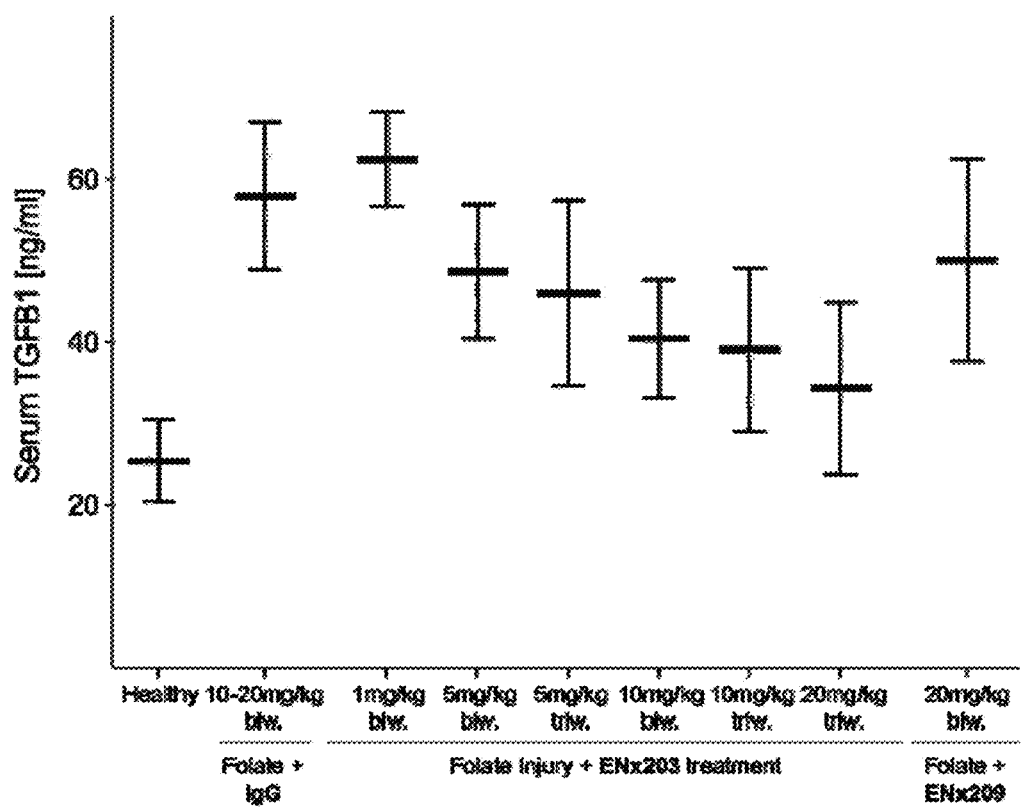

Serum levels of creatine, urea and TGFβ1 were also evaluated in these experiments, and FIG. 4 shows that treatment with the antibody antagonists of IL-11-mediated signalling reduced serum levels of these correlates of kidney injury in a dose-dependent manner. Again, reduction of the levels of these factors in serum was observed even when Enx203 was administered at 5 mg/kg, biweekly.

Figure 5A:
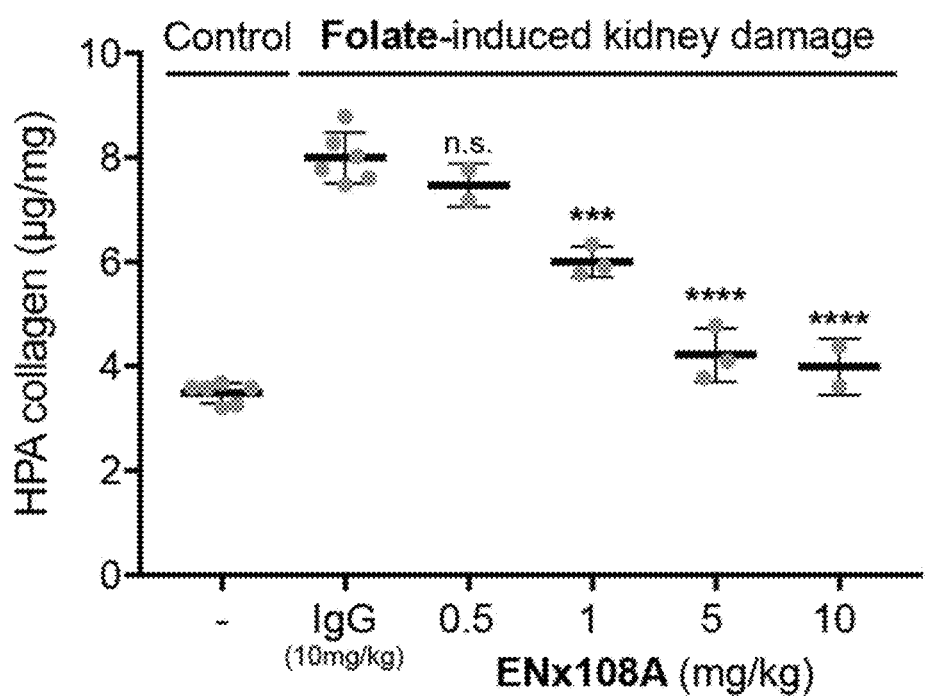
FIGS. 5A to 5C. Graphs showing the effects of treatment with (5A) ENx108A (IgG1), (5B) ENx203 or (5C) ENx209 on AKI progression. Mice were treated with folate and from 1 day before were also treated with antibodies at given concentrations (biweekly). Renal collagen content was determined 21 days after kidney injury. Data points indicate individual animals and all data was generated in parallel, so individual antibodies can be compared with each other. Identical baseline and IgG control animals are plotted for each antibody to facilitate data interpretation. Data are mean+–s.d.; Points indicate animals per group. Two-tailed Dunnett's test, corrected P-values.
Figure 5B:
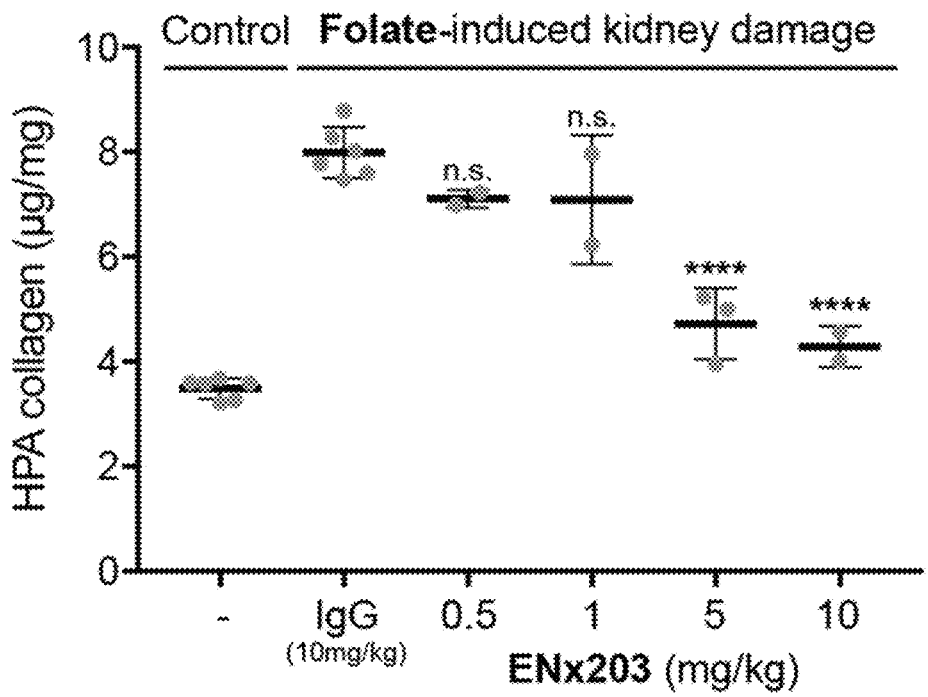
Figure 5C:
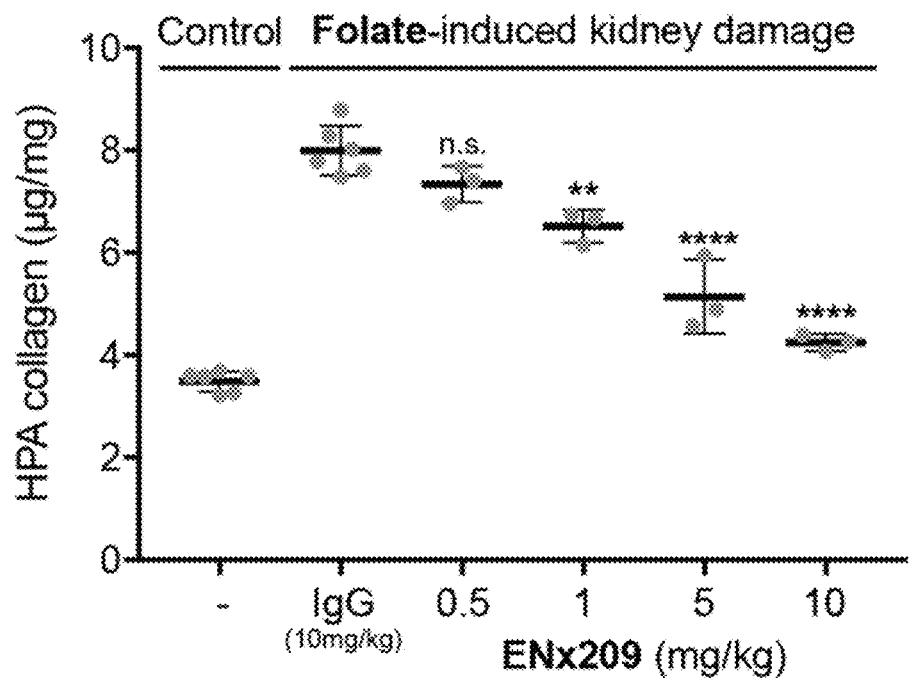

In further experiments, a similar folate-induced model of kidney injury was used to evaluate the therapeutic efficacy of antagonists of IL-11 mediated signalling to treat/prevent kidney injury. Mice were treated with folate as described above, and antibodies were administered from one day prior to injury. Renal collagen content was assessed after 21 days. Animals were administered biweekly with 10 mg/kg IgG control antibody, or 0.5 mg/kg, 1 mg/kg, 5 mg/kg or 10 mg/kg of Enx203, Enx209 or Enx108A. The results are shown in FIG. 5.

Enx108A is a human anti-human IL-11 IgG capable of binding to mouse IL-11 and human IL-11, and inhibiting IL-11 mediated signalling. Enx108A is described e.g. in WO 2019/238882 A1, and comprises the VH region according to SEQ ID NO:8 of WO 2019/238882 A1 (SEQ ID NO:26 of the present disclosure), and the VL region according to SEQ ID NO:20 of WO 2019/238882 A1 (SEQ ID NO:27 of the present disclosure). In the present Example, Enx108A is provided in hIgG4 (L248E, S241P), lambda light format (i.e. is formed of the heavy chain having the amino acid sequence shown in SEQ ID NO:28, and the light chain having the amino acid sequence shown in SEQ ID NO:29).

Figure 6A:
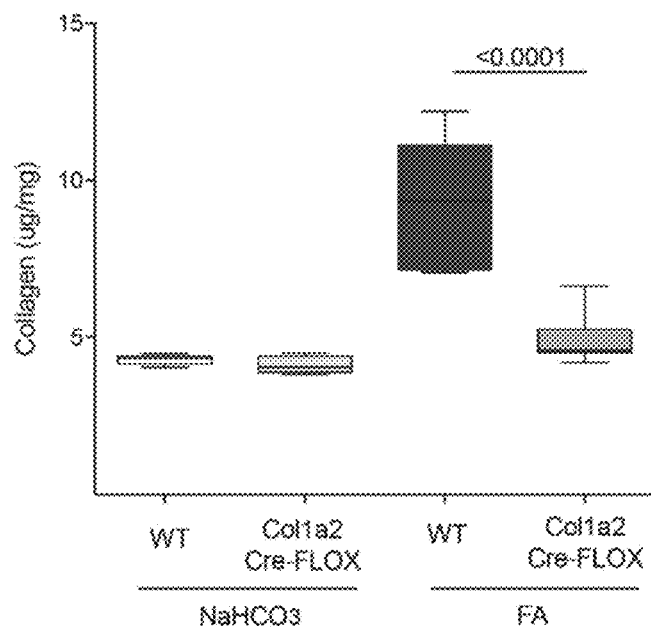
FIGS. 6A and 6B. Graphs showing that fibroblast-specific knock out of Il11ra in mice protects from AKI. Animals were treated with tamoxifen to delete Il11ra1 from Col1a1+ve cells prior to renal injury with folate. After 21 days (6A) collagen content was assessed using the HPA assay and (6B) kidney function was determined via serum urea levels. Animals were protected to similar levels as during antibody treatment, suggesting a central role of IL-11 activity on fibroblasts in the pathogenesis of renal injury and dysfunction. Sidak corrected P-value.
Figure 6B:
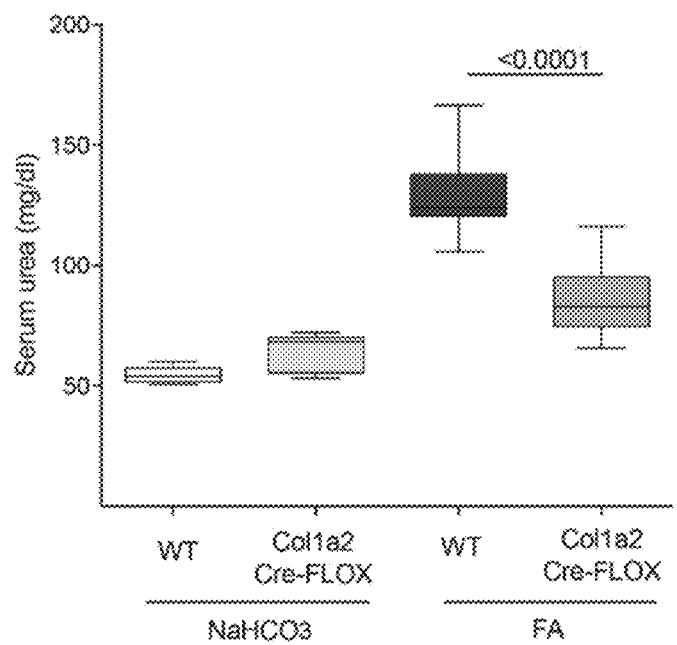
Figure 7A:
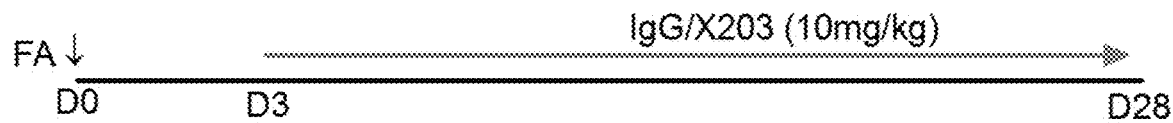
FIGS. 7A to 7F. Schematic, graphs, and image relating to the effect of anti-IL-11 therapy from day 3 post AKI. (7A) Schematic representation of the timing of folate administration and antibody treatment. (7B) Mice receiving anti-IL-11 therapy gain weight soon after receiving anti-IL-11 therapy. (7C) At the end of the study period mice receiving anti-IL-11 therapy had higher kidney weights, (7D) less renal collagen, (7E) normal urine outputs and (7F) improved gross morphology as compared to mice receiving IgG.
Figure 7B:
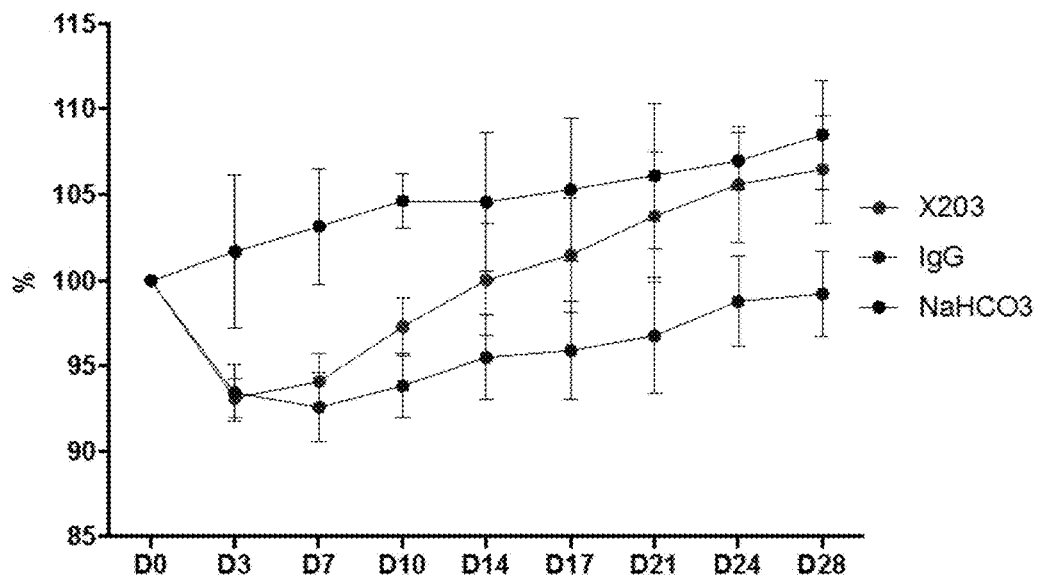
Figure 7C:
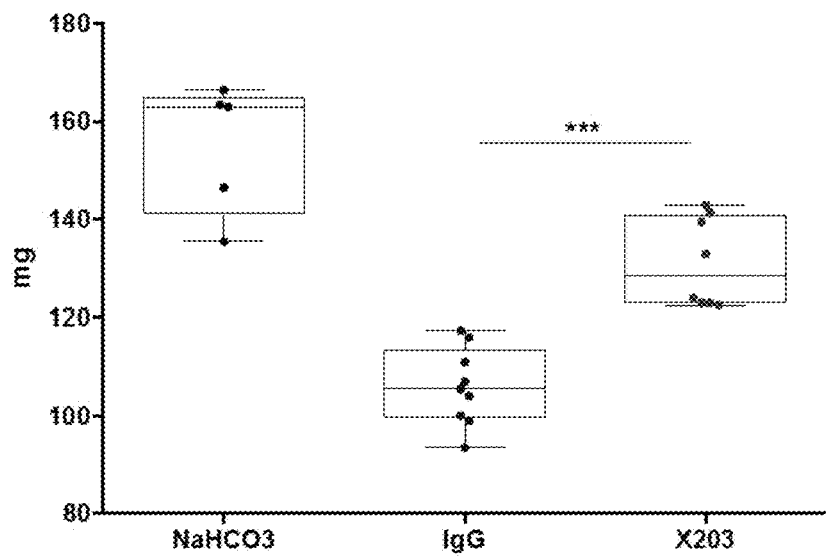
Figure 7D:
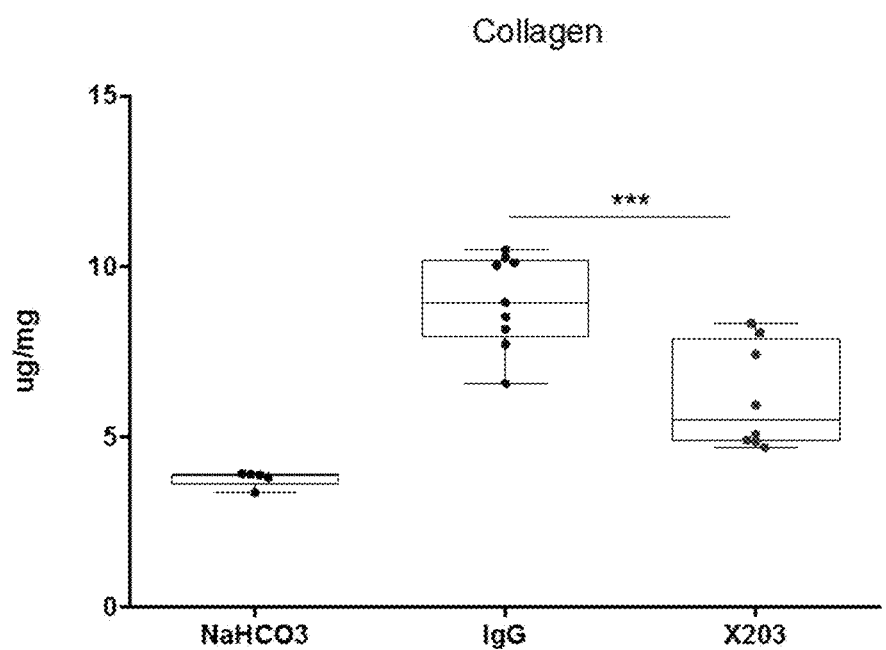
Figure 7E:
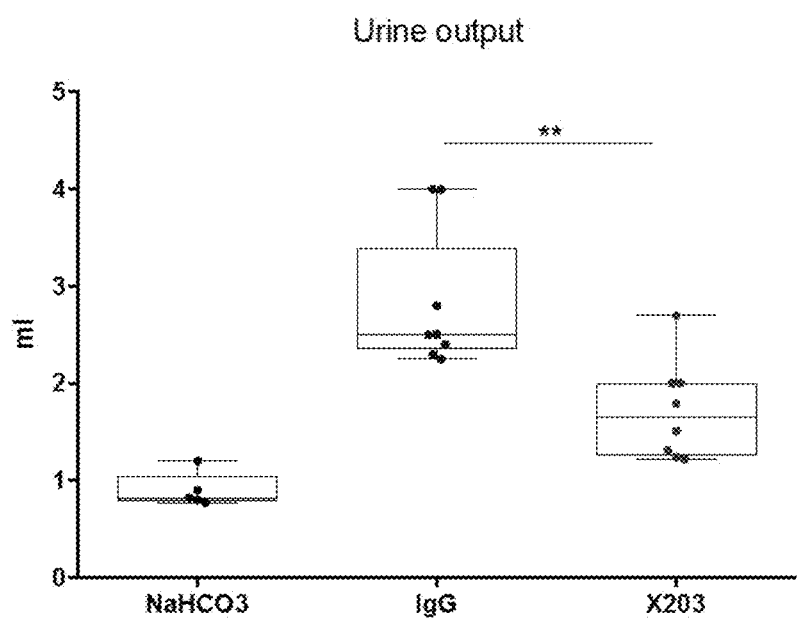
Figure 7F:
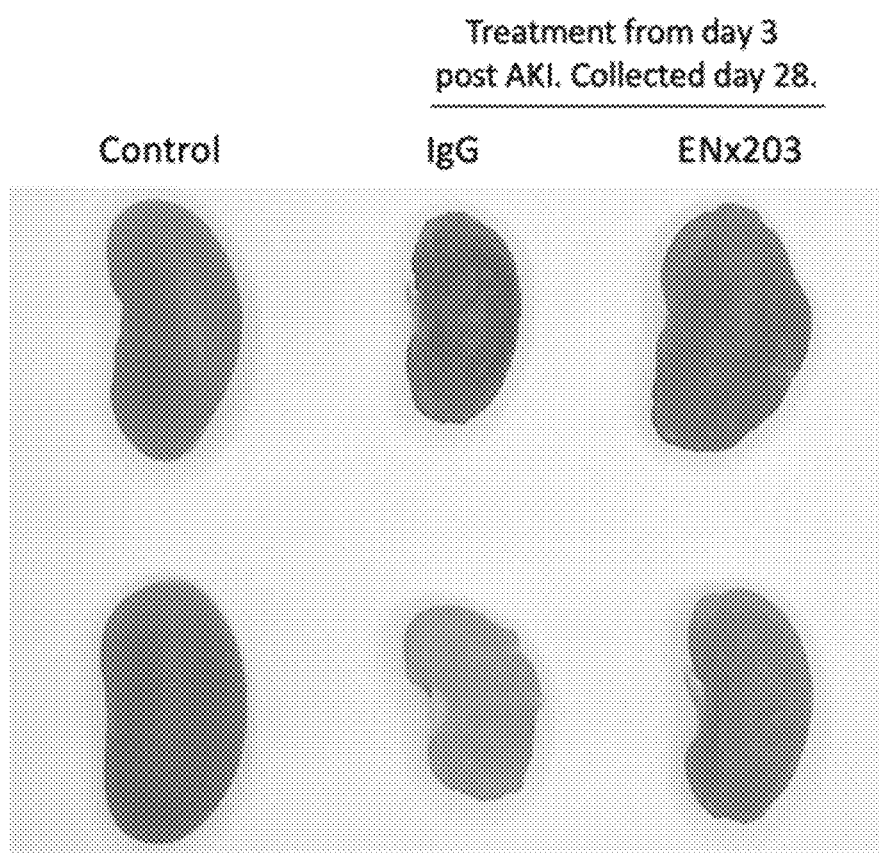

In a further experiment, the inventors investigated the consequences of IL11RA1 knockout in this model of acute, chemically-induced kidney injury. Cre-lox mice that display fibroblast-specific knockout of IL11RA1 in response to tamoxifen were treated with tamoxifen to delete IL-11RA1 from col1A2-positive cells, and subsequently subjected to folate-induced kidney injury as described above (or treatment with vehicle). After 21 days, collagen content was assessed using the HPA assay, and kidney function was determined by analysis of serum urea levels. The results are shown in FIG. 6. The IL11RA1 knockout in fibroblasts was found to protect the mice from folate-induced kidney injury, indicating a central role for IL-11 mediated signalling in fibroblasts in the pathology of renal injury and consequent dysfunction and secondary fibrosis.

In another experiment, mice were treated with folate as described above, and Enx203 was administered from day 3, at 10 mg/kg, biweekly. Body weight, kidney weight, renal collagen content, urine output and gross kidney morphology was evaluated after 28 days. The results are shown in FIG. 7. At the end of the study, mice receiving anti-IL-11 antibody therapy had increased kidney weights, less renal collagen, normal urine outputs and improved gross morphology as compared to mice receiving IgG control.

Figure 8A:
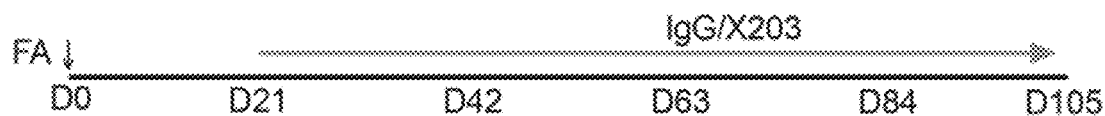
FIGS. 8A to 8F. Schematic, graphs, and image showing that ENx203 treatment reverses kidney injury and dysfunction and induces kidney regeneration. (8A) Schematic representation of the timing of folate administration and antibody treatment. The folate model of kidney injury was established, and animal were not treated the until 21 days after injury. This led to severe reduction of kidney function and increase in collagen content. Antibody treatment was then initiated, and analysis of kidney function by evaluation of serum urea levels and collagen content was performed after 3, 6, 9 and 12 weeks of treatment. This revealed a significant (8B) reduction in collagen content, and (8C) improvement in renal function in ENx203-treated animals compared to animals before the treatment at day 21. While kidneys contained less collagen, they still (8D) gained weight and (8E), (8F) looked less bumpy and had healthier histology (cross-section of kidney, 3 animals). P values are corrected for multiple testing and indicate differences between later time points with the FA 21d groups (Dunnett test). Data is shown as mean±SD.
Figure 11A:
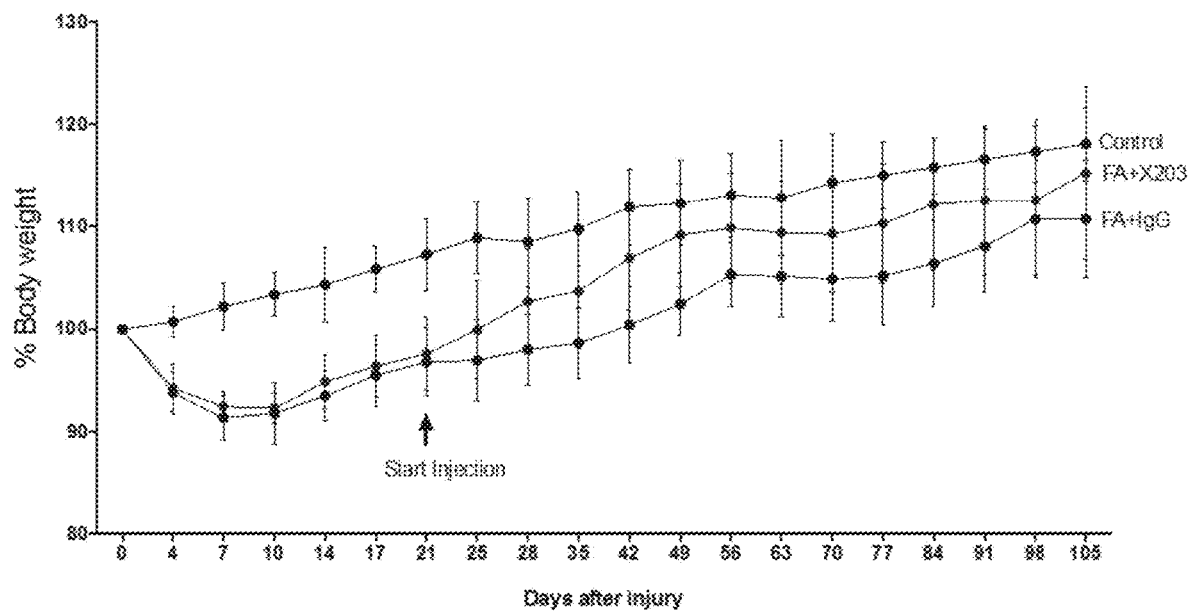
FIGS. 11A and 11B. Graphs showing that ENx203 treatment after established renal injury induces weight gain and leads to a 50% reversal in urinary ACR. The folate model of kidney injury was performed, and animals were not treated until 21 days after injury. Antibody treatment was then initiated, and animal weight was continually assessed. (11A) ENx203-treated animals started to regain weight upon initiation of treatment. (11B) Urinary albumin:creatinine ratio was reversed by ~50% by 12 weeks of therapy as compared to starting levels at 3-weeks post injury.
Figure 11B:
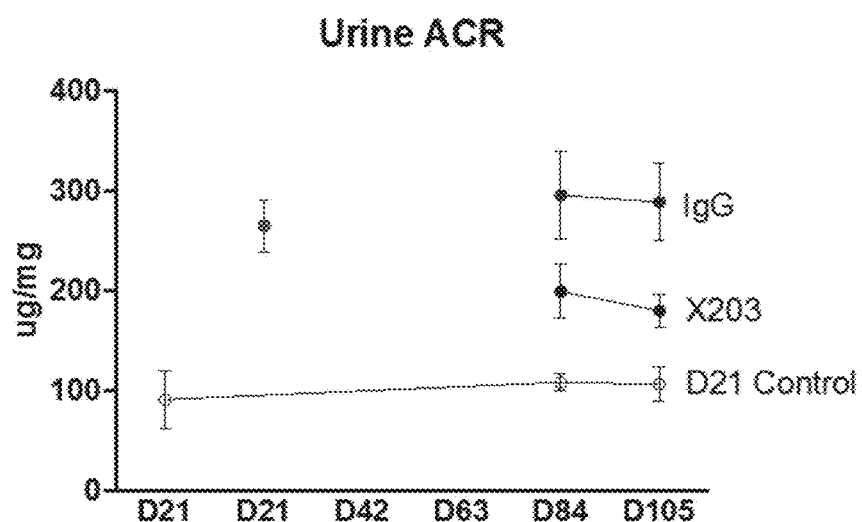

The inventors performed further experiments, in a chemically-induced model of chronic kidney injury. Briefly, renal injury was induced in mice by folate treatment as described above, and were untreated for 21 days. At 21 days post-induction of acute kidney injury by folate treatment, chronic kidney disease had been established, as determined by a ~2.5 fold increase in blood urea nitrogen (FIG. 8B), and a ~2.9 fold increase in the albumin to creatine ratio (ACR) in urine (FIG. 11, lower panel). The kidneys had lost ~33% of their initial mass (FIG. 8C) and collagen levels were elevated ~2.8-fold (FIG. 8A).

Figure 8B:
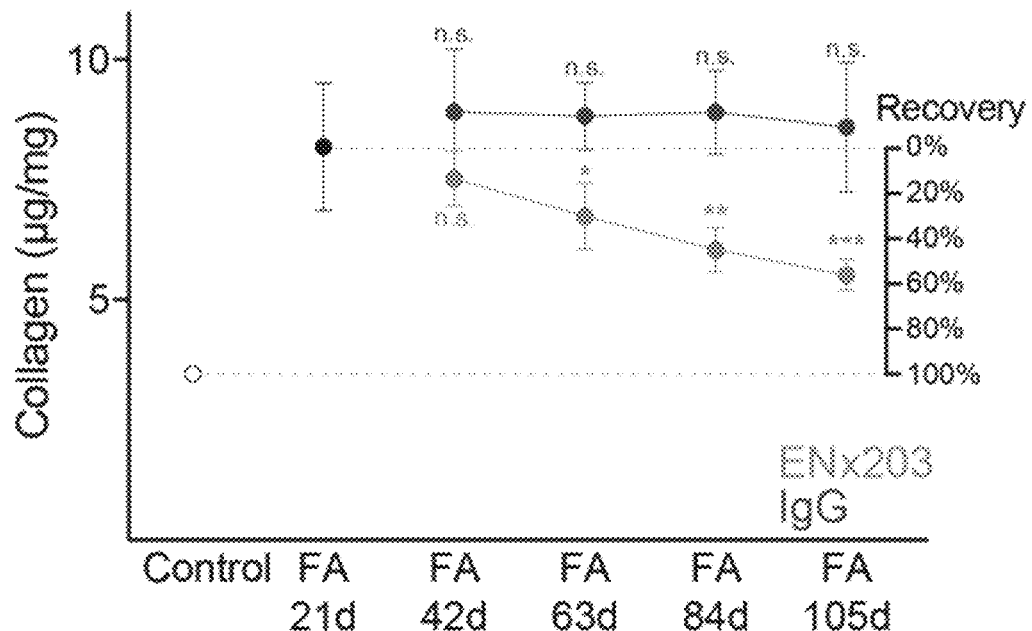
Figure 8C:
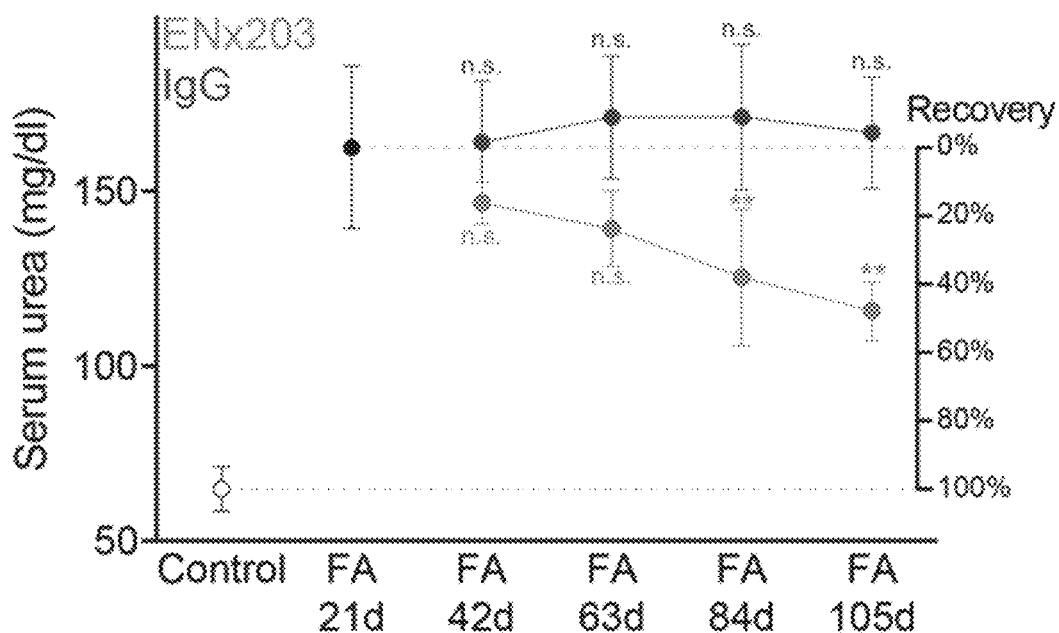

Mice were treated from day 21 with Enx203 or IgG control, at 10 mg/kg, biweekly. Mice were euthanised at the indicated day of the experiment, and renal collagen, serum urea levels, kidney weight and gross kidney morphology were evaluated. The results are shown in FIG. 8. Treatment with Enx203 was associated with reduced levels of renal collagen (FIG. 8A) and reduced levels of serum urea, with an overall 51% reversal in BUN by week 12 of therapy ($P<0.001$ vs IgG; FIG. 8B).

Figure 8D:
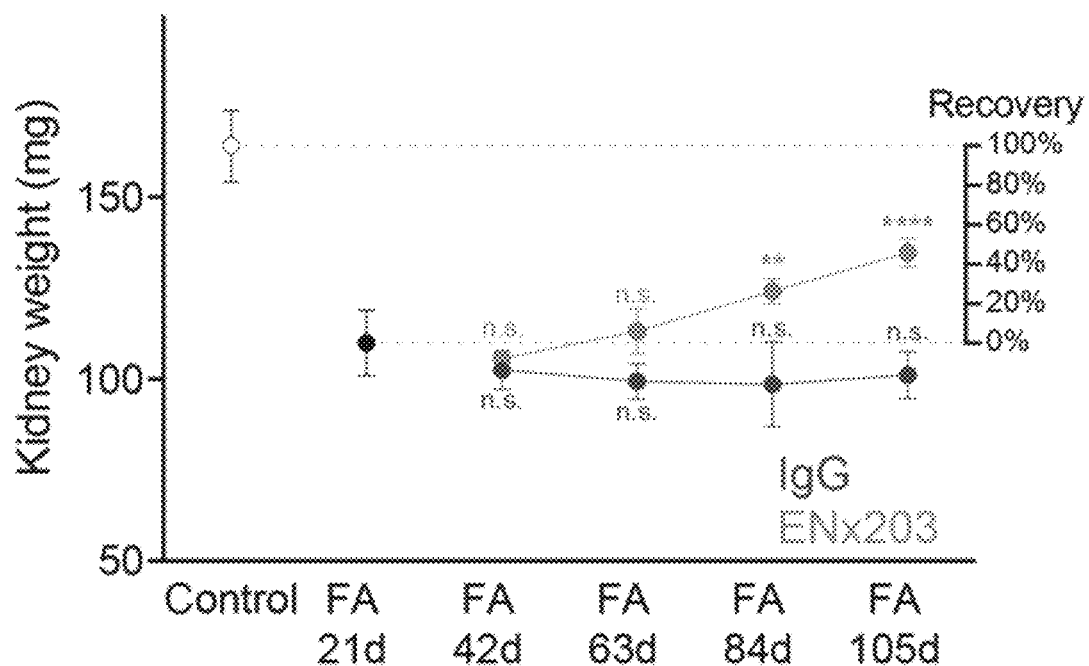
Figure 8E:
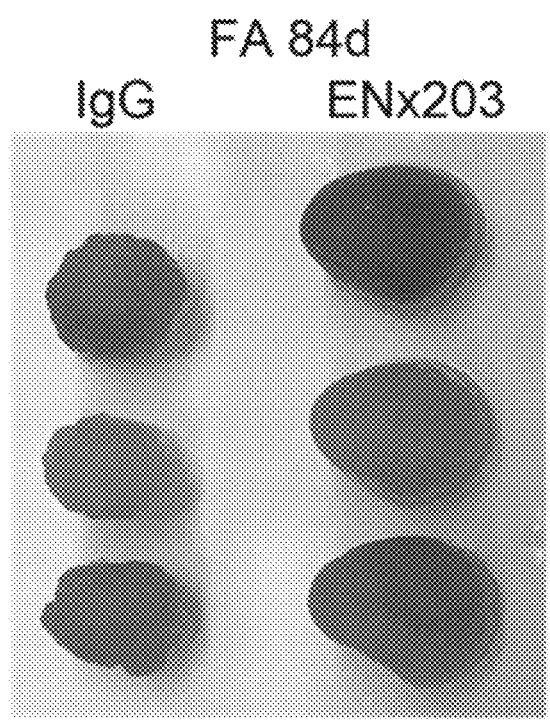
Figure 8F:
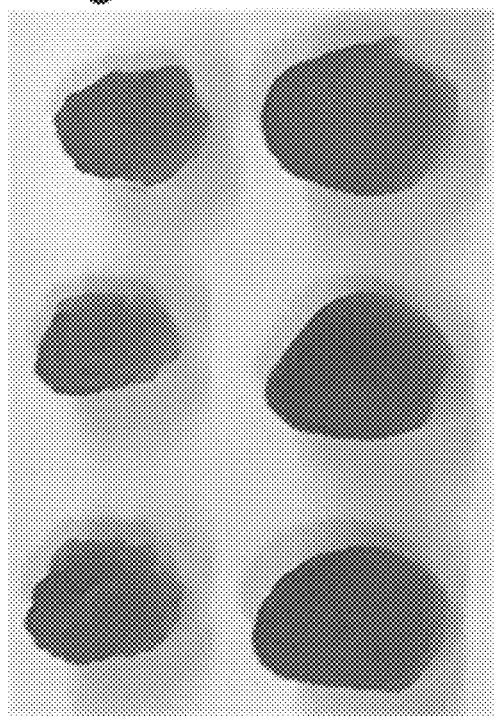

Importantly, kidney weight increased in the Enx203-treated animals over time, whilst renal collagen content decreased (FIGS. 8C and 8A), and serum urea levels decreased over time in Enx203-treated animals (FIG. 8B). These results indicate that more than inhibiting folate-induced renal tissue injury responses, Enx203 treatment promoted regeneration of functional kidney tissue, reversing the injury phenotype. The kidneys of Enx203-treated mice harvested at days 84 and 105 also more closely resembled healthy kidneys (FIG. 8D and FIG. 8E).

Figure 9:
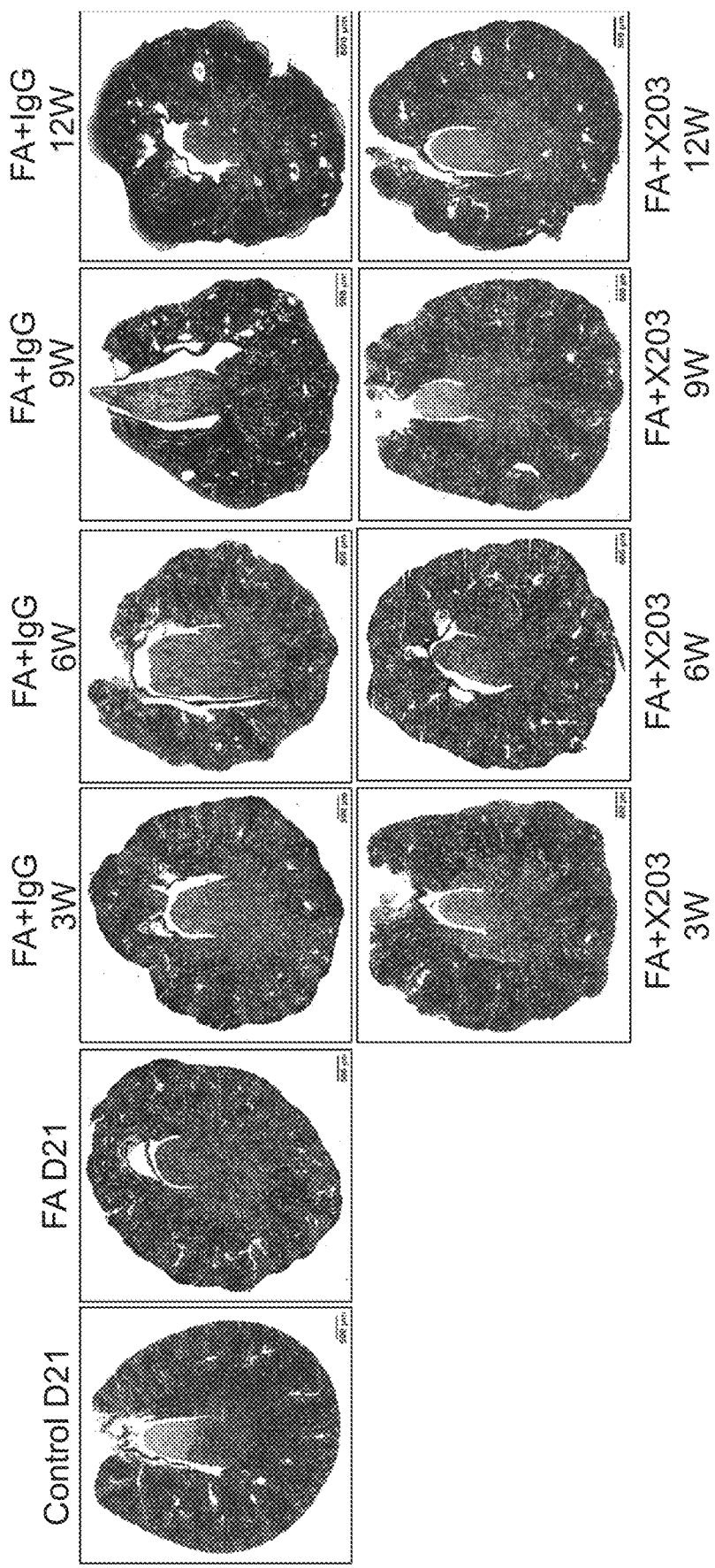
FIG. 9. Images showing that ENx203 treatment reduced collagen content and promoted restoration of normal renal parenchyma and cortical volume. Masson's Trichrome stain of mid-section of kidneys from mice day 21 (D21) after folic acid (FA) injury or control mice and then in mice treated from D21 post FA injury with either IgG or anti-IL-11 for 3, 6, 9 or 12 weeks.
Figure 10:
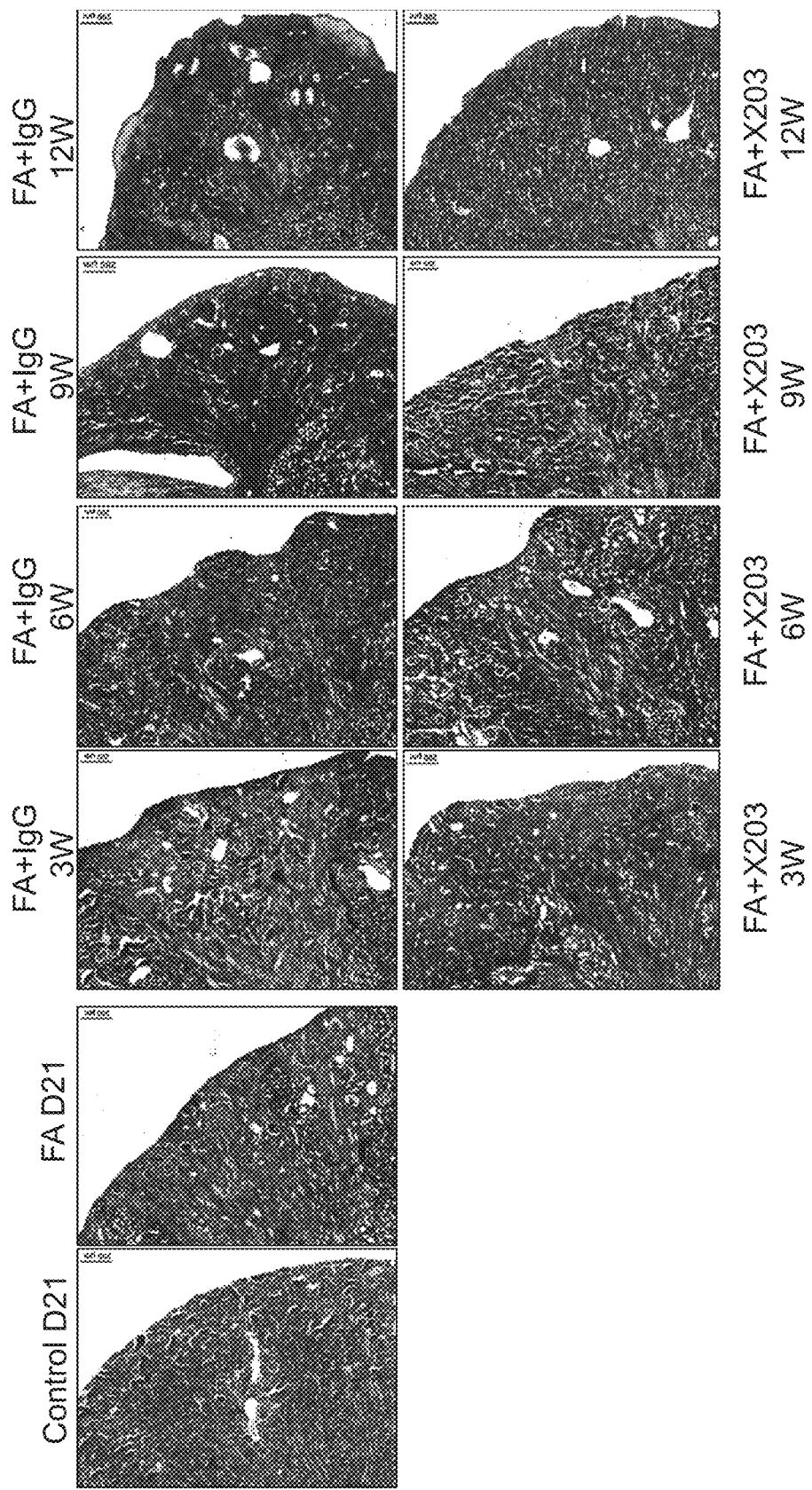
FIG. 10. Images showing higher magnification view of the renal cortex from images shown in FIG. 9. Masson's Trichrome stain of the cortex of kidneys from mice day 21 (D21) after folic acid (FA) injury or control mice and then in mice treated from D21 post FA injury with either IgG or anti-IL-11 for 3, 6, 9 or 12 weeks.

Histological analysis of renal sections from the mice revealed that Enx203 treatment restored normal renal parenchyma (54% reversal in parenchymal loss by week 12 ($P<0.001$), cortical thickness and volume and cortex morphology in the kidneys of mice subjected to folate-induced kidney injury (FIGS. 9 and 10).

The body weights of mice in this experiment were also monitored throughout the course of the experiment, and Enx203 treatment was found to be associated with weight gain of folate treated mice towards control, untreated levels (FIG. 11, upper panel). The ACR in urine was also monitored in mice at days 21, 84 and 105 of the experiment, and the results are shown in FIG. 11 (lower panel). Treatment with Enx203 was found to cause a substantial reduction in urinary ACR (~50% reduction within 12 weeks) in folate-treated mice.

The results demonstrated that antagonism of IL-11-mediated signalling could reverse renal fibrosis and produce extensive regeneration of the kidney parenchyma, which is associated with striking reversal of renal impairment.

Example 3: Investigation of the Molecular Basis of the Inhibition/Reversal of Renal Injury by Antagonists of IL-11 Mediated Signalling The inventors undertook further investigations to evaluate the role of IL-11 mediated signalling in renal tissue function and injury responses.

The transition of tubule epithelial cells to a mesenchymal cell-like phenotype is implicated in damage to the kidney parenchyma and dysfunction associated with renal injury (see e.g. Lovisa et al. Nat. Med. (2015) 21, 998-1009), and so the inventors investigated whether IL-11 mediated signalling has a role in the epithelial-to-mesenchymal transition for TECs.

Human primary tubule epithelial cells (TECs) were stimulated in vitro with TGFB1, IL-11 (5 ng/ml, 24 h) or TGFB1+Enx203 (2 µg/ml, 24 h), and the percentage of ACTA2$^{+ve}$ cells and collagen expression was evaluated using the Operetta high-content imaging platform.

Figure 12A:
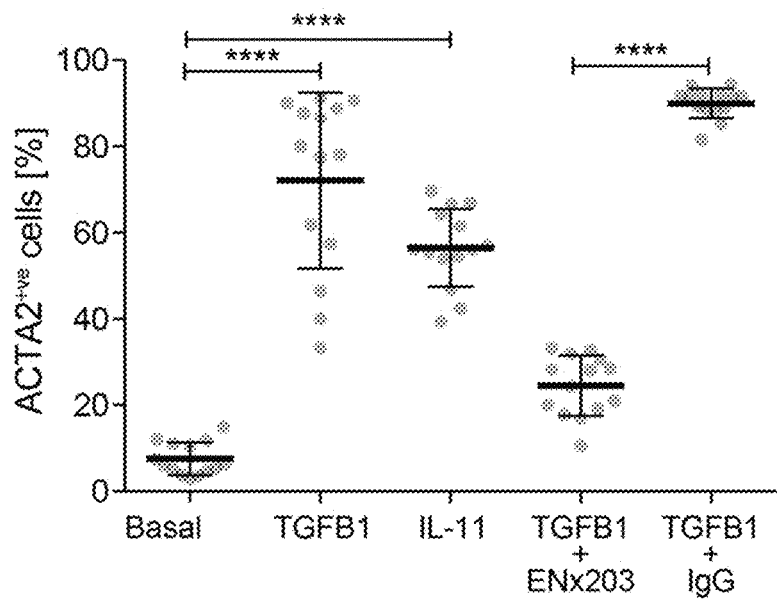
FIGS. 12A and 12B. Graphs showing that TGFB1-driven partial epithelial-mesenchymal transformation of tubular epithelial cells is IL-11 dependent. Human primary tubule epithelial cells were stimulated with TGFB1, IL-11 (5 ng/ml, 24 h) or TGFB1 and antibody (2 µg/ml, 24 h). (12A) The percentage of ACTA2$^{-ve}$ cells and (12B) collagen expression was monitored on the Operetta high-content imaging platform.
Figure 12B:
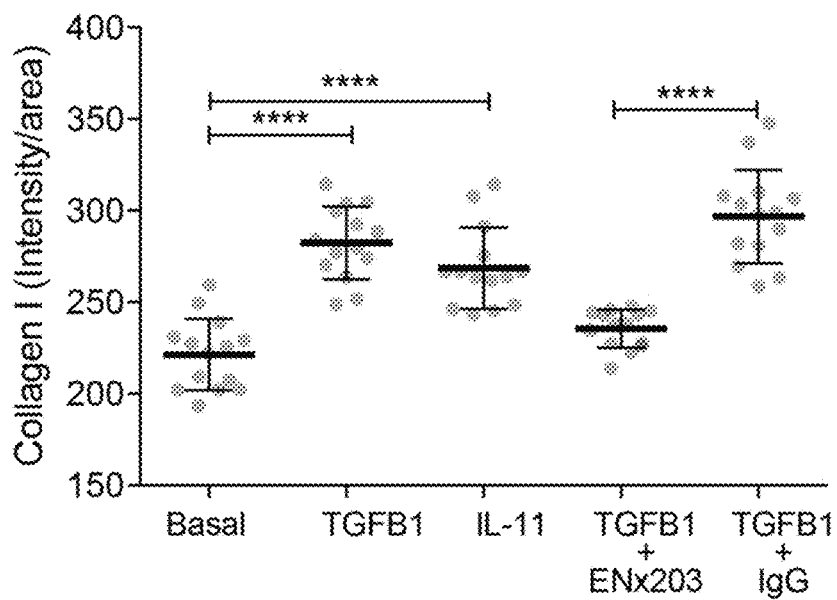

The results are shown in FIG. 12. Both of TGFB1 and IL-11 were found to increase the proportion of ACTA2-expressing TECs, and to increase collagen I expression by these cells. Treatment with Enx203 was found to reduce ACTA2 and collagen I expression by TECs in response to TGFB1/IL-11.

Figure 13:
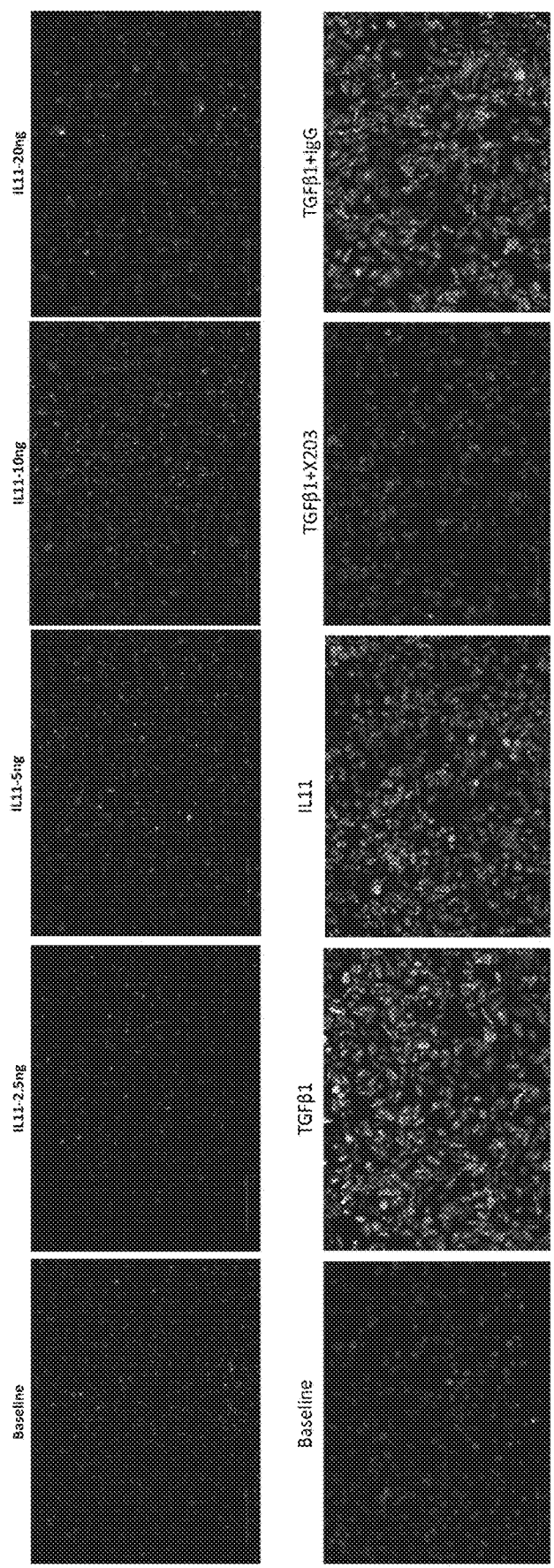
FIG. 13. Images relating to TGFB1-driven partial epithelial-mesenchymal transformation of tubular epithelial cells. Top, human primary tubule epithelial cells were stimulated with IL-11 (2.5-20 ng/ml, 24 h). Operetta high-content imaging was used to visualise actin stress fibre formation using rhodamine-phalloidin. Bottom, visual representation of collagen expression in cells.

In separate experiments, human primary TECs were stimulated in vitro for 24 hours with different concentrations of IL-11 (2.5 ng/ml, 5 ng/ml, 10 ng/ml), TGFB1 (5 ng/ml), or TGFB1 (5 ng/ml)+Enx203 (2 ug/ml), and Operetta high-content imaging was used to visualise actin stress fibre formation using rhodamine-phalloidin (FIG. 13, upper panels) and collagen (FIG. 13, lower panels).

As explained hereinabove, SNAIL has recently been shown to be a critical determinant of TEC dysfunction following acute kidney injury. Its expression in TECs is associated with impaired TEC function and proliferation. Human primary TECs stimulated in vitro for 24 hours with different concentrations of IL-11 (5 ng/ml), TGFB1 (5 ng/ml), TGFB1 (5 ng/ml)+Enx203 (2 ug/ml) or TGFB1 (5 ng/ml)+IgG control (2 ug/ml) were analysed using the Operetta high-content imaging system for expression of ACTA2 or SNAIL.

Figure 14A:
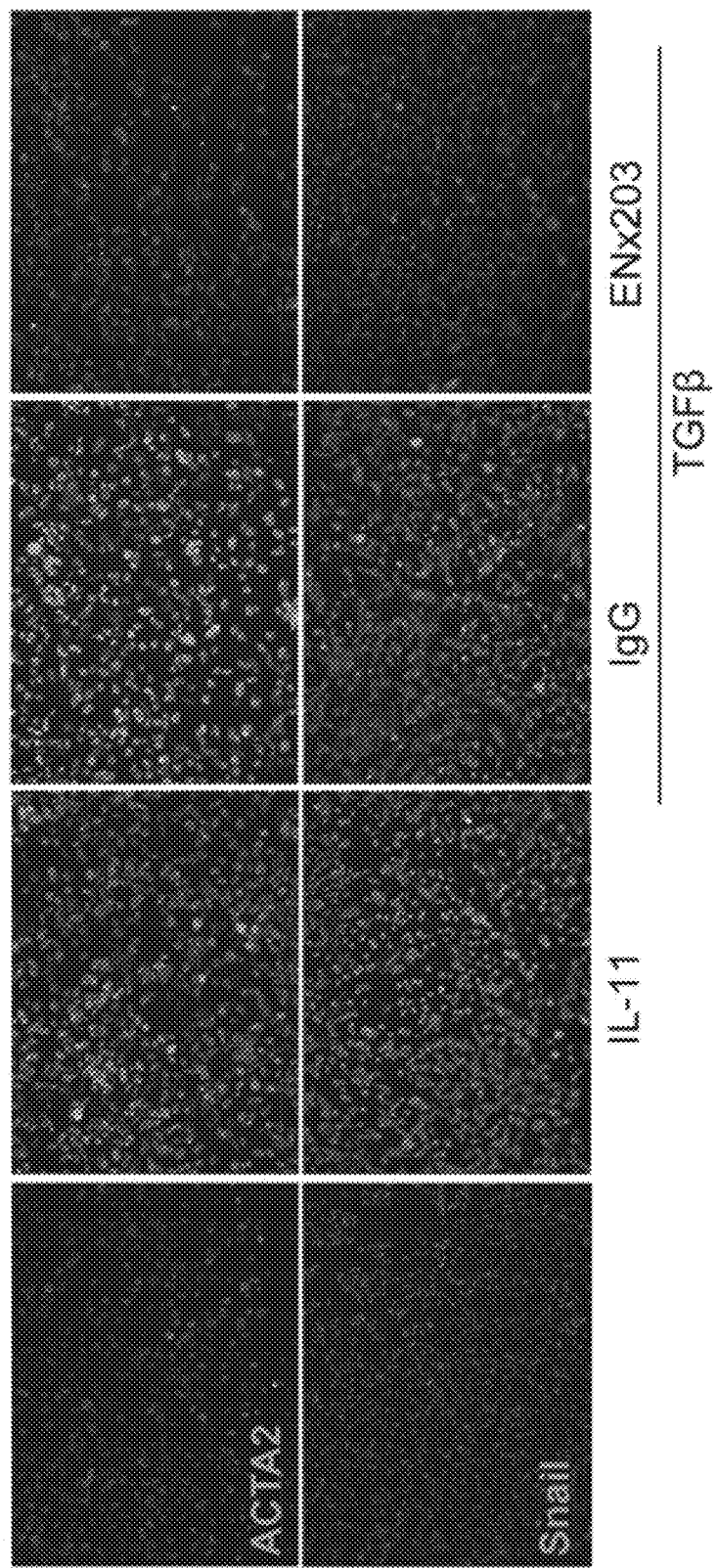
FIGS. 14A and 14B. Images and graph showing that expression of the fundamentally important Snail factor by Tubular epithelial cells (TECs) is IL-11 dependent. Primary human TECs were stimulated with either IL-11 or TGFB in the presence of IgG or anti-IL-11 antibody (ENx203) and expression of the Snail or ACTA2 gene detected using the Operetta imaging platform. (14A) both IL-11 and TGFB induce partial EMT and expression of both ACTA2 and Snail. In the presence of anti-IL-11 antibody this effect was strongly inhibited in TGFB stimulated cells. (14B) quantification of ACTA+ve cells from the micrographs of FIG. 14A.
Figure 14B:
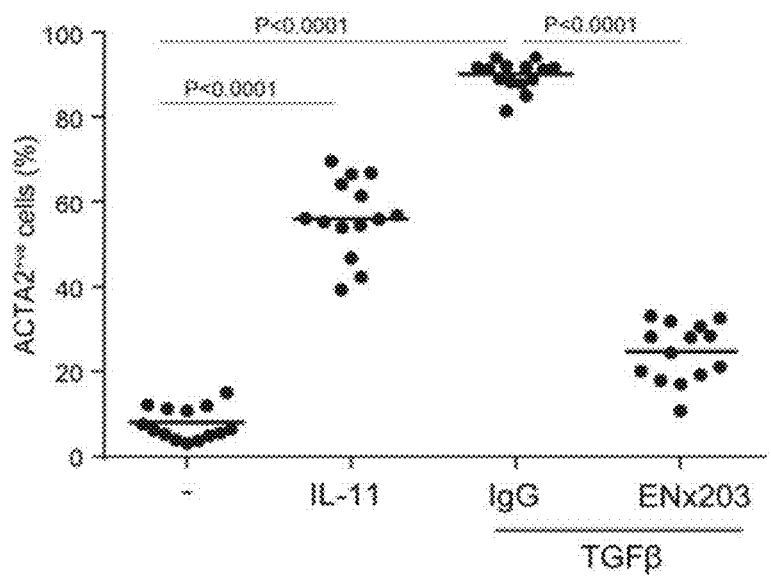

The results are shown in FIG. 14. Treatment with IL-11 or TGFB1 was found to induce partial epithelial cell-mesenchymal cell transition (EMT), and expression of ACTA2 and SNAIL. However, the presence of Enx203 strongly inhibited induction of ACTA2 and SNAIL.

Figure 15:
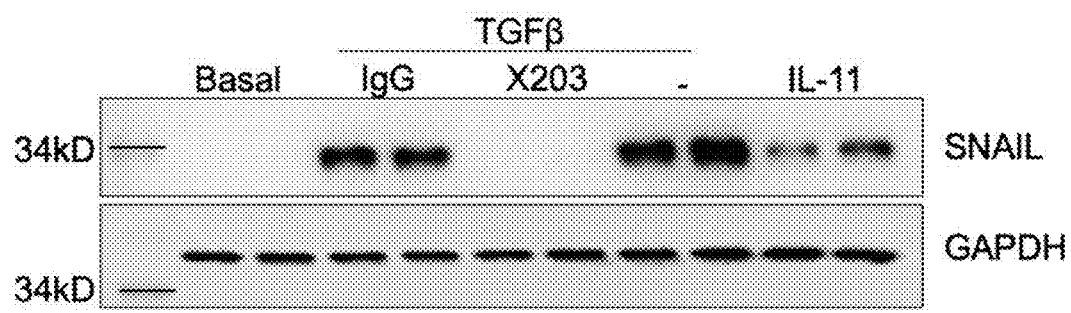
FIG. 15. Image showing that anti-IL-11 antibody treatment prevents Snail induction in primary human TECs. Western blot of primary human kidney tubular epithelial cells treated with TGFB in the presence or absence of anti-IL-11 antibody (ENx203) or with IL-11. Upper panel, induction of SNAIL, the master regulator of EMT, by TGFB (5 ng/ml) is dependent on IL-11 signaling and IL-11 (5 ng/ml) alone is able to induce SNAIL expression. Lower panel, equal protein loading confirmed by GAPDH control protein.

Cell lysates were prepared from the cells, and analysed by western blot for SNAIL expression. A separate western blot for GAPDH was performed as a protein loading control. The results are shown in FIG. 15, and demonstrate that SNAIL expression is upregulated in response to TGFB1 and IL-11, and that TGFB-mediated upregulation of SNAIL was completely prevented by the presence of Enx203.

Thus TGFB1-mediated induction of SNAIL was found to be IL-11-dependent.

The inventors investigated the expression of E-cadherin, the canonical marker of epithelial cell identity, by Western blots of proteins lysates from kidney tissue of mice from the experiment described above in which renal injury was induced in mice by folate treatment as described above, and mice were subsequently treated from day 21 with Enx203 or IgG control, at 10 mg/kg, biweekly.

Figure 16:
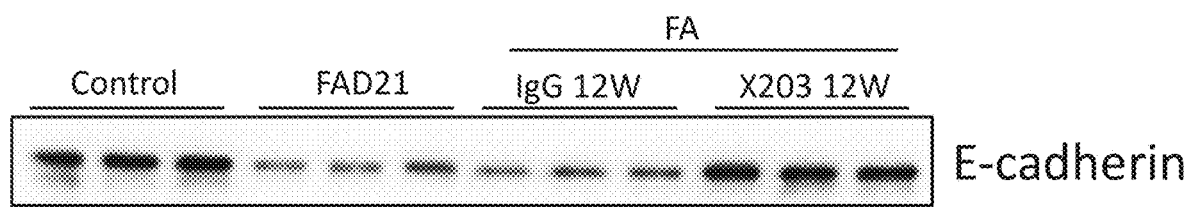
FIG. 16. Image showing that E-cadherin expression in regenerating kidneys is increased with anti-IL-11 therapy. E-cadherin expression is the canonical marker of epithelial cell identity and expression of E-cadherin is lost when cells undergo EMT or partial EMT. In keeping with an effect of IL-11 driving TECs into a partial EMT (pEMT), Western blot of kidneys from mice D21 post folate injury and those treated with IgG for 12 weeks after injury had lower E-cadherin levels compared to controls and this effect was reversed with anti-IL-11 therapy.

The results are shown in FIG. 16. Folate-induced renal injury was found to reduce E-cadherin expression, whilst treatment with Enx203 was found to restore E-cadherin expression.

Example 4: Analysis of the Effect of Inhibition of IL-11 Mediated Signalling in a Model of Physically-Induced Kidney Injury A mouse model of acute renal injury was induced by unilateral ureteric obstruction (UUO). Briefly, mice were treated by sham operation or ureteric obstruction of one ureter.

Mice were treated with ENx203 (referred to as '3C6' in FIG. 17B) or IgG control antibody at day 4, 7 and 9 of treatment (20 mg/kg). The body weights of the mice were monitored throughout the experiment, and collagen content in the kidney was assessed at 10 days post UUO surgery using the HPA assay.

Figure 17A:
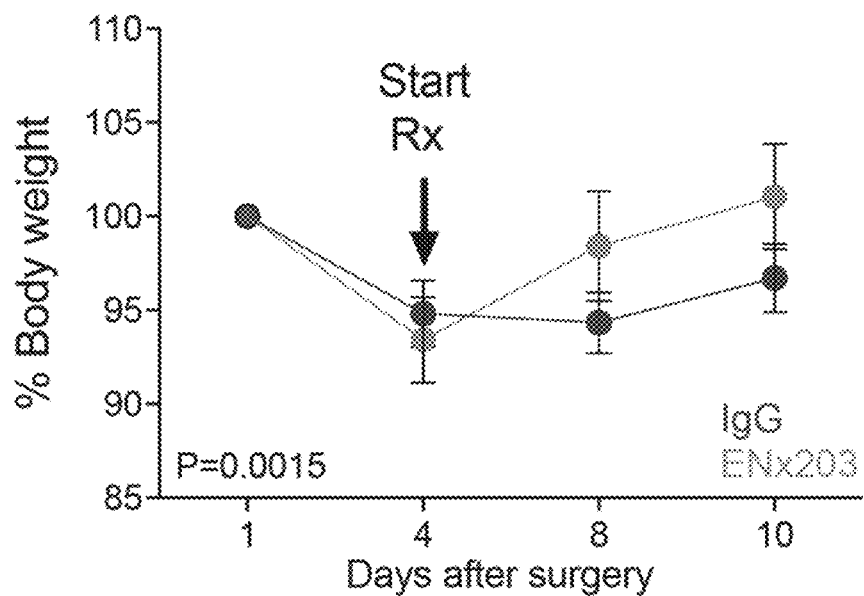
FIGS. 17A and 17B. Graph and bar chart relating to the effect of anti-IL-11 antibody treatment in a Unilateral Ureter Obstruction (UUO) model of kidney injury. UUO was performed to induce physical renal injury responses in mice. Some animals were treated with ENx203 or IgG control antibody at day 4, 7 and 9 of treatment (20 mg/kg). (17A) Body weight of ENx203 and IgG control treated animals. (17B) Collagen content in the kidney was assessed using the HPA assay 10 days after the procedure. Animals treated with ENx203 therapeutic antibody had significantly reduced collagen content compared to animals treated with control antibody. Data is shown as mean±SD. Sidak corrected P-value.
Figure 17B:
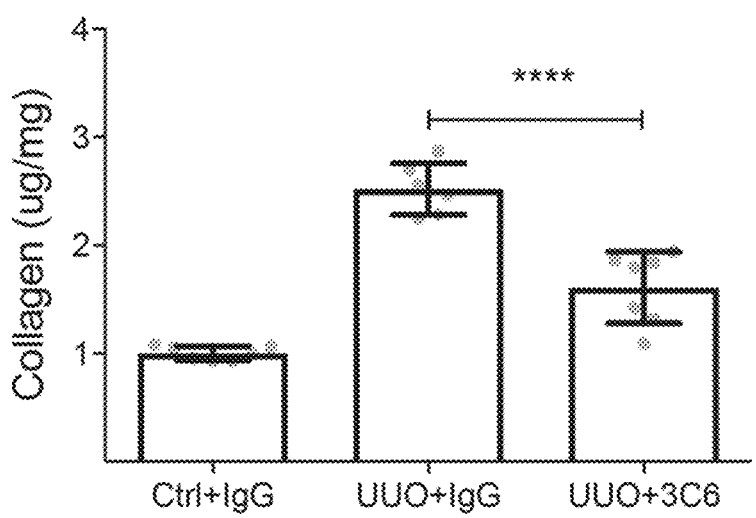

The results are shown in FIG. 17. Mice treated with Enx203 had reduced renal collagen, and increased body-weight as compared to mice subjected to UUO and treated with IgG control antibody.

Example 5: Analysis of the Effect of Inhibition of IL-11 Mediated Signalling in a Model of Cisplatin-Induced Kidney Injury Kidney injury was induced in 10 week old C57Bl/6J mice by administration of 7 mg/kg cisplatin, once weekly for four consecutive weeks. A control group was not administered with cisplatin.

Mice were administered biweekly from week 1 by IP injection with X203 (antibody capable of binding to mouse IL-11 (and human IL-11) and inhibiting IL-11 mediated signalling) or an isotype-matched IgG control antibody at a dose of 10 mg/kg, or with saline (control). Mice were harvested for analysis after 8 weeks.

Figure 18A:
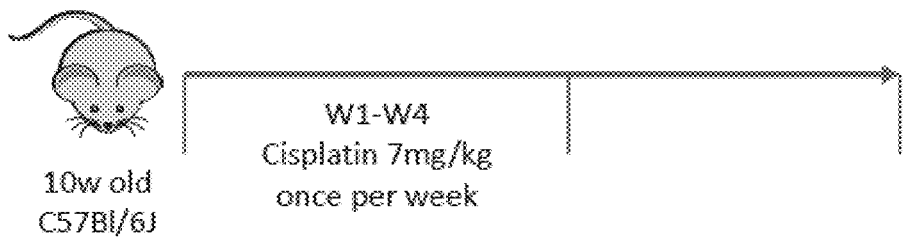
FIGS. 18A to 18H. Schematic and graphs relating to the effect of anti-IL-11 antibody treatment in a cisplatin-induced model of kidney injury. (18A) Mice were administered cisplatin (7 mg/kg cisplatin), once weekly for 4 weeks. A control group was administered with saline. Mice were administered biweekly from week 1 by IP injection with 10 mg/kg X203 or an isotype-matched IgG control antibody. Mice were harvested for analysis of the kidneys after 8 weeks. (18B) Collagen content in the kidney as assessed by the HPA assay. (18C to 18H) RNA expression of (18C) Col3, (18D) Fibronectin, (18E) MMP2, (18F) TIMP, (18G) CCL5 and (18H) CCL2 as determined by qPCR. Graphs show fold change (FC) in expression relative to expression in saline-treated mice.
Figure 18B:
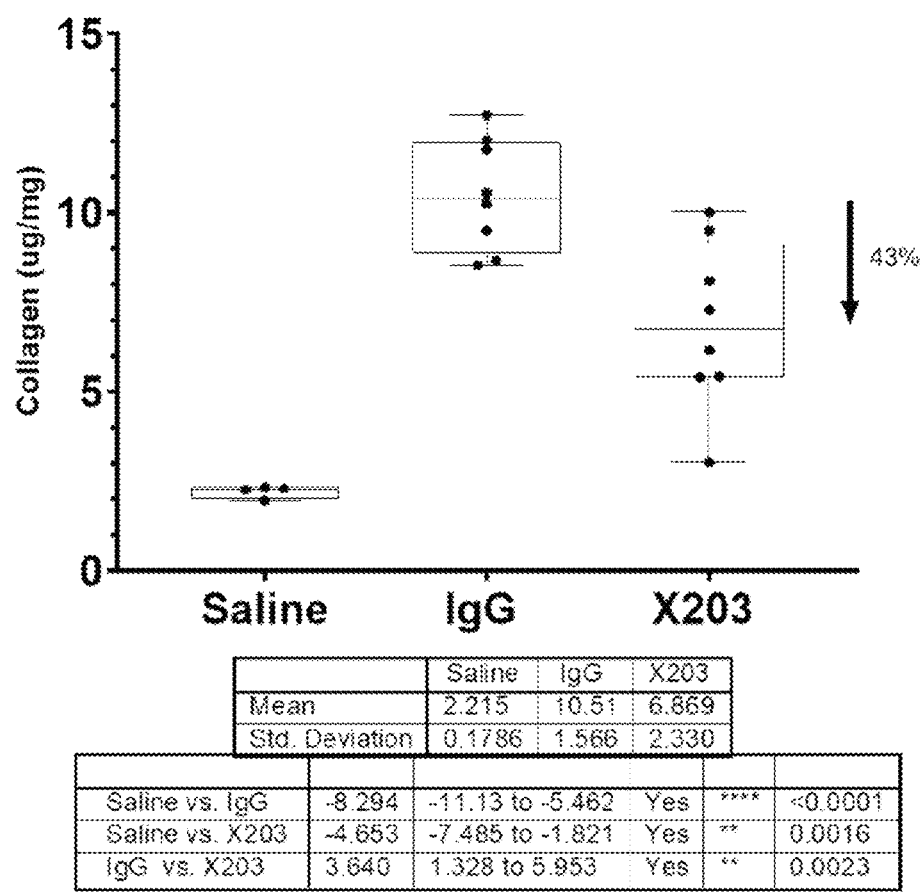
Figure 18C:
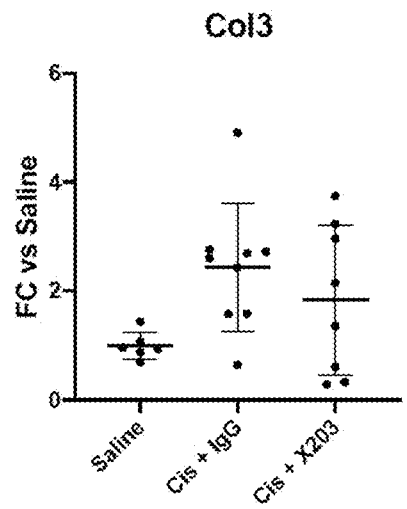
Figure 18D:
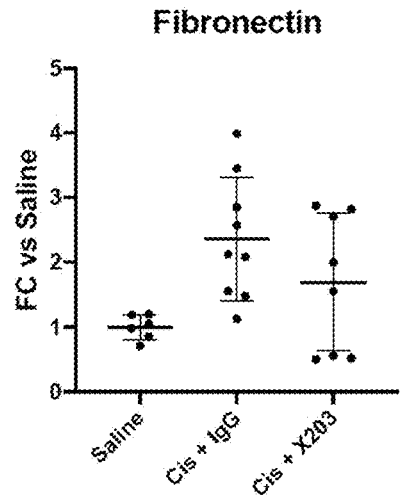
Figure 18E:
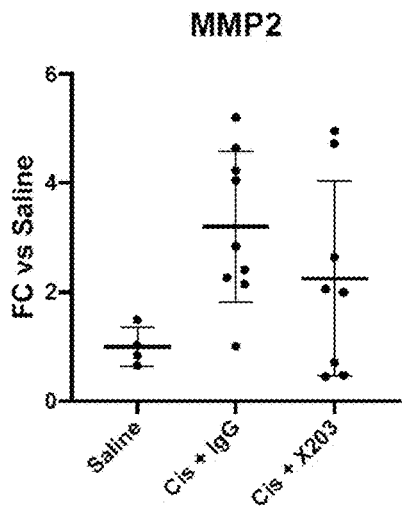
Figure 18F:
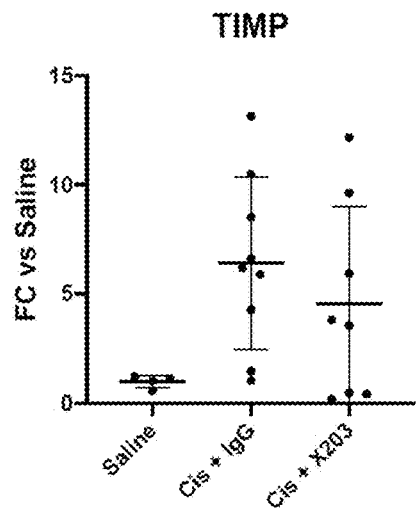
Figure 18G:
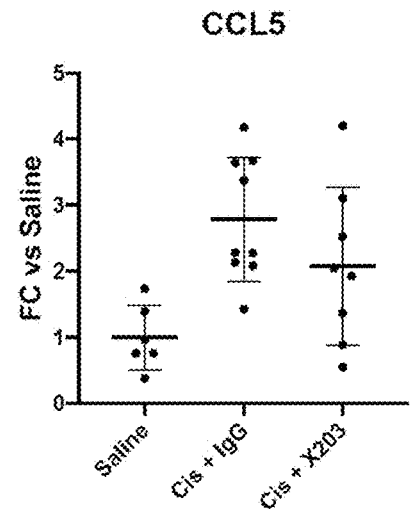
Figure 18H:
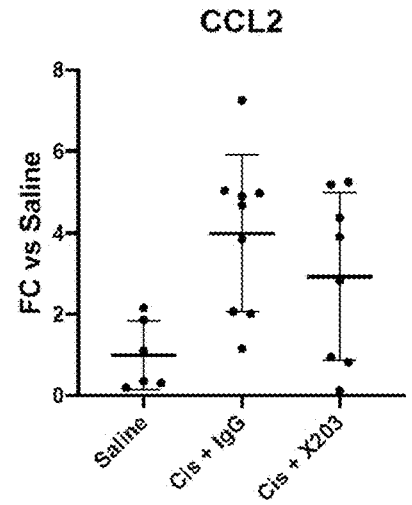

The amount of total collagen in the kidney was quantified on the basis of colourimetric detection of hydroxyproline using a Quickzyme Total Collagen assay kit (Quickzyme Biosciences). The results are shown in FIG. 18B. Cisplatin treatment was associated with increased collagen content of the kidney. Kidneys from cisplatin-treated mice administered neutralising anti-IL-11 antibody had lower collagen content than kidneys from cisplatin-treated mice administered with IgG control antibody. The kidneys of mice subjected to different treatments were also analysed for RNA expression of Col3, Fibronectin, MMP2, TIMP, CCL5 and CCL2 by qPCR.

Briefly, total RNA was extracted from snap-frozen kidney tissue using Trizol (Invitrogen) and RNeasy Mini Kit (Qiagen). PCR amplifications were performed using iScript cDNA Synthesis Kit (Biorad). Gene expression was analyzed in duplicate by TaqMan (Applied Biosystems) or SYBR green (Qiagen) technology using StepOnePlus (Applied Biosystem) over 40 cycles. Expression data were normalized to GAPDH mRNA expression and fold change was calculated relative to expression in saline-treated control subjects.

The results are shown in FIGS. 18C to 18H. Cisplatin treatment was associated with increased expression of Col3, Fibronectin, MMP2, TIMP, CCL5 and CCL2. Kidneys from cisplatin-treated mice administered neutralising anti-IL-11 antibody tended to have lower expression of Col3, Fibronectin, MMP2, TIMP, CCL5 and CCL2 as compared to kidneys from cisplatin-treated mice administered with IgG control antibody.

The invention claimed is:

1. A method of inhibiting the transition of tubular epithelial cells (TECs) to a mesenchymal cell-like phenotype in a subject, comprising administering to a subject in need thereof an effective amount of: an anti-interleukin 11 (IL-11) antibody or an antigen-binding fragment thereof which is an antagonist of IL-11-mediated signaling, thereby inhibiting the transition of TECs to a mesenchymal cell-like phenotype in the subject, wherein the subject in need thereof has proximal and/or distal TEC damage.

2. The method of claim 1, wherein the subject is a subject suffering from impairment to renal function.

3. The method of claim 1, wherein the anti-IL-11 antibody or antigen-binding fragment thereof comprises:

(i) a heavy chain variable (VH) region incorporating the following CDRs:

HC-CDR1 having the amino acid sequence of SEQ ID NO:40

HC-CDR2 having the amino acid sequence of SEQ ID NO:41

HC-CDR3 having the amino acid sequence of SEQ ID NO:42, ; and (ii) a light chain variable (VL) region incorporating the following CDRs:

LC-CDR1 having the amino acid sequence of SEQ ID NO:43

LC-CDR2 having the amino acid sequence of SEQ ID NO:44

LC-CDR3 having the amino acid sequence of SEQ ID NO:45.

4. The method of claim 1, wherein the anti-IL-11 antibody or antigen-binding fragment thereof comprises:

(i) a heavy chain variable (VH) region incorporating the following CDRs:
    HC-CDR1 having the amino acid sequence of SEQ ID NO:34
    HC-CDR2 having the amino acid sequence of SEQ ID NO:35
    HC-CDR3 having the amino acid sequence of SEQ ID NO:36; and
(ii) a light chain variable (VL) region incorporating the following CDRs:
    LC-CDR1 having the amino acid sequence of SEQ ID NO:37
    LC-CDR2 having the amino acid sequence of SEQ ID NO:38
    LC-CDR3 having the amino acid sequence of SEQ ID NO:39.

5. The method of claim 1, wherein the subject is a subject in which expression of interleukin 11 (IL-11) is upregulated.

* * * * *

SEQUENCE LISTING

```
<160> NUMBER OF SEQ ID NOS: 59

<210> SEQ ID NO 1
<211> LENGTH: 199
<212> TYPE: PRT
<213> ORGANISM: Homo sapiens

<400> SEQUENCE: 1

Met Asn Cys Val Cys Arg Leu Val Leu Val Val Leu Ser Leu Trp Pro
1               5                   10                  15

Asp Thr Ala Val Ala Pro Gly Pro Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110
```

Arg Ala Gly Gly Ser Ser Leu Lys Thr Leu Glu Pro Glu Leu Gly Thr
            115                 120                 125

Leu Gln Ala Arg Leu Asp Arg Leu Leu Arg Leu Gln Leu Leu Met
130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
            195

<210> SEQ ID NO 2
<211> LENGTH: 918
<212> TYPE: PRT
<213> ORGANISM: Homo sapiens

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

-continued

```
Leu Lys Pro Phe Thr Glu Tyr Val Phe Arg Ile Arg Cys Met Lys Glu
    290                 295                 300
Asp Gly Lys Gly Tyr Trp Ser Asp Trp Ser Glu Ala Ser Gly Ile
305                 310                 315                 320
Thr Tyr Glu Asp Arg Pro Ser Lys Ala Pro Ser Phe Trp Tyr Lys Ile
                    325                 330                 335
Asp Pro Ser His Thr Gln Gly Tyr Arg Thr Val Gln Leu Val Trp Lys
                340                 345                 350
Thr Leu Pro Pro Phe Glu Ala Asn Gly Lys Ile Leu Asp Tyr Glu Val
            355                 360                 365
Thr Leu Thr Arg Trp Lys Ser His Leu Gln Asn Tyr Thr Val Asn Ala
    370                 375                 380
Thr Lys Leu Thr Val Asn Leu Thr Asn Asp Arg Tyr Leu Ala Thr Leu
385                 390                 395                 400
Thr Val Arg Asn Leu Val Gly Lys Ser Asp Ala Ala Val Leu Thr Ile
                    405                 410                 415
Pro Ala Cys Asp Phe Gln Ala Thr His Pro Val Met Asp Leu Lys Ala
                420                 425                 430
Phe Pro Lys Asp Asn Met Leu Trp Val Glu Trp Thr Thr Pro Arg Glu
            435                 440                 445
Ser Val Lys Lys Tyr Ile Leu Glu Trp Cys Val Leu Ser Asp Lys Ala
    450                 455                 460
Pro Cys Ile Thr Asp Trp Gln Gln Glu Asp Gly Thr Val His Arg Thr
465                 470                 475                 480
Tyr Leu Arg Gly Asn Leu Ala Glu Ser Lys Cys Tyr Leu Ile Thr Val
                    485                 490                 495
Thr Pro Val Tyr Ala Asp Gly Pro Gly Ser Pro Glu Ser Ile Lys Ala
                500                 505                 510
Tyr Leu Lys Gln Ala Pro Pro Ser Lys Gly Pro Thr Val Arg Thr Lys
            515                 520                 525
Lys Val Gly Lys Asn Glu Ala Val Leu Glu Trp Asp Gln Leu Pro Val
    530                 535                 540
Asp Val Gln Asn Gly Phe Ile Arg Asn Tyr Thr Ile Phe Tyr Arg Thr
545                 550                 555                 560
Ile Ile Gly Asn Glu Thr Ala Val Asn Val Asp Ser Ser His Thr Glu
                    565                 570                 575
Tyr Thr Leu Ser Ser Leu Thr Ser Asp Thr Leu Tyr Met Val Arg Met
                580                 585                 590
Ala Ala Tyr Thr Asp Glu Gly Gly Lys Asp Gly Pro Glu Phe Thr Phe
            595                 600                 605
Thr Thr Pro Lys Phe Ala Gln Gly Glu Ile Glu Ala Ile Val Val Pro
    610                 615                 620
Val Cys Leu Ala Phe Leu Leu Thr Thr Leu Leu Gly Val Leu Phe Cys
625                 630                 635                 640
Phe Asn Lys Arg Asp Leu Ile Lys Lys His Ile Trp Pro Asn Val Pro
                    645                 650                 655
Asp Pro Ser Lys Ser His Ile Ala Gln Trp Ser Pro His Thr Pro Pro
                660                 665                 670
Arg His Asn Phe Asn Ser Lys Asp Gln Met Tyr Ser Asp Gly Asn Phe
            675                 680                 685
Thr Asp Val Ser Val Val Glu Ile Glu Ala Asn Asp Lys Lys Pro Phe
    690                 695                 700
```

```
Pro Glu Asp Leu Lys Ser Leu Asp Leu Phe Lys Glu Lys Ile Asn
705                 710                 715                 720

Thr Glu Gly His Ser Ser Gly Ile Gly Gly Ser Ser Cys Met Ser Ser
            725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Val Asn Glu Glu Asp Phe Val Arg Leu
        835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
                900                 905                 910

Gly Gly Tyr Met Pro Gln
        915

<210> SEQ ID NO 3
<211> LENGTH: 422
<212> TYPE: PRT
<213> ORGANISM: Homo sapiens

<400> SEQUENCE: 3

Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160
```

-continued

```
Arg Ser Pro Ser Thr Gly Pro Trp Pro Cys Pro Gln Asp Pro Leu Gly
            165                 170                 175

Ala Ala Arg Cys Val Val His Gly Ala Glu Phe Trp Ser Gln Tyr Arg
        180                 185                 190

Ile Asn Val Thr Glu Val Asn Pro Leu Gly Ala Ser Thr Arg Leu Leu
            195                 200                 205

Asp Val Ser Leu Gln Ser Ile Leu Arg Pro Asp Pro Gln Gly Leu
        210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
                260                 265                 270

Pro Ala Gly Leu Glu Glu Val Ile Thr Asp Ala Val Ala Gly Leu Pro
            275                 280                 285

His Ala Val Arg Val Ser Ala Arg Asp Phe Leu Asp Ala Gly Thr Trp
        290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                325                 330                 335

Glu Pro Gln Val Asp Ser Pro Ala Pro Pro Arg Pro Ser Leu Gln Pro
            340                 345                 350

His Pro Arg Leu Leu Asp His Arg Asp Ser Val Glu Gln Val Ala Val
        355                 360                 365

Leu Ala Ser Leu Gly Ile Leu Ser Phe Leu Gly Leu Val Ala Gly Ala
370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
                405                 410                 415

Pro Gly Ala Pro Asn Leu
            420

<210> SEQ ID NO 4
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 4
ccttccaaag ccagatctt                                              19

<210> SEQ ID NO 5
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 5
gcctgggcag gaacatata                                              19

<210> SEQ ID NO 6
<211> LENGTH: 19
```

-continued

```
<212> TYPE: DNA
<213> ORGANISM: Artificial Sequence
<220> FEATURE:
<223> OTHER INFORMATION: siRNA target IL-11

<400> SEQUENCE: 6
cctgggcagg aacatatat                                                 19

<210> SEQ ID NO 7
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 7
ggttcattat ggctgtgtt                                                 19

<210> SEQ ID NO 8
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 8
ggaccatacc aaaggagat                                                 19

<210> SEQ ID NO 9
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 9
gcgtctttgg gaatcctttt                                                19

<210> SEQ ID NO 10
<211> LENGTH: 18
<212> TYPE: DNA
<213> ORGANISM: Artificial Sequence
<220> FEATURE:
<223> OTHER INFORMATION: siRNA target IL-11Ralpha

<400> SEQUENCE: 10
gcaggacagt agatccct                                                  18

<210> SEQ ID NO 11
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 11
gctcaaggaa cgtgtgtaa                                                 19

<210> SEQ ID NO 12
<211> LENGTH: 42
<212> TYPE: DNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
```

```
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 12
ccuuccaaag ccagaucuun naagaucugg cuuuggaagg nn                42

<210> SEQ ID NO 13
<211> LENGTH: 42
<212> TYPE: DNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 13
gccugggcag gaacauauan nuauauguuc cugcccaggc nn                42

<210> SEQ ID NO 14
<211> LENGTH: 42
<212> TYPE: DNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 14
ccugggcagg aacauauaun nauauauguu ccugcccagg nn                42

<210> SEQ ID NO 15
<211> LENGTH: 42
<212> TYPE: DNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 15
gguucauuau ggcuguguun naacacagcc auaaugaacc nn                42

<210> SEQ ID NO 16
<211> LENGTH: 42
<212> TYPE: DNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
```

<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 16
ggaccauacc aaaggagaun naucuccuuu gguauggucc nn                          42

<210> SEQ ID NO 17
<211> LENGTH: 42
<212> TYPE: DNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 17
gcgucuuugg gaauccuuun naaaggauuc ccaaagacgc nn                          42

<210> SEQ ID NO 18
<211> LENGTH: 42
<212> TYPE: DNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 18
gcaggacagu agaucccuan nuagggaucu acuguccugc nn                          42

<210> SEQ ID NO 19
<211> LENGTH: 42
<212> TYPE: DNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 19
gcucaaggaa cguguguaan nuuacacacg uuccuugagc nn                          42

<210> SEQ ID NO 20
<211> LENGTH: 21
<212> TYPE: PRT
<213> ORGANISM: Artificial Sequence
<220> FEATURE:
<223> OTHER INFORMATION: 20 amino acid linker

<400> SEQUENCE: 20

```
Gly Pro Ala Gly Gln Ser Gly Gly Gly Gly Ser Gly Gly Gly Ser
1               5                   10                  15

Gly Gly Gly Ser Val
            20
```

<210> SEQ ID NO 21
<211> LENGTH: 516
<212> TYPE: PRT
<213> ORGANISM: Artificial Sequence
<220> FEATURE:
<223> OTHER INFORMATION: Hyper IL-11 (IL-11RA:IL-11 fusion)

<400> SEQUENCE: 21

```
Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
                20                  25                  30

Pro Gly Val Gln Tyr Gly Gln Pro Gly Arg Ser Val Lys Leu Cys Cys
            35                  40                  45

Pro Gly Val Thr Ala Gly Asp Pro Val Ser Trp Phe Arg Asp Gly Glu
        50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Thr Val Thr Leu Gln Leu Gly Tyr Pro Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
130                 135                 140

Leu Thr Ser Tyr Arg Lys Lys Thr Val Leu Gly Ala Asp Ser Gln Arg
                145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Pro Gln Gly Leu
    210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
            260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
    290                 295                 300

Ser Thr Trp Ser Pro Glu Ala Trp Gly Thr Pro Ser Thr Gly Pro Ala
305                 310                 315                 320

Gly Gln Ser Gly Gly Gly Gly Ser Gly Gly Gly Ser Gly Gly Gly
```

```
                    325                 330                 335
Ser Val Pro Gly Pro Pro Gly Pro Pro Arg Val Ser Pro Asp Pro
            340                 345                 350
Arg Ala Glu Leu Asp Ser Thr Val Leu Leu Thr Arg Ser Leu Leu Ala
            355                 360                 365
Asp Thr Arg Gln Leu Ala Ala Gln Leu Arg Asp Lys Phe Pro Ala Asp
    370                 375                 380
Gly Asp His Asn Leu Asp Ser Leu Pro Thr Leu Ala Met Ser Ala Gly
385                 390                 395                 400
Ala Leu Gly Ala Leu Gln Leu Pro Gly Val Leu Thr Arg Leu Arg Ala
                405                 410                 415
Asp Leu Leu Ser Tyr Leu Arg His Val Gln Trp Leu Arg Arg Ala Gly
                420                 425                 430
Gly Ser Ser Leu Lys Thr Leu Glu Pro Glu Leu Gly Thr Leu Gln Ala
                435                 440                 445
Arg Leu Asp Arg Leu Leu Arg Arg Leu Gln Leu Met Ser Arg Leu
    450                 455                 460
Ala Leu Pro Gln Pro Pro Asp Pro Ala Pro Pro Leu Ala Pro
465                 470                 475                 480
Pro Ser Ser Ala Trp Gly Gly Ile Arg Ala Ala His Ala Ile Leu Gly
                485                 490                 495
Gly Leu His Leu Thr Leu Asp Trp Ala Val Arg Gly Leu Leu Leu Leu
                500                 505                 510
Lys Thr Arg Leu
        515

<210> SEQ ID NO 22
<211> LENGTH: 119
<212> TYPE: PRT
<213> ORGANISM: Artificial Sequence
<220> FEATURE:
<223> OTHER INFORMATION: Enx203 VH

<400> SEQUENCE: 22

Glu Val Gln Leu Gln Gln Ser Gly Pro Glu Leu Val Lys Pro Gly Ala
1               5                   10                  15
Ser Val Lys Ile Pro Cys Lys Ala Ser Gly Tyr Thr Phe Thr Asp Tyr
                20                  25                  30
Asn Met Asp Trp Val Lys Gln Ser His Gly Lys Ser Leu Glu Trp Ile
            35                  40                  45
Gly Asp Ile Asn Pro His Asn Gly Gly Pro Ile Tyr Asn Gln Lys Phe
    50                  55                  60
Thr Gly Lys Ala Thr Leu Thr Val Asp Lys Ser Ser Ser Thr Ala Tyr
65                  70                  75                  80
Met Glu Leu Arg Ser Leu Thr Ser Glu Asp Thr Ala Val Tyr Tyr Cys
                85                  90                  95
Ala Arg Gly Glu Leu Gly His Trp Tyr Phe Asp Val Trp Gly Thr Gly
                100                 105                 110
Thr Thr Val Thr Val Ser Ser
        115

<210> SEQ ID NO 23
<211> LENGTH: 111
<212> TYPE: PRT
<213> ORGANISM: Artificial Sequence
<220> FEATURE:
<223> OTHER INFORMATION: Enx203 VL
```

<400> SEQUENCE: 23

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Asp Leu Pro Pro Thr Phe Gly Gly Gly Thr Lys Leu Glu Ile Lys
            100                 105                 110

<210> SEQ ID NO 24
<211> LENGTH: 117
<212> TYPE: PRT
<213> ORGANISM: Artificial Sequence
<220> FEATURE:
<223> OTHER INFORMATION: Enx209 VH

<400> SEQUENCE: 24

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Asn Tyr
            20                  25                  30

Trp Met His Trp Leu Lys Gln Arg Pro Val Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ala
        115

<210> SEQ ID NO 25
<211> LENGTH: 107
<212> TYPE: PRT
<213> ORGANISM: Artificial Sequence
<220> FEATURE:
<223> OTHER INFORMATION: Enx209 VL

<400> SEQUENCE: 25

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Ser His Glu Ala Pro Arg Leu Leu Ile
        35                  40                  45

Lys Tyr Ala Ser Gln Ser Ile Ser Gly Ile Pro Ala Arg Phe Ser Gly
    50                  55                  60

```
Ser Gly Ser Gly Thr Asp Phe Thr Leu Ser Phe Ser Leu Glu Thr
 65                  70                  75                  80

Glu Asp Phe Ala Val Tyr Phe Cys Gln Gln Ser Tyr Ser Trp Pro Leu
                 85                  90                  95

Thr Phe Gly Gln Gly Thr Lys Leu Glu Ile Lys
            100                 105

<210> SEQ ID NO 26
<211> LENGTH: 118
<212> TYPE: PRT
<213> ORGANISM: Artificial Sequence
<220> FEATURE:
<223> OTHER INFORMATION: Enx108A VH

<400> SEQUENCE: 26

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Gly Ala Thr Asp Pro Leu Asp Tyr Trp Gly Gln Gly Thr
            100                 105                 110

Leu Val Thr Val Ser Ser
        115

<210> SEQ ID NO 27
<211> LENGTH: 111
<212> TYPE: PRT
<213> ORGANISM: Artificial Sequence
<220> FEATURE:
<223> OTHER INFORMATION: Enx108A VL

<400> SEQUENCE: 27

Gln Ser Ala Leu Thr Gln Pro Arg Ser Val Ser Gly Ser Pro Gly Gln
  1               5                  10                  15

Ser Val Thr Leu Ser Cys Thr Gly Thr Ser Ser Asp Val Gly Gly Tyr
                 20                  25                  30

Asn Tyr Val Ser Trp Tyr Gln His Tyr Pro Gly Lys Ala Pro Lys Leu
             35                  40                  45

Met Ile Phe Asp Val Asn Glu Arg Ser Gly Val Pro Asp Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Ala Gly Arg
                 85                  90                  95

Tyr Thr Trp Met Phe Gly Gly Thr Lys Val Thr Val Leu Gly
            100                 105                 110

<210> SEQ ID NO 28
<211> LENGTH: 445
<212> TYPE: PRT
```

<213> ORGANISM: Artificial Sequence
<220> FEATURE:
<223> OTHER INFORMATION: Enx108A hIgG4 (L248E, S241P) HC

<400> SEQUENCE: 28

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
385                 390                 395                 400
Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 29
<211> LENGTH: 216
<212> TYPE: PRT
<213> ORGANISM: Artificial Sequence
<220> FEATURE:
<223> OTHER INFORMATION: Enx108A lambda LC

<400> SEQUENCE: 29

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
        35                  40                  45

Met Ile Phe Asp Val Asn Glu Arg Ser Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Arg
                85                  90                  95

Tyr Thr Trp Met Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val His Glu Gly Ser Thr Val Glu Lys
        195                 200                 205

Thr Val Ala Pro Thr Glu Cys Ser
    210                 215

<210> SEQ ID NO 30
<211> LENGTH: 119
<212> TYPE: PRT
<213> ORGANISM: Artificial Sequence
<220> FEATURE:
<223> OTHER INFORMATION: hEnx203 VH

<400> SEQUENCE: 30

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30
```

-continued

Asn Met Asp Trp Val Lys Gln Ala Pro Gly Gln Arg Leu Glu Trp Ile
                35                  40                  45

Gly Asp Ile Asn Pro His Asn Gly Gly Pro Ile Tyr Asn Gln Lys Phe
 50                      55                  60

Thr Gly Arg Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Glu Leu Gly His Trp Tyr Phe Asp Val Trp Gly Gln Gly
                100                 105                 110

Thr Thr Val Thr Val Ser Ser
            115

<210> SEQ ID NO 31
<211> LENGTH: 111
<212> TYPE: PRT
<213> ORGANISM: Artificial Sequence
<220> FEATURE:
<223> OTHER INFORMATION: hEnx203 VL

<400> SEQUENCE: 31

Asp Ile Val Leu Thr Gln Ser Pro Ala Ser Leu Ala Leu Ser Pro Gly
 1               5                  10                  15

Glu Arg Ala Thr Leu Ser Cys Arg Ala Ser Lys Ser Val Ser Thr Ser
                20                  25                  30

Gly Tyr Ser Tyr Ile His Trp Tyr Gln Gln Lys Pro Gly Gln Ala Pro
            35                  40                  45

Arg Leu Leu Ile Tyr Leu Ala Ser Asn Leu Asp Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Glu Glu Asp Phe Ala Thr Tyr Tyr Cys Gln His Ser Arg
                 85                  90                  95

Asp Leu Pro Pro Thr Phe Gly Gln Gly Thr Lys Leu Glu Ile Lys
                100                 105                 110

<210> SEQ ID NO 32
<211> LENGTH: 117
<212> TYPE: PRT
<213> ORGANISM: Artificial Sequence
<220> FEATURE:
<223> OTHER INFORMATION: hEnx209 VH

<400> SEQUENCE: 32

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Met His Trp Leu Arg Gln Arg Pro Gly Gln Gly Leu Glu Trp Ile
            35                  40                  45

Gly Asn Ile Gly Pro Ser Asp Ser Lys Thr His Tyr Asn Gln Lys Phe
 50                  55                  60

Lys Asp Arg Val Thr Met Thr Val Asp Lys Ser Thr Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Tyr Val Leu Phe Thr Tyr Trp Gly Gln Gly Thr Leu
                100                 105                 110

```
Val Thr Val Ser Ser
        115

<210> SEQ ID NO 33
<211> LENGTH: 107
<212> TYPE: PRT
<213> ORGANISM: Artificial Sequence
<220> FEATURE:
<223> OTHER INFORMATION: hEnx209 VL

<400> SEQUENCE: 33

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Tyr Ser Trp Pro Leu
                85                  90                  95

Thr Phe Gly Gln Gly Thr Lys Leu Glu Ile Lys
            100                 105

<210> SEQ ID NO 34
<211> LENGTH: 5
<212> TYPE: PRT
<213> ORGANISM: Artificial Sequence
<220> FEATURE:
<223> OTHER INFORMATION: Enx108A VH CDR1

<400> SEQUENCE: 34

Ser Tyr Gly Met His
1               5

<210> SEQ ID NO 35
<211> LENGTH: 17
<212> TYPE: PRT
<213> ORGANISM: Artificial Sequence
<220> FEATURE:
<223> OTHER INFORMATION: Enx108A VH CDR2

<400> SEQUENCE: 35

Val Ile Ser Tyr Asp Gly Ser Asn Lys Tyr Tyr Ala Asp Ser Val Lys
1               5                   10                  15

Gly

<210> SEQ ID NO 36
<211> LENGTH: 9
<212> TYPE: PRT
<213> ORGANISM: Artificial Sequence
<220> FEATURE:
<223> OTHER INFORMATION: Enx108A VH CDR3

<400> SEQUENCE: 36

Ile Gly Ala Thr Asp Pro Leu Asp Tyr
1               5

<210> SEQ ID NO 37
<211> LENGTH: 14
```

```
<212> TYPE: PRT
<213> ORGANISM: Artificial Sequence
<220> FEATURE:
<223> OTHER INFORMATION: Enx108A VL CDR1

<400> SEQUENCE: 37

Thr Gly Thr Ser Ser Asp Val Gly Gly Tyr Asn Tyr Val Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Enx108A VL CDR2

<400> SEQUENCE: 38

Asp Val Asn Glu Arg Ser Ser
1               5

<210> SEQ ID NO 39
<211> LENGTH: 10
<212> TYPE: PRT
<213> ORGANISM: Artificial Sequence
<220> FEATURE:
<223> OTHER INFORMATION: Enx108A VL CDR3

<400> SEQUENCE: 39

Ala Ser Tyr Ala Gly Arg Tyr Thr Trp Met
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Enx203, hEnx203 VH CDR1

<400> SEQUENCE: 40

Asp Tyr Asn Met Asp
1               5

<210> SEQ ID NO 41
<211> LENGTH: 17
<212> TYPE: PRT
<213> ORGANISM: Artificial Sequence
<220> FEATURE:
<223> OTHER INFORMATION: Enx203, hEnx203 VH CDR2

<400> SEQUENCE: 41

Asp Ile Asn Pro His Asn Gly Gly Pro Ile Tyr Asn Gln Lys Phe Thr
1               5                   10                  15

Gly

<210> SEQ ID NO 42
<211> LENGTH: 10
<212> TYPE: PRT
<213> ORGANISM: Artificial Sequence
<220> FEATURE:
<223> OTHER INFORMATION: Enx203, hEnx203 VH CDR3

<400> SEQUENCE: 42

Gly Glu Leu Gly His Trp Tyr Phe Asp Val
1               5                   10

<210> SEQ ID NO 43
```

```
<211> LENGTH: 15
<212> TYPE: PRT
<213> ORGANISM: Artificial Sequence
<220> FEATURE:
<223> OTHER INFORMATION: Enx203, hEnx203 VL CDR1

<400> SEQUENCE: 43

Arg Ala Ser Lys Ser Val Ser Thr Ser Gly Tyr Ser Tyr Ile His
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: Enx203, hEnx203 VL CDR2

<400> SEQUENCE: 44

Leu Ala Ser Asn Leu Asp Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Enx203, hEnx203 VL CDR3

<400> SEQUENCE: 45

Gln His Ser Arg Asp Leu Pro Pro Thr
1               5

<210> SEQ ID NO 46
<211> LENGTH: 5
<212> TYPE: PRT
<213> ORGANISM: Artificial Sequence
<220> FEATURE:
<223> OTHER INFORMATION: Enx209, hEnx209 VH CDR1

<400> SEQUENCE: 46

Asn Tyr Trp Met His
1               5

<210> SEQ ID NO 47
<211> LENGTH: 17
<212> TYPE: PRT
<213> ORGANISM: Artificial Sequence
<220> FEATURE:
<223> OTHER INFORMATION: Enx209, hEnx209 VH CDR2

<400> SEQUENCE: 47

Asn Ile Gly Pro Ser Asp Ser Lys Thr His Tyr Asn Gln Lys Phe Lys
1               5                   10                  15

Asp

<210> SEQ ID NO 48
<211> LENGTH: 8
<212> TYPE: PRT
<213> ORGANISM: Artificial Sequence
<220> FEATURE:
<223> OTHER INFORMATION: Enx209, hEnx209 VH CDR3

<400> SEQUENCE: 48

Gly Asp Tyr Val Leu Phe Thr Tyr
1               5
```

```
<210> SEQ ID NO 49
<211> LENGTH: 11
<212> TYPE: PRT
<213> ORGANISM: Artificial Sequence
<220> FEATURE:
<223> OTHER INFORMATION: Enx209, hEnx209 VL CDR1

<400> SEQUENCE: 49

Arg Ala Ser Gln Ser Ile Ser Asn Asn Leu His
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Enx209, hEnx209 VL CDR2

<400> SEQUENCE: 50

Tyr Ala Ser Gln Ser Ile Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Enx209, hEnx209 VL CDR3

<400> SEQUENCE: 51

Gln Gln Ser Tyr Ser Trp Pro Leu Thr
1               5

<210> SEQ ID NO 52
<211> LENGTH: 330
<212> TYPE: PRT
<213> ORGANISM: Homo sapiens

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 53
<211> LENGTH: 327
<212> TYPE: PRT
<213> ORGANISM: Homo sapiens

<400> SEQUENCE: 53

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 54
<211> LENGTH: 107
<212> TYPE: PRT
<213> ORGANISM: Homo sapiens

<400> SEQUENCE: 54

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 55
<211> LENGTH: 106
<212> TYPE: PRT
<213> ORGANISM: Homo sapiens

<400> SEQUENCE: 55

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 56
<211> LENGTH: 449
<212> TYPE: PRT
<213> ORGANISM: Artificial Sequence
<220> FEATURE:
<223> OTHER INFORMATION: hEnx203 hIgG1 HC

<400> SEQUENCE: 56

```
Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala Pro Gly Gln Arg Leu Glu Trp Ile
        35                  40                  45

Gly Asp Ile Asn Pro His Asn Gly Gly Pro Ile Tyr Asn Gln Lys Phe
    50                  55                  60

Thr Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 57
<211> LENGTH: 218
<212> TYPE: PRT
<213> ORGANISM: Artificial Sequence
<220> FEATURE:
<223> OTHER INFORMATION: hEnx203 kappa LC

<400> SEQUENCE: 57

```
Asp Ile Val Leu Thr Gln Ser Pro Ala Ser Leu Ala Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Ile His Trp Tyr Gln Gln Lys Pro Gly Gln Ala Pro
        35                  40                  45

Arg Leu Leu Ile Tyr Leu Ala Ser Asn Leu Asp Ser Gly Val Pro Ala
50                  55                  60

Arg Phe Ser Gly Ser Gly Ser Gly Thr Asp Phe Thr Leu Thr Ile Ser
65                  70                  75                  80

Ser Leu Glu Glu Glu Asp Phe Ala Thr Tyr Tyr Cys Gln His Ser Arg
                85                  90                  95

Asp Leu Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 58
<211> LENGTH: 444
<212> TYPE: PRT
<213> ORGANISM: Artificial Sequence
<220> FEATURE:
<223> OTHER INFORMATION: hEnx209 hIgG4 (L248E, S241P) HC

<400> SEQUENCE: 58

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Leu Arg Gln Arg Pro Gly Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415
```

```
Gly Asn Val Phe Ser Cys Ser Val Met His Glu Ala Leu His Asn His
                420                 425                 430
Tyr Thr Gln Lys Ser Leu Ser Leu Ser Leu Gly Lys
        435                 440

<210> SEQ ID NO 59
<211> LENGTH: 214
<212> TYPE: PRT
<213> ORGANISM: Artificial Sequence
<220> FEATURE:
<223> OTHER INFORMATION: hEnx209 kappa LC

<400> SEQUENCE: 59

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Tyr Ser Trp Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```